(12) United States Patent
Sanz Molinero

(10) Patent No.: US 8,071,840 B2
(45) Date of Patent: Dec. 6, 2011

(54) PLANTS HAVING INCREASE YIELD AND METHOD FOR MAKING THE SAME

(75) Inventor: Ana Isabel Sanz Molinero, Gentbrugge (BE)

(73) Assignee: CropDesign N.V. (BE)

( * ) Notice: Subject to any disclaimer, the term of this patent is extended or adjusted under 35 U.S.C. 154(b) by 645 days.

(21) Appl. No.: 11/991,766

(22) PCT Filed: Sep. 15, 2006

(86) PCT No.: PCT/EP2006/066425
§ 371 (c)(1),
(2), (4) Date: Apr. 21, 2008

(87) PCT Pub. No.: WO2007/031581
PCT Pub. Date: Mar. 22, 2007

(65) Prior Publication Data
US 2009/0193543 A1 Jul. 30, 2009

Related U.S. Application Data

(60) Provisional application No. 60/717,738, filed on Sep. 19, 2005.

(30) Foreign Application Priority Data

Sep. 15, 2005 (EP) .................................. 05108483

(51) Int. Cl.
*A01H 1/00* (2006.01)
*A01H 5/00* (2006.01)
*C12N 15/82* (2006.01)

(52) U.S. Cl. ............ 800/278; 800/295; 435/410; 435/4; 435/468; 536/23.6

(58) Field of Classification Search ......................... None
See application file for complete search history.

(56) References Cited

U.S. PATENT DOCUMENTS 5,981,842 A * 11/1999 Wu et al. ..................... 800/298
2003/0233670 A1 12/2003 Edgerton et al.
2004/0034888 A1 2/2004 Liu et al.
2005/0268358 A1 * 12/2005 Frankard et al. ............... 800/290

FOREIGN PATENT DOCUMENTS

| WO | WO-94/10831 A1 | 5/1994 |
| WO | WO-97/13843 A1 | 4/1997 |
| WO | WO 2005/083094 * | 9/2005 |
| WO | WO-2005/083094 A2 | 9/2005 |

OTHER PUBLICATIONS

Chen et al, Database UniProt_15.5, Accession No. T04147, Apr. 23, 1999.*
Chow, T.-Y., et al., "Oryza sativa BAC OJ1288_A07 genomic sequence", Database UniProt Accession No. Q65XN9, Oct. 25, 2004.
Sivamani, E., et al., "Improved Biomass Productivity and Water Use Efficiency Under Water Deficit Conditions in Transgenic Wheat Constitutively Expressing the Barley *HVA*1 Gene", Plant Science, vol. 155, (2000), pp. 1-9.
Dunwell, J.M., "Transgenic Approaches to Crop Improvement", Journal of Experimental Botany, vol. 51, GMP Special Issue, (2000), pp. 487-496.
Liu, J., et al., "Plant full length insert polynucleotide seq id 29183", Database Geneseq Accession No. ADX54443, Apr. 21, 2005.
Edgerton, M.D., et al., "Polynucleotide sequence #31 useful in producing transgenic plants", Database Geneseq Accession No. ADM47613, Jun. 3, 2004.
Curry, J., et al., "Late Embryogenesis Abundant Protein, group 3 (LEA) (PMA2005)", Database UniProt Accession No. Q03968, Nov. 1, 1996.
Curry, J., et al., "Sequence Analysis of a cDNA Encoding a Group 3 LEA mRNA Inducible by ABA or Dehydration Stress in Wheat", Plant Molecular Biology, vol. 16, (1991), pp. 1073-1076.

* cited by examiner

*Primary Examiner* — Eileen B O'Hara
(74) *Attorney, Agent, or Firm* — Connolly Bove Lodge & Hutz LLP

(57) ABSTRACT

The present invention concerns a method for increasing plant yield by modulating expression in a plant of a nucleic acid encoding an OsLEA3a polypeptide or a homologue thereof. One such method comprises introducing into a plant an OsLEA3a nucleic acid or variant thereof. The invention also relates to transgenic plants having introduced therein an OsLEA3a nucleic acid or variant thereof, which plants have increased yield and altered metabolic profile, relative to control plants. The present invention also concerns constructs useful in the methods of the invention.

33 Claims, 11 Drawing Sheets

MASHQDQASYRAGETKAHTEEKAGQVMGASKDKASEAKDRASEAAGHAAGKGQDTKEA

TKEKAQAAKERASETAQAAKDKTSSTSQAARDKAAESKDQTGGFLGEKTEQAKQKAAE

TAGAAKQKTAETAQYTKDSAIAGKDKTGSVLQQASEQVKSTVVGAKDAVMSTLGMTED

EAGTDDGANKD*TSATAAATETT*ARDH

SEQ ID NO: 1

ATGGCTTCCCACCAGGACCAGGCTAGCTACCGCGCCGGCGAGACCAAGGCCCACACCGAGGA
GAAGGCGGGGCAGGTGATGGGGGCGAGCAAGGACAAGGCGAGCGAGGCGAAGGACAGGGCGT
CGGAGGCGGCGGGGCACGCCGCCGGCAAGGGGCAGGATACCAAGGAGGCGACGAAGGAGAAG
GCGCAGGCGGCGAAGGAGAGGGCGTCGGAGACGGCGCAGGCGGCGAAGGACAAGACCTCCAG
CACGTCGCAGGCGGCGAGGGACAAAGCCGCCGAGAGCAAGGACCAGACCGGCGGCTTCCTCG
GCGAGAAGACCGAGCAGGCCAAGCAGAAGGCCGCCGAGACCGCTGGCGCCGCCAAGCAGAAG
ACCGCCGAGACGGCGCAGTACACCAAGGACTCTGCCATCGCCGGCAAGGACAAGACCGGCAG
CGTCCTCCAACAGGCGAGTGAGCAGGTGAAGAGCACGGTGGTCGGCGCCAAGGACGCGGTGA
TGAGCACGCTGGGGATGACCGAAGACGAGGCCGGCACCGACGACGGCGCCAACAAGGACACC
TCTGCCACCGCCGCCGCCACGGAGACGACGGCGAGGGATCACTAG

SEQ ID NO: 2

MASHQDQASYRAGETKAHTEEKAGQVMGASKDKASEAKDRASEAAGHAAGKGQDTKEATKEK
AQAAKERASETAQAAKDKTSSTSQAARDKAAESKDQTGGFLGEKTEQAKQKAAETAGAAKQK
TAETAQYTKDSAIAGKDKTGSVLQQASEQVKSTVVGAKDAVMSTLGMTEDEAGTDDGANKDT
SATAAATETTARDH

SEQ ID NO: 3

T(S/T/A/K)(Q/E/D)A(A/T)(R/K)(D/Q/E)(K/R)A(A/G/Y)(E/G)

SEQ ID NO: 4 prm06118

GGGGACAAGTTTGTACAAAAAAGCAGGCTTAAACAATGGCTTCCCACCAGGA

SEQ ID NO: 5 prm06119

GGGGACCACTTTGTACAAGAAAGCTGGGTAAATCATTCACGGCGTCTAGT

SEQ ID NO: 6, rice GOS2 promoter
AATCCGAAAAGTTTCTGCACCGTTTTCACCCCTAACTAACAATATAGGGAACGTGTGCTAA
ATATAAAATGAGACCTTATATATGTAGCGCTGATAACTAGAACTATGCAAGAAAAACTCATC
CACCTACTTTAGTGGCAATCGGGCTAAATAAAAAGAGTCGCTACACTAGTTTCGTTTTCCT
TAGTAATTAAGTGGGAAAATGAAATCATTATTGCTTAGAATATACGTTCACATCTCTGTCAT
GAAGTTAAATTATTCGAGGTAGCCATAATTGTCATCAAACTCTTCTTGAATAAAAAAATCTT
TCTAGCTGAACTCAATGGGTAAAGAGAGAGATTTTTTTAAAAAAATAGAATGAAGATATTC
TGAACGTATTGGCAAAGATTTAAACATATAATTATATAATTTTATAGTTTGTGCATTCGTCA
TATCGCACATCATTAAGGACATGTCTTACTCCATCCCAATTTTTATTTAGTAATTAAAGACA
ATTGACTTATTTTTATTATTTATCTTTTTTCGATTAGATGCAAGGTACTTACGCACACACTT
TGTGCTCATGTGCATGTGTGAGTGCACCTCCTCAATACACGTTCAACTAGCAACACATCTCT
AATATCACTCGCCTATTTAATACATTTAGGTAGCAATATCTGAATTCAAGCACTCCACCATC
ACCAGACCACTTTTAATAATATCTAAATACAAAAAATAATTTTACAGAATAGCATGAAAAG

FIGURE 3 A

TATGAAACGAACTATTTAGGTTTTTCACATACAAAAAAAAAAAGAATTTTGCTCGTGCGCGA
GCGCCAATCTCCCATATTGGGCACACAGGCAACAACAGAGTGGCTGCCCACAGAACAACCCA
CAAAAAACGATGATCTAACGGAGGACAGCAAGTCCGCAACAACCTTTTAACAGCAGGCTTTG
CGGCCAGGAGAGAGGAGGAGAGGCAAAGAAAACCAAGCATCCTCCTCCTCCCATCTATAAAT
TCCTCCCCCCTTTTCCCCTCTCTATATAGGAGGCATCCAAGCCAAGAAGAGGGAGAGCACCA
AGGACACGCGACTAGCAGAAGCCGAGCGACCGCCTTCTTCGATCCATATCTTCCGGTCGAGT
TCTTGGTCGATCTCTTCCCTCCTCCACCTCCTCCTCACAGGGTATGTGCCCTTCGGTTGTTC
TTGGATTTATTGTTCTAGGTTGTGTAGTACGGGCGTTGATGTTAGGAAAGGGGATCTGTATC
TGTGATGATTCCTGTTCTTGGATTTGGGATAGAGGGGTTCTTGATGTTGCATGTTATCGGTT
CGGTTTGATTAGTAGTATGGTTTTCAATCGTCTGGAGAGCTCTATGGAAATGAAATGGTTTA
GGGTACGGAATCTTGCGATTTTGTGAGTACCTTTTGTTTGAGGTAAAATCAGAGCACCGGTG
ATTTTGCTTGGTGTAATAAAAGTACGGTTGTTTGGTCCTCGATTCTGGTAGTGATGCTTCTC
GATTTGACGAAGCTATCCTTTGTTTATTCCCTATTGAACAAAAATAATCCAACTTTGAAGAC
GGTCCCGTTGATGAGATTGAATGATTGATTCTTAAGCCTGTCCAAAATTTCGCAGCTGGCTT
GTTTAGATACAGTAGTCCCCATCACGAAATTCATGGAAACAGTTATAATCCTCAGGAACAGG
GGATTCCCTGTTCTTCCGATTTGCTTTAGTCCCAGAATTTTTTTCCCAAATATCTTAAAAA
GTCACTTTCTGGTTCAGTTCAATGAATTGATTGCTACAAATAATGCTTTTATAGCGTTATCC
TAGCTGTAGTTCAGTTAATAGGTAATACCCCTATAGTTTAGTCAGGAGAAGAACTTATCCGA
TTTCTGATCTCCATTTTTAATTATATGAAATGAACTGTAGCATAAGCAGTATTCATTTGGAT
TATTTTTTTATTAGCTCTCACCCCTTCATTATTCTGAGCTGAAAGTCTGGCATGAACTGTC
CTCAATTTTGTTTTCAAATTCACATCGATTATCTATGCATTATCCTCTTGTATCTACCTGTA
GAAGTTTCTTTTTGGTTATTCCTTGACTGCTTGATTACAGAAAGAAATTTATGAAGCTGTAA
TCGGGATAGTTATACTGCTTGTTCTTATGATTCATTTCCTTTGTGCAGTTCTTGGTGTAGCT
TGCCACTTTCACCAGCAAAGTTC

SEQ ID NO:7, GenBank Acc Nr AK119713

AGCCAGTGCAAATCTGATCGATCAAGGTAATCGAGCAAAATCCATCAGAGTTCTAACATTCG
CGCGTGAATTTCGAGGTTAATTTTTGAAGCTTAGGATCAATGGCTTCCCACCAGGACCAGGC
TAGCTACCGCGCCGGCGAGACCAAGGCCCACACCGAGGAGAAGGCGGGGCAGGTGATGGGGG
CGAGCAAGGACAAGGCGAGCGAGGCGAAGGACAGGGCGTCGGAGGCGGCGGGGCACGCCGCC
GGCAAGGGGCAGGATACCAAGGAGGCGACGAAGGAGAAGGCGCAGGCGGCGAAGGAGAGGGC
GTCGGAGACGGCGCAGGCGGCGAAGGACAAGACCTCCAGCACGTCGCAGGCGGCGAGGGACA
AGCCGCCGAGAGCAAGGACCAGACCGGCGGCTTCCTCGGCGAGAAGACCGAGCAGGCCAAG
CAGAAGGCCGCCGAGACCGCTGGCGCCGCCAAGCAGAAGACCGCCGAGACGGCGCAGTACAC
CAAGGACTCTGCCATCGCCGGCAAGGACAAGACCGGCAGCGTCCTCCAACAGGCGAGTGAGC
AGGTGAAGAGCACGGTGGTCGGCGCCAAGGACGCGGTGATGAGCACGCTGGGGATGACCGAA
GACGAGGCCGGCACCGACGACGGCGCCAACAAGGACACCTCTGCCACCGCCGCCGCCGCGGA
GACGACGGCGAGGGATCACTAGACGCCGTGAATGATTTCCCTTTGGGTCTATTTATGTATGT
TTTCACTTCAAATTCGGTGCAAGTTTGAATTTGTTTTTGTGTCGTTTTGAGTCTGTATCGAT
GCTGTATGAAGTGGTGGTCGTCGCAGGGGAGGATTTCTGACGGGTGTGGGTGATGTGTACTG
ATGATGTTCAGTTGTTTTCGTCAGAGTTTCTCGTCTGTGTTCTGTTTATTATGGCGTAACAA
TAATAAAAGTTTGGGCCTAAAGCCCGCATTTGTGGTTT

FIGURE 3 B

SEQ ID NO: 8, GenBank Acc Nr AK119713, deduced protein sequence

MASHQDQASYRAGETKAHTEEKAGQVMGASKDKASEAKDRASEAAGHAAGKGQDTKEATKEK
AQAAKERASETAQAAKDKTSSTSQAARDKAAESKDQTGGFLGEKTEQAKQKAAETAGAAKQK
TAETAQYTKDSAIAGKDKTGSVLQQASEQVKSTVVGAKDAVMSTLGMTEDEAGTDDGANKDT
SATAAAAETTARDH

SEQ ID NO: 9, GenBank Z68090

GATCAAGATAATCGAGCAAAATCCATCAGAGTTCTAACATTCGCGCGTGAATTTCGAGGTTA
ATTTTTGAAGCTTAGGATCAATGGCTTCCCACCAGGACCAGGCTAGCTACCGCGCCGGCGAG
ACCAAGGCCCACACCGAGGAGAAGGCGGTGCAGGTGATGGGGGCGAGCAAGGACAAGGCGAG
CGAGGCGAAGGACAGAGCGTCGGAGGCGGCGGTGCACGCCGCCGGCAAGGGGCAGGATACCA
AGGAGGCGACGAAGGAGAAGGCGCAGGCGGCGAAGGAGAGGGCGTCGGAGACGGCGCAGGCG
GCGAAGGACAAGACCTCCGGCACGGCGCAGGCGGCGAGGGACAAAGCCGCCGAGAGCAAGGA
CCAGACCGGCGGCTTCCTCGGCGAGAAGACCGAGCAGGCCAAGCAGAAGGCCGCCGAGACCG
CTGGCGCCGCCAAGCAGAAGACCGCCGAGACGGCGCAGTACACCAAGGACTCTGCCATCGCC
GGCAAGGACAAGACCGGCAGCGTCCTCCAACAGGCGAGTGAGCAGGTGAAGAGCACGGTGGT
CGGCGCCAAGGACGCGGTGATGAGCACGCTGGGGATGACCGAAGACAAGGCCGGCACCGACG
ACGGCGCCAACAAGGACACCTCTGCCACCGCCGCCGCCACGGAGACGACGGCGAGGGATCAC
TAGACGCCGTGAATGATTTCCCTTTGGGTCTATTTATGTATGTTTTCACTTCAAATTCGGTG
CAAGTTTGAATTTGTTTTTGTGTCGTTTTGAGTCTGTATCGATGCTGTATGAAGTGGTGGTC
GTCGCAGGGGAGGATTTCTGACGGGTGTGGGTGATGTGTACTGATGATGTTCAGTTGTTTTC
GTCAGAGTTTCTCGTCTGTGTTCTGTTTATTATGGCGTAACAATAATAAAAGTTTGGGCCTA
AAGCCCGCATTTGTGGTTTAAAAAAAAAAAAAAAAA

SEQ ID NO: 10, GenBank Z68090 deduced protein sequence

MASHQDQASYRAGETKAHTEEKAVQVMGASKDKASEAKDRASEAAVHAAGKGQDTKEATKEK
AQAAKERASETAQAAKDKTSGTAQAARDKAAESKDQTGGFLGEKTEQAKQKAAETAGAAKQK
TAETAQYTKDSAIAGKDKTGSVLQQASEQVKSTVVGAKDAVMSTLGMTEDKAGTDDGANKDT
SATAAATETTARDH

SEQ ID NO: 11, derived from AF046884

ATGGCTTCCCACCAGGACCAGGCTAGCTACCGCGCCGGCGAGACCAAGGCCCACACCGAGGA
GAAGGCGGGGCAGGTGATGGGGGCGAGCAAGGACAAGGCGAGCGAGGCGAAGGACAGGGCGT
CGGAGGCGGCGGGGCACGCCGCCGGCAAGGGGCAGGATACCAAGGAGGCGACGAAGGACAAG
GCGCAGGCGGCGAAGGATAGGGCGTCGGAGACGGCGCAGGCGGCGAAGGACAAGACCTCCAG
CACGTCGCAGGCGGCGAGGGACAAAGCCGCCGAGAGCAAGGACCAGACCGGCGGCTTCCTCG
GCGAGAAGACCGAGCAGGCCAAGCAGAAGGCCGCCGAGACCGCTGGCGCCGCCAAGCAGAAA
ACCCCCGAGACGGCGCAGTACACCAAGGACTCTGCCATCGCCGGCAAGGACAAGACCGGCAG
CGTCCTCCAACAGGCGAGTGAGCAGGTGAAGAGCACGGTGGTCGGCGCCAAGGACGCGGTGA
TGAGCACGCTGGGGATGACCGAAGACGAGGCCGGCACCGACGACGGCGCCAACAAGGACACC
TCTGCCACCGCCGCCGCCACGGAGACGACGGCGAGGGATCACTAG

FIGURE 3 C

SEQ ID NO: 12, deduced protein sequence of SEQ ID NO: 11

MASHQDQASYRAGETKAHTEEKAGQVMGASKDKASEAKDRASEAAGHAAGKGQDTKEATKDK
AQAAKDRASETAQAAKDKTSSTSQAARDKAAESKDQTGGFLGEKTEQAKQKAAETAGAAKQK
TPETAQYTKDSAIAGKDKTGSVLQQASEQVKSTVVGAKDAVMSTLGMTEDEAGTDDGANKDT
SATAAATETTARDH

SEQ ID NO: 13, AK073837

GACAAGGCAAGAGGCAAGAGGCAAGAGCATCCGTATTAACCAGCCTTTTGAGACTTGAGAGT
GTGTGTGACTCGATCCAGCGTAGTTTCAGTTCGTGTGTTGGTGAGTGATTCCAGCCAAGTTT
GCGATGGCTTCTCAGCAGGAACGGGCTAGCTACCACGCCGGCGAGACCAAGGCCCACGCCGA
GGAGAAGACGGGGCGCATGATGGGCACGGCGCAGGAGAAGGCGCGGGAGGCCAAGGACACGG
CGTCCGACGCCGCGGGGCGCGCGATGGGCAGGGACACGGCGCCAAGGAGGCGACCAAGGAG
AAGGCGTACGAGACCAAGGACGCGACCAAGGAGAAGGCGTACGAGGCAAAGGACGCGGCCTC
CGACGCCACCGGCCGCGCCATGGACAAGGGCCGCGGCGCCGCGGGCGCCACGAGGGACAAGG
CGTACGATGCCAAGGACAGGGCGGCTGACACGGCGCAGTCCGCCGCCGACCGCGCCCGCGAC
GGCGCCGGGCAGACCGGGAGCTACATTGGACAGACCGCCGAGGCCGCCAAGCAGAAAGCGGC
CGGCGCCGCGCAGTACGCCAAGGAGACCGCGATCGCCGGCAAGGACAAGACCGGCGCCGTGC
TCCAGCAGGCAGGGGAGCAGGTGAAGAGCGTGGCGGTGGGGGCGAAGGACGCGGTGATGTAC
ACGCTCGGGATGTCAGGCGATAACAAGAACAACGCCGCTGCCGGCAAGGACACCAGCACCTA
CAAGCCTGGAACTGGGAGTGACTACCAGTAATACGGTATAAGAAGCATGTGTCGTCTTTGGC
ACTGATGCCAAAGTGTACGTGTTGTATCCTCTTTTTTAAGTTTCAGCTCGACTTCGACGTGT
TCGGTGTCACACTTTGGTTTTTCAGTTGTGCTCAACTGTTCATGTTTCTGGTTCCATGGAGG
GCCAGTGTGGAGGTCAATGTTTAAGCTTTCGTTTTAAAATCTGATAATAAAGTTGGTTAAGA
CCTG

SEQ ID NO: 14, AK073837, deduced protein sequence (nt 128-772)

MASQQERASYHAGETKAHAEEKTGRMMGTAQEKAREAKDTASDAAGRAMGRGHGAKEATKEK
AYETKDATKEKAYEAKDAASDATGRAMDKGRGAAGATRDKAYDAKDRAADTAQSAADRARDG
AGQTGSYIGQTAEAAKQKAAGAAQYAKETAIAGKDKTGAVLQQAGEQVKSVAVGAKDAVMYT
LGMSGDNKNNAAAGKDTSTYKPGTGSDYQ

SEQ ID NO: 15, AK064074

GTCACAAGGCAAGAGGCAAGAGGCAAGAGCATCCGTATTAACCAGCCTTTTGAGACTTGAGA
GTGTGTGTGACTCGATCCAGCGTAGTTTCAGTTCGTGTGTTGGTGAGTGATTCCAGCCAAGT
TTGCGATGGCTTCTCAGCAGGAACGGGCTAGCTACCACGCCGGCGAGACCAAGGCCCGCGCC
GAGGAGAAGACGGGGCGCATGATGGGCACGGCGCAGGAGAAGGCGCGGGAGGCCAAGGACAC
GGCGTCCGACGCCGCGGGGCGCGCGATGGGCAGGGACACGGCGCCAAGGAGGCGACCAAGG
AGAAGGCGTACGAGACCAAGGACGCGACCAAGGAGAAGGCGTACGAGGCAAAGGACGCGGCC
TCCGACGCCACCGGCCGCGCCATGGACAAGGGCCGCGGCGCCGCGGGCGCCACGAGGGACAA
GGCGTACGATGCCAAGGACAGGGCGGCTGACACGGCGCAGTCCGCCGCCGACCGCGCCCGCG
ACGGCGCCGGGCAGACCGGGAGCTACATTGGACAGACCGCCGAGGCCGCCAAGCAGAAAGCG

FIGURE 3 D

```
GCCGGCGCCGCGCAGTACGCCAAGGAGACCGCGATCGCCGGCAAGGACAAGACCGGCGCCGT
GCTCCAGCAGGCAGGGGAGCAGGTGAAGAGCGTGGCGGTGGGGGCGAAGGACGCGGTGATGT
ACACGCTCGGGATGTCAGGCGATAACAAGAACAACGCCGCTGCCGGCAAGGACACCAGCACC
TACAAGCCTGGAACTGGGAGTGACTACCAGTAATACGGTATAAGAAGCATGTGTCGTCTTTG
GCACTGATGCCAAAGTGTACGTGTTGTATCCTCTTTTTTAAGTTTCAGCTCGACTTCGACGT
GTTCGGTGTCACACTTTGGTTTTTCAGTTGTGCTCAACTGTTCATGTTTCTGGTTCCATGGA
GGGCCAGTGTGGAGGTCAATGTTTAAGCTTTCGTTTTAAAATCTGATAATAAAGTTGGTTAA
GACCTGAAAGCGTT
```

SEQ ID NO: 16, AK064074 deduced protein sequence (nt 130-774)

```
MASQQERASYHAGETKARAEEKTGRMMGTAQEKAREAKDTASDAAGRAMGRGHGAKEATKEK
AYETKDATKEKAYEAKDAASDATGRAMDKGRGAAGATRDKAYDAKDRAADTAQSAADRARDG
AGQTGSYIGQTAEAAKQKAAGAAQYAKETAIAGKDKTGAVLQQAGEQVKSVAVGAKDAVMYT
LGMSGDNKNNAAAGKDTSTYKPGTGSDYQ
```

SEQ ID NO: 17, NM_191640

```
ATGGCTTCTCAGCAGGAACGGGCTAGCTACCACGCCGGCGAGACCAAGGCCCGCGCCGAGGA
GAAGACGGGGCGCATGATGGGCACGGCGCAGGAGAAGGCGCGGGAGGCCAAGGACACGGCGT
CCGACGCCGCGGGGCGCGCGATGGGCAGGGGACACGGCGCCAAGGAGGCGACCAAGGAGAAG
GCGTACGAGACCAAGGACGCGACCAAGGAGAAGGCGTACGAGGCAAAGGACGCGGCCTCCGA
CGCCACCGGCCGCGCCATGGACAAGGGCCGCGGCGCCGCGGGCGCCACGAGGGACAAGGCGT
ACGATGCCAAGGACAGGGCGGCTGACACGGCGCAGTCCGCCGCCGACCGCGCCCGCGACGGC
GCCGGGCAGACCGGGAGCTACATTGGACAGACCGCCGAGGCCGCCAAGCAGAAAGCGGCCGG
CGCCGCGCAGTACGCCAAGGAGACCGCGATCGCCGGCAAGGACAAGACCGGCGCCGTGCTCC
AGCAGGCAGGGGAGCAGGTGAAGAGCGTGGCGGTGGGGGCGAAGGACGCGGTGATGTACACG
CTCGGGATGTCAGGCGATAACAAGAACAACGCCGCTGCCGGCAAGGACACCAGCACCTACAA
GCCTGGAACTGGGAGTGACTACCAGTAA
```

SEQ ID NO: 18, NM_191640, deduced protein sequence

```
MASQQERASYHAGETKARAEEKTGRMMGTAQEKAREAKDTASDAAGRAMGRGHGAKEATKEK
AYETKDATKEKAYEAKDAASDATGRAMDKGRGAAGATRDKAYDAKDRAADTAQSAADRARDG
AGQTGSYIGQTAEAAKQKAAGAAQYAKETAIAGKDKTGAVLQQAGEQVKSVAVGAKDAVMYT
LGMSGDNKNNAAAGKDTSTYKPGTGSDYQ
```

SEQ ID NO: 19, D26536,

```
AAGAGGCAAGAGCATCCGTATTAACCAGCCTTTTGAGACTTGAGAGTGTGTGTGACTCGATC
CAGCGTAGTTTCAGTTCGTGTGTTGGTGAGTGATTCCAGCCAAGTTTGCGATGGCTTCTCAG
CAGGAACGGGCTAGCTACCACGCCGGCGAGACCAAGGCCCGCGCCGAGGAGAAGACGGGGCG
CATGATGGGCACGGCGCAGGAGAAGGCGCGGGAGGCCAAGGACACGGCGTCCGACGCCGCGG
GCGCGCGATGGGCAGGGGACACGGCGCCAAGGAGGCGACCAAGGAGAAGGCGTACGAGACC
AAGGACGCGACCAAGGAGAAGGCGTACGAGGCAAAGGACGCGGCCTCCGACGCCACCGGCCG
CGCCATGGACAAGGGCCGCGCCGCGGGCGCCACGAGGGACAAGGCGTACGATGCCAAGGACA
```

FIGURE 3 E

```
GGGCGGCTGACACGGCGCAGTCCGCCGCCGACCGCGCCCGCGACGGCGCCGGGCAGACCGGG
AGCTACATTGGACAGACCGCCGAGGCCGCCAAGCAGAAAGCGGCCGGCGCCGCGCAGTACGC
CAAGGAGACCGCGATCGCCGGCAAGGACAAGACCGGCGCCGTGCTCCAGCAGGCAGGGGAGC
AGGTGAAGAGCGTGGCGGTGGGGGCGAAGGACGCGGTGATGTACACGCTCGGGATGTCAGGC
GATAACAAGAACAACGCCGCTGCCGGCAAGGACACCAGCACCTACAAGCCTGGAACTGGGAG
TGACTACCAGTAATACGGTAGAAGAAGCATGTGTCGTCTTTGGCACTGATGCCAAAGTGTAC
GTGTTGTATCCTCTTTTTTAAGTTTCAGCTCGACTTCGACGTGTTCGGTGTCACACTTTGGT
TTTTCAGTTGTGCTCAACTGTTCATGTTTCTGGTTCCATGGAGGGCCAGTGTGGAGGTCAAT
GTTTAAGCTTTCGTTTTAAAATCTGATAATAAAGTTGGTTAAGACCTG
```

SEQ ID NO: 20, D26536, deduced protein sequence

```
MASQQERASYHAGETKARAEEKTGRMMGTAQEKAREAKDTASDAAGRAMGRGHGAKEATKEK
AYETKDATKEKAYEAKDAASDATGRAMDKGRAAGATRDKAYDAKDRAADTAQSAADRARDGA
GQTGSYIGQTAEAAKQKAAGAAQYAKETAIAGKDKTGAVLQQAGEQVKSVAVGAKDAVMYTL
GMSGDNKNNAAAGKDTSTYKPGTGSDYQ
```

SEQ ID NO: 21, X13498 Barley LEA3a coding sequence

```
ATGGCCTCCAACCAGAACCAGGGGAGCTACCACGCCGGCGAGACCAAGGCCCGCACCGAGGA
GAAGACCGGGCAGATGATGGGCGCCACCAAGCAGAAGGCGGGGCAGACCACCGAGGCCACCA
AGCAGAAGGCCGGCGAGACGGCCGAGGCCACCAAGCAGAAGACCGGCGAGACGGCCGAGGCC
GCCAAGCAGAAGGCCGCCGAGGCCAAGGACAAGACGGCGCAGACGGCGCAGGCGGCCAAGGA
CAAGACGTACGAGACGGCGCAGGCGGCCAAGGAGCGCGCCGCCCAGGGCAAGGACCAGACCG
GCAGCGCCCTCGGCGAGAAGACGGAGGCGGCCAAGCAGAAGGCCGCCGAGACGACGGAGGCG
GCCAAGCAGAAGGCCGCCGAGGCAACCGAGGCGGCCAAGCAGAAGGCGTCCGACACGGCGCA
GTACACCAAGGAGTCCGCGGTGGCCGGCAAGGACAAGACCGGCAGCGTCCTCCAGCAGGCCG
GCGAGACGGTGGTGAACGCCGTGGTGGGCGCCAAGGACGCCGTGGCAAACACGCTGGGCATG
GGAGGGGACAACACCAGCGCCACCAAGGACGCCACCACCGGCGCCACCGTCAAGGACACCAC
CACCACCACCAGGAATCACTAG
```

SEQ ID NO: 22, CAA31853, Barley LEA3a protein sequence

```
MASNQNQGSYHAGETKARTEEKTGQMMGATKQKAGQTTEATKQKAGETAEATKQKTGETAEA
AKQKAAEAKDKTAQTAQAAKDKTYETAQAAKERAAQGKDQTGSALGEKTEAAKQKAAETTEA
AKQKAAEATEAAKQKASDTAQYTKESAVAGKDKTGSVLQQAGETVVNAVVGAKDAVANTLGM
GGDNTSATKDATTGATVKDTTTTTRNH
```

SEQ ID NO: 23, Bromus inermis

```
ATGGCATCCAACCAGGACAAGGCAAGCTACCACGCCGGCGAGGCCAAGGCCCGCACCGAGGA
GAAGGCCGGACAGGTGACCGGCGCGGCCAAGGACAAGGCGTGCGAGGCCAAGGACCGGGCGT
CGGACGCGGCGGGGCACGCGACCGGGAAGGGGCAGGGCGCCGTCGAGGCCACGAAGCAGAAG
GCCGGCGAGGCGGGGCAGAAGACGTCCGAGACGGCGCAGGCCGCCAAGGACCGGGCCGCCGA
GGGCAAGGACCAGGCCGGCAGCTACCTCGGCCAGACGGCCGAGGCCGCCAAGGAGAAGGCCT
CCCAGGCGACGGGGTACACGCAGGACAGGGCCGCCGACGCGGCGCAGTACACGAAGGACTCC
```

FIGURE 3 F

```
GCCGTCGCCGGCAAGGACAAGACCGGCAGCGTCCTCGCTCAGGCCGGCGAGCAGGTGAAGAA
CGTGGTGGTTGGCGCCAAAGACGCGGTGGCCAACACGCTGGGGATGGGGGGAGACAACAACA
CTAGCTCAACCAAGGACAGTAGCACCACCGAGACGATCACCAAGAATCATCACTAG
```

SEQ ID NO: 24, Bromus inermis

```
MASNQDKASYHAGEAKARTEEKAGQVTGAAKDKACEAKDRASDAAGHATGKGQGAVEATKQK
AGEAGQKTSETAQAAKDRAAEGKDQAGSYLGQTAEAAKEKASQATGYTQDRAADAAQYTKDS
AVAGKDKTGSVLAQAGEQVKNVVVGAKDAVANTLGMGGDNNTSSTKDSSTTETITKNHH
```

SEQ ID NO: 25, Zea mays

```
ATGGCTTCCCACCAGGACAAGGCTAGCTACCAGGCCGGCGAGACCAAGGCCCGCACCGAGGA
GAAGACCGGGCAGGCGGTGGGGGCGACCAAGGACACGGCGCAGCACGCCAAGGACCGGGCGG
CGGACGCGGCGGGGCACGCGGCGGGCAAGGGCCAGGACGCCAAGGAGGCCACCAAGCAGAAG
GCGTCCGACACCGGCAGCTACCTGGGCAAGAAGACCGACGAGGCCAAGCACAAGGCCGGCGA
GACGACGGAGGCCACCAAGCACAAGGCCGGCGAGACGACGGAGGCCGCCAAGCAGAAGGCCG
GCGAGACGACGGAGGCCGCCAAGCAGAAGGCCGGCGAGACGACGGAGACGACCAAGCAGAAG
GCCGGCGAGACGACGGAGGCCGCCAGGCAGAAGGCAGCCGACGCCATGGAGGCCGCCAAGCA
GAAGGCCGCCGAGGCCGGGCAGTACGCCAAGGACACCGCCGTCTCCGGCAAGGACAAGTCCG
GCGGCGTCATCCAGCAGGCCACTGAGCAGGTGAAGAGCGCGGCGGCGGGGCGCAAGGACGCG
GTGATGAGCACGCTGGGGATGGGCGGGGACAACAAGCAGGGCGACGCCAACACCAACACCAA
CACCAACACCACCAAGGACTCCTCTACCATCACCAGGGATCACTAG
```

SEQ ID NO: 26, Zea mays

```
MASHQDKASYQAGETKARTEEKTGQAVGATKDTAQHAKDRAADAAGHAAGKGQDAKEATKQK
ASDTGSYLGKKTDEAKHKAGETTEATKHKAGETTEAAKQKAGETTEAAKQKAGETTETTKQK
AGETTEAARQKAADAMEAAKQKAAEAGQYAKDTAVSGKDKSGGVIQQATEQVKSAAAGRKDA
VMSTLGMGGDNKQGDANTNTNTNTTKDSSTITRDH
```

SEQ ID NO: 27, Brassica napus

```
ATGGCGTCTAACCAACAAAGCTACAAAGCTGGTGAAACCAGAGGCAAGACTCAGGAGAAGAC
AGGACAAGCAATGGGAGCAATGAGGGACAAGGCTGAGGAAGGCAAGGACAAGACTTCCCAGA
CGGCTCAAAAGGCCCAACAAAAGGCACAAGAGACTGCCCAGGCAGCTAAAGACAAGACATCT
CAAGCTGCCCAAACGACCCAACAAAGGCTCAAGAGACGGCACAGGCAGCGAAAGACAAGAC
ATCTCAAGCTGCCCAAACGACCCAGCAAAAGGCTCATGAGACGACCCAATCAGCAAAAGACA
AGACATCTCAAGCTGCCCAGACGGCCCAAGAAAAGCCCGGGAGACGAAGGACAAGACCGGA
AGTTACATGTCCGAGACAGGAGAAGCCATAAAGCAGAAGGCTCAAAACGCTGCTCAGTACAC
AAAGGAGACGGCTCAAGAAGCGGCTCAGTACACGAAAGAGACGGCTGAAGCCGGTAGAGACA
AGACCGGTGGGTTCTTGAGCCAGACAGGCGAGCAAGTGAAGCAGATGGCAATGGGTGCAGCT
GATGCGGTGAAGCACACTGTTGGAATGGCTACGGAGGAAGAAGACCGGGAGCATTATCCAGG
CACCACTACGACCACTACTGGTACTACTCGGACCACTGATCCGACTCATCATACTTATCAGA
GGAAGTGA
```

FIGURE 3 G

SEQ ID NO: 28, Brassica napus

MASNQQSYKAGETRGKTQEKTGQAMGAMRDKAEEGKDKTSQTAQKAQQKAQETAQAAKDKTS
QAAQTTQQKAQETAQAAKDKTSQAAQTTQQKAHETTQSAKDKTSQAAQTAQEKARETKDKTG
SYMSETGEAIKQKAQNAAQYTKETAQEAAQYTKETAEAGRDKTGGFLSQTGEQVKQMAMGAA
DAVKHTVGMATEEEDREHYPGTTTTTTGTTRTTDPTHHTYQRK

SEQ ID NO: 29, Zea mays

ATGGCTTCTCGTCAGCAGCATCCTACTAGCTACCACGCCGGCGAGACCAAGGCCCGTGCCGA
GGAGAAGACGGGTCAAGTGATGGGGGCGACGCAGGAGAAAGGGAGGGAGGCCAAGCACAAGG
CGTCCGACGCCTCCGACCGCGCCATGGGAATGGGCCACGACGCCATGGAGGCGACCAGGGAG
AAGGCGCGCGCCGCCGCGGACCGAACCATGGGGATGGGCCACGACGCCGGGGAGGCGGCCAA
GGACAGGGCGTACCGGGCCAAGGACGCGGCCTCCGGTGCCGCTGGCCGCGCCAGGGACACTG
CGTCCGACGCGGCCGGCGCTGCCGGGGACCGCGCCCGCGACGGCGCGCAGCAGACCGGGAGC
TACGTCGCGCAGACGGCCGAGGCCGCCAGGCAGAAGGCGGCCGGCGCCGCGCTGTACGCCAA
GGACACCGTGGTGGCCGGCAAGGACAAGACCGGCGCCCTCCTGCAGCAGGCAGGGGAGAAGG
TGATGAGCACGGCCGTGGGGGCCAAGGACACGGTTGTCAGCACGGCCGTGGGGGCCAAGGAC
ACGGTTGTCAGCACCGCCGTGGGAGCCAAGGACGCGATGATGAACTCGCTCGGCATGGCCGG
CGAGGACAAGGACGGCACCACCACCACCGACGCCGGCAAGGACACCAGCACCCGCAAGCCTG
GCAGGGACTATTAG

SEQ ID NO: 30, Zea mays

MASRQQHPTSYHAGETKARAEEKTGQVMGATQEKGREAKHKASDASDRAMGMGHDAMEATRE
KARAAADRTMGMGHDAGEAAKDRAYRAKDAASGAAGRARDTASDAAGAAGDRARDGAQQTGS
YVAQTAEAARQKAAGAALYAKDTVVAGKDKTGALLQQAGEKVMSTAVGAKDTVVSTAVGAKD
TVVSTAVGAKDAMMNSLGMAGEDKDGTTTTDAGKDTSTRKPGRDY

SEQ ID NO: 31, Zea mays

ATGGCTTCCCACCAGGACAAGGCTAGCTACCAGGCCGGCGAAACCAAGGCCCGCACCGAGGA
GAAGACCGGGCAGGCGGTGGGGGCGACCAAGGACACGGCGCAGCACGCCAAGGACCGGGCGG
CGGACGCGGCGGGGCACGCGGCGGGCAAGGGCCAGGACGCCAAGGAGGCCACCAAGCAGAAG
GCGTCCGACACCGGCAGCTACCTGGGCAAGAAGACCGACGAGGCCAAGCACAAGGCCGGCGA
GACGACGGAGGCCACCAAGCAGAAGGCCGGCGAGACGACGGAGGCGACCAAGCAGAAGGCCG
GCGAGACGACGGAGGCCGCCAGGCAGAAGGCAGCCGACGCCATGGAGGCAGCCAAGCAGAAG
GCCGCCGAGGCCGGGCAGTACGCCAAGGACACCGCCGTCTCCGGCAAGGACAAGTCCGGCGG
CGTCATCCAGCAGGCCACTGAGCAGGTGAAGAGCGCGGCGGCGGGCGCCAAGGACGCGGTGA
TGAGCACGCTGGGGATGGGCGGGGACGACAAGCAGGGCGACGCCAACACCAACACCAACAAG
GACTCCTCTACCATCACCAGGGATCACTAG

FIGURE 3 H

SEQ ID NO: 32, Zea mays

MASHQDKASYQAGETKARTEEKTGQAVGATKDTAQHAKDRAADAAGHAAGKGQDAKEATKQK
ASDTGSYLGKKTDEAKHKAGETTEATKQKAGETTEATKQKAGETTEAARQKAADAMEAAKQK
AAEAGQYAKDTAVSGKDKSGGVIQQATEQVKSAAAGAKDAVMSTLGMGGDDKQGDANTNTNK
DSSTITRDH

SEQ ID NO: 33, Triticum aestivum

ATGGCCTCCAACCAGAACCAGGCCAGCTACCACGCCGGCGAGACCAAGGCCCGCACCGAGGA
GAAGACCGGGCAGGTGATGGGCGCGACCAAGGACAAGGCGGGGCAGACCACGGAGGCCACCA
AGCAGAAGGCCGGACAGACCACCGAGGCCACCAAGCAGAAGGCCGGCGAGACGGCCGAGGCA
ACGAAGCAGAAGGCCGGTCAGGCCACGGAGGCCACGAAGCAGAAGGCCGGCGAGACGGCCGA
GGCCACCAAGCAGAAGGCCGCCGAGGCCAAGGACAAGACTGCGCAGACGGCGCAGGCGGCCA
AGGAGCGCGCCGCCGAGACCAAGGACCAGACCGGCAGCTACCTCGGCGAGAAGACAGAGATG
GCCAAGCAGAAGGCCGCCGAGACGACCGAGGCTGCCAAGCAGAAGGCCTCGGAGACGGCGCA
GTACACCAAGGAGTCCGTCGCCGGCAAGGACAAGACCGGCAGCGTCCTCCAGCAGGCCGGCG
AGACGGTGGTGAACGCCGTGGATGGCGCCAAGGACGCCGTGGCCAACACGCTGGGCAATGGG
CCGGACAACGCCACCAAGGACACCTCCACCGGCGCCACCACGAAGGACACCACCACCACCAC
CACCAGGAATCACTAG

SEQ ID NO: 34, Triticum aestivum

MASNQNQASYHAGETKARTEEKTGQVMGATKDKAGQTTEATKQKAGQTTEATKQKAGETAEA
TKQKAGQATEATKQKAGETAEATKQKAAEAKDKTAQTAQAAKERAAETKDQTGSYLGEKTEM
AKQKAAETTEAAKQKASETAQYTKESVAGKDKTGSVLQQAGETVVNAVDGAKDAVANTLGNG
PDNATKDTSTGATTKDTTTTTRNH

SEQ ID NO: 35, Oryza sativa, homologue of SEQ ID NO: 14

MASQQERASYHAGETKARAEEKTGRMMGTAQEKAREAKDTASDAAGRAMGRGHGAKEATKEK
AYETKDATKEKAYEAKDAASDATGRAMDKGRAAGATRDKAYDAKDRAADTAQSAADRARDGA
GQTGSYIGQTAEAAKQKAAGAAQYAKETAIAGKDKTGAVLQQAGEQVKSVAVGAKDAVMYTL
GMSGDNKNNAAAGKDTSTYKPGTGSDYQ

SEQ ID NO: 36, Triticum aestivum, homologue of SEQ ID NO: 34

MASNQNQASYAAGETKARTEEKTGQMMDKAGQATEATKQKAGEAKDKTAQTAQAAKDRAAES
KDQTGSFLGEKTEAAKQKTAEATDAAKQKASETAQYAQERSSDAAQYTKESAVAGKDKTGSV
LQQAGETVVSAVVGAKDAVANTLGMGGDNTNTAKDSTTEKITRDH

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 1. SEQID02 | | 99.5 | 97.5 | 98.5 | 48.7 | 48.3 | 48.3 | 48.5 | 59.2 | 54.1 | 42.9 | 43.6 | 56.9 | 58.3 | 48.5 | 54.5 |
| 2. SEQID08 | 99.5 | | 97.0 | 98.0 | 48.7 | 48.3 | 48.3 | 48.5 | 59.2 | 54.1 | 42.4 | 42.9 | 56.9 | 57.8 | 48.5 | 54.0 |
| 3. SEQID10 | 98.5 | 98.0 | | 96.0 | 50.7 | 50.2 | 50.2 | 48.0 | 58.2 | 53.2 | 42.0 | 44.5 | 56.4 | 59.2 | 48.0 | 54.5 |
| 4. SEQID12 | 99.5 | 99.0 | 98.0 | | 48.7 | 48.3 | 48.3 | 48.5 | 58.7 | 53.6 | 43.3 | 43.2 | 56.4 | 58.3 | 48.5 | 54.5 |
| 5. SEQID14 | 64.7 | 64.7 | 63.3 | 63.3 | | 99.5 | 99.5 | 99.1 | 49.1 | 47.4 | 39.9 | 56.4 | 48.2 | 46.5 | 99.1 | 45.0 |
| 6. SEQID16 | 64.2 | 64.2 | 62.8 | 62.8 | 99.5 | | 100.0 | 99.5 | 49.6 | 47.8 | 39.9 | 56.8 | 48.6 | 47.0 | 99.5 | 45.4 |
| 7. SEQID18 | 64.2 | 64.2 | 62.8 | 62.8 | 99.5 | 100.0 | | 99.5 | 49.6 | 47.8 | 39.9 | 56.8 | 48.6 | 47.0 | 99.5 | 45.4 |
| 8. SEQID20 | 64.5 | 64.5 | 63.6 | 63.1 | 99.1 | 99.5 | 99.5 | | 49.8 | 48.9 | 40.1 | 54.6 | 49.3 | 47.2 | 100.0 | 45.3 |
| 9. SEQID24 | 71.5 | 71.5 | 70.5 | 70.0 | 64.7 | 65.1 | 65.1 | 65.4 | | 49.8 | 40.3 | 40.1 | 54.8 | 54.6 | 49.8 | 60.8 |
| 10. SEQID26 | 66.5 | 66.5 | 65.2 | 65.6 | 64.3 | 64.7 | 64.7 | 63.3 | 61.5 | | 40.3 | 41.1 | 86.9 | 52.1 | 48.9 | 46.6 |
| 11. SEQID28 | 56.8 | 55.5 | 55.9 | 56.3 | 58.1 | 58.5 | 58.5 | 58.5 | 52.4 | 56.8 | | 35.8 | 39.0 | 47.7 | 40.1 | 37.7 |
| 12. SEQID30 | 56.7 | 56.7 | 56.7 | 56.3 | 67.5 | 68.0 | 68.0 | 68.4 | 54.1 | 57.1 | 54.5 | | 42.9 | 41.2 | 54.6 | 38.5 |
| 13. SEQID32 | 69.0 | 69.0 | 68.5 | 68.0 | 63.3 | 63.7 | 63.7 | 64.0 | 69.2 | 87.1 | 53.3 | 55.0 | | 49.6 | 49.3 | 49.7 |
| 14. SEQID34 | 73.0 | 73.0 | 73.0 | 71.6 | 63.7 | 64.2 | 64.2 | 64.5 | 66.8 | 67.9 | 60.7 | 57.6 | 65.9 | | 47.2 | 60.3 |
| 15. SEQID35 | 64.5 | 64.5 | 63.6 | 63.1 | 99.1 | 99.5 | 99.5 | 100.0 | 65.4 | 63.3 | 58.5 | 68.4 | 64.0 | 64.5 | | 45.3 |
| 16. SEQID36 | 65.0 | 64.5 | 64.5 | 64.0 | 56.3 | 56.7 | 56.7 | 57.0 | 75.4 | 57.9 | 48.9 | 51.1 | 64.6 | 67.8 | 57.0 | |

FIGURE 4

SEQUENCE LISTING

```
<160> NUMBER OF SEQ ID NOS: 36

<210> SEQ ID NO 1
<211> LENGTH: 603
<212> TYPE: DNA
<213> ORGANISM: Oryza sativa

<400> SEQUENCE: 1
atggcttccc accaggacca ggctagctac cgcgccggcg agaccaaggc ccacaccgag      60
gagaaggcgg ggcaggtgat gggggcgagc aaggacaagg cgagcgaggc gaaggacagg     120
gcgtcggagg cggcggggca cgccgccggc aagggggcag ataccaagga ggcgacgaag     180
gagaaggcgc aggcggcgaa ggagagggcg tcggagacgg cgcaggcggc gaaggacaag     240
acctccagca cgtcgcaggc ggcgagggac aaagccgccg agagcaagga ccagaccggc     300
ggcttcctcg gcgagaagac cgagcaggcc aagcagaagg ccgccgagac cgctggcgcc     360
gccaagcaga agaccgccga gacggcgcag tacaccaagg actctgccat cgccggcaag     420
gacaagaccg gcagcgtcct ccaacaggcg agtgagcagg tgaagagcac ggtggtcggc     480
gccaaggacg cggtgatgag cacgctgggg atgaccgaag acgaggccgg caccgacgac     540
ggcgccaaca aggacacctc tgccaccgcc gccgccacgg agacgacggc gagggatcac     600
tag                                                                   603

<210> SEQ ID NO 2
<211> LENGTH: 200
<212> TYPE: PRT
<213> ORGANISM: Oryza sativa

<400> SEQUENCE: 2

Met Ala Ser His Gln Asp Gln Ala Ser Tyr Arg Ala Gly Glu Thr Lys
  1               5                  10                  15

Ala His Thr Glu Glu Lys Ala Gly Gln Val Met Gly Ala Ser Lys Asp
             20                  25                  30

Lys Ala Ser Glu Ala Lys Asp Arg Ala Ser Glu Ala Ala Gly His Ala
         35                  40                  45

Ala Gly Lys Gly Gln Asp Thr Lys Glu Ala Thr Lys Glu Lys Ala Gln
     50                  55                  60
```

-continued

```
Ala Ala Lys Glu Arg Ala Ser Glu Thr Ala Gln Ala Ala Lys Asp Lys
 65                  70                  75                  80

Thr Ser Ser Thr Ser Gln Ala Ala Arg Asp Lys Ala Ala Glu Ser Lys
                 85                  90                  95

Asp Gln Thr Gly Gly Phe Leu Gly Glu Lys Thr Glu Gln Ala Lys Gln
            100                 105                 110

Lys Ala Ala Glu Thr Ala Gly Ala Ala Lys Gln Lys Thr Ala Glu Thr
        115                 120                 125

Ala Gln Tyr Thr Lys Asp Ser Ala Ile Ala Gly Lys Asp Lys Thr Gly
    130                 135                 140

Ser Val Leu Gln Gln Ala Ser Glu Gln Val Lys Ser Thr Val Val Gly
145                 150                 155                 160

Ala Lys Asp Ala Val Met Ser Thr Leu Gly Met Thr Glu Asp Glu Ala
                165                 170                 175

Gly Thr Asp Asp Gly Ala Asn Lys Asp Thr Ser Ala Thr Ala Ala Ala
            180                 185                 190

Thr Glu Thr Thr Ala Arg Asp His
        195                 200

<210> SEQ ID NO 3
<211> LENGTH: 11
<212> TYPE: PRT
<213> ORGANISM: Artificial sequence
<220> FEATURE:
<223> OTHER INFORMATION: OsLEA3a consensus signature sequence
<220> FEATURE:
<221> NAME/KEY: Misc_Feature
<222> LOCATION: (2)..(2)
<223> OTHER INFORMATION: Xaa at position 2 is Ser, Thr, Ala, or Lys
<220> FEATURE:
<221> NAME/KEY: Misc_Feature
<222> LOCATION: (3)..(3)
<223> OTHER INFORMATION: Xaa at position 3 is Gln, Glu, or Asp
<220> FEATURE:
<221> NAME/KEY: Misc_Feature
<222> LOCATION: (5)..(5)
<223> OTHER INFORMATION: Xaa at position 5 is Ala or Thr
<220> FEATURE:
<221> NAME/KEY: Misc_Feature
<222> LOCATION: (6)..(6)
<223> OTHER INFORMATION: Xaa at position 6 is Arg or Lys
<220> FEATURE:
<221> NAME/KEY: Misc_Feature
<222> LOCATION: (7)..(7)
<223> OTHER INFORMATION: Xaa at position 7 is Asp, Gln, or Glu
<220> FEATURE:
<221> NAME/KEY: Misc_Feature
<222> LOCATION: (8)..(8)
<223> OTHER INFORMATION: Xaa at position 8 is Lys or Arg
<220> FEATURE:
<221> NAME/KEY: VARIANT
<222> LOCATION: (10)..(10)
<223> OTHER INFORMATION: Xaa at position 10 is Ala, Gly, or Tyr
<220> FEATURE:
<221> NAME/KEY: VARIANT
<222> LOCATION: (11)..(11)
<223> OTHER INFORMATION: Xaa at position 11 is Glu or Gly

<400> SEQUENCE: 3

Thr Xaa Xaa Ala Xaa Xaa Xaa Xaa Ala Xaa Xaa
 1               5                  10

<210> SEQ ID NO 4
<211> LENGTH: 52
<212> TYPE: DNA
<213> ORGANISM: Artificial sequence
<220> FEATURE:
<223> OTHER INFORMATION: primer: prm06118
```

```
<400> SEQUENCE: 4
ggggacaagt tgtacaaaa aagcaggctt aaacaatggc ttcccaccag ga            52

<210> SEQ ID NO 5
<211> LENGTH: 50
<212> TYPE: DNA
<213> ORGANISM: Artificial sequence
<220> FEATURE:
<223> OTHER INFORMATION: primer: prm06119

<400> SEQUENCE: 5
ggggaccact tgtacaaga aagctgggta aatcattcac ggcgtctagt              50

<210> SEQ ID NO 6
<211> LENGTH: 2193
<212> TYPE: DNA
<213> ORGANISM: Oryza sativa

<400> SEQUENCE: 6
aatccgaaaa gtttctgcac cgttttcacc ccctaactaa caatataggg aacgtgtgct    60
aaatataaaa tgagacctta tatatgtagc gctgataact agaactatgc aagaaaaact   120
catccaccta ctttagtggc aatcgggcta ataaaaaag agtcgctaca ctagtttcgt    180
tttccttagt aattaagtgg gaaaatgaaa tcattattgc ttagaatata cgttcacatc   240
tctgtcatga agttaaatta ttcgaggtag ccataattgt catcaaactc ttcttgaata   300
aaaaaatctt tctagctgaa ctcaatgggt aaagagagag attttttta aaaaaataga   360 atgaagatat tctgaacgta ttggcaaaga tttaaacata taattatata attttatagt   420
ttgtgcattc gtcatatcgc acatcattaa ggacatgtct tactccatcc caattttat    480 ttagtaatta aagacaattg acttatttt attatttatc ttttttcgat tagatgcaag   540
gtacttacgc acacactttg tgctcatgtg catgtgtgag tgcacctcct caatacacgt   600
tcaactagca acacatctct aatatcactc gcctatttaa tacatttagg tagcaatatc   660
tgaattcaag cactccacca tcaccagacc acttttaata atatctaaaa tacaaaaaat   720
aattttacag aatagcatga aaagtatgaa acgaactatt taggttttc acatacaaaa   780 aaaaaaagaa ttttgctcgt gcgcgagcgc caatctccca tattgggcac acaggcaaca   840
acagagtggc tgcccacaga acaacccaca aaaacgatg atctaacgga ggacagcaag   900
tccgcaacaa cctttttaaca gcaggctttg cggccaggag agaggaggag aggcaaagaa   960
aaccaagcat cctcctcctc ccatctataa attcctcccc ccttttcccc tctctatata  1020
ggaggcatcc aagccaagaa gagggagagc accaaggaca cgcgactagc agaagccgag  1080
cgaccgcctt cttcgatcca tatcttccgg tcgagttctt ggtcgatctc ttccctcctc  1140
cacctcctcc tcacagggta tgtgcccttc ggttgttctt ggatttattg ttctaggttg  1200
tgtagtacgg gcgttgatgt taggaaaggg gatctgtatc tgtgatgatt cctgttcttg  1260
gatttgggat agaggggttc ttgatgttgc atgttatcgg ttcggtttga ttagtagtat  1320
ggttttcaat cgtctggaga gctctatgga aatgaaatgg tttagggtac ggaatcttgc  1380
gattttgtga gtacctttg tttgaggtaa aatcagagca ccggtgattt tgcttggtgt   1440
aataaaagta cggttgtttg gtcctcgatt ctggtagtga tgcttctcga tttgacgaag  1500
ctatcctttg tttattccct attgaacaaa aataatccaa ctttgaagac ggtcccgttg  1560
atgagattga atgattgatt cttaagcctg tccaaaattt cgcagctggc ttgtttagat  1620
acagtagtcc ccatcacgaa attcatggaa acagttataa tcctcaggaa cagggggattc  1680
```

-continued

```
cctgttcttc cgatttgctt tagtcccaga attttttttc ccaaatatct taaaaagtca    1740
ctttctggtt cagttcaatg aattgattgc tacaaataat gcttttatag cgttatccta    1800
gctgtagttc agttaatagg taatacccct atagtttagt caggagaaga acttatccga    1860
tttctgatct ccattttaa ttatatgaaa tgaactgtag cataagcagt attcatttgg    1920
attatttttt ttattagctc tcaccccttc attattctga gctgaaagtc tggcatgaac    1980
tgtcctcaat tttgttttca aattcacatc gattatctat gcattatcct cttgtatcta    2040
cctgtagaag tttctttttg gttattcctt gactgcttga ttacagaaag aaatttatga    2100
agctgtaatc gggatagtta tactgcttgt tcttatgatt catttccttt gtgcagttct    2160
tggtgtagct tgccactttc accagcaaag ttc                                  2193
```

<210> SEQ ID NO 7
<211> LENGTH: 968
<212> TYPE: DNA
<213> ORGANISM: Oryza sativa

<400> SEQUENCE: 7

```
agccagtgca atctgatcg atcaaggtaa tcgagcaaaa tccatcagag ttctaacatt      60
cgcgcgtgaa tttcgaggtt aattttgaa gcttaggatc aatggcttcc caccaggacc     120
aggctagcta ccgcgccggc gagaccaagg cccacaccga ggagaaggcg ggcaggtga     180 tgggggcgag caaggacaag gcgagcgagg cgaaggacag ggcgtcggag gcggcgggc     240 acgccgccgg caaggggcag gataccaagg aggcgacgaa ggagaaggcg caggcggcga    300
aggagagggc gtcggagacg gcgcaggcgg cgaaggacaa gacctccagc acgtcgcagg    360
cggcgaggga caaagccgcc gagagcaagg accagaccgg cggcttcctc ggcgagaaga    420
ccgagcaggc caagcagaag gccgccgaga ccgctggcgc cgccaagcag aagaccgccg    480
agacggcgca gtacaccaag gactctgcca tcgccggcaa ggacaagacc ggcagcgtcc    540
tccaacaggc gagtgagcag gtgaagagca cggtggtcgg cgccaaggac gcggtgatga    600
gcacgctggg gatgaccgaa gacgaggccg caccgacga cggcgccaac aaggacaccc    660
ctgccaccgc cgccgccgcg gagacgacgg cgagggatca ctagacgccg tgaatgattt    720
ccctttgggt ctatttatgt atgttttcac ttcaaattcg gtgcaagttt gaatttgttt    780
ttgtgtcgtt ttgagtctgt atcgatgctg tatgaagtgg tggtcgtcgc aggggaggat    840
ttctgacggg tgtgggtgat gtgtactgat gatgttcagt tgttttcgtc agagtttctc    900
gtctgtgttc tgtttattat ggcgtaacaa taataaagt ttgggcctaa agcccgcatt     960
tgtgggttt                                                            968
```

<210> SEQ ID NO 8
<211> LENGTH: 200
<212> TYPE: PRT
<213> ORGANISM: Oryza sativa

<400> SEQUENCE: 8

```
Met Ala Ser His Gln Asp Gln Ala Ser Tyr Arg Ala Gly Glu Thr Lys
1               5                   10                  15

Ala His Thr Glu Glu Lys Ala Gly Gln Val Met Gly Ala Ser Lys Asp
            20                  25                  30

Lys Ala Ser Glu Ala Lys Asp Arg Ala Ser Glu Ala Ala Gly His Ala
        35                  40                  45

Ala Gly Lys Gly Gln Asp Thr Lys Glu Ala Thr Lys Glu Lys Ala Gln
    50                  55                  60
```

```
Ala Ala Lys Glu Arg Ala Ser Glu Thr Ala Gln Ala Ala Lys Asp Lys
 65                  70                  75                  80

Thr Ser Ser Thr Ser Gln Ala Ala Arg Asp Lys Ala Ala Glu Ser Lys
                 85                  90                  95

Asp Gln Thr Gly Gly Phe Leu Gly Glu Lys Thr Glu Gln Ala Lys Gln
            100                 105                 110

Lys Ala Ala Glu Thr Ala Gly Ala Ala Lys Gln Lys Thr Ala Glu Thr
        115                 120                 125

Ala Gln Tyr Thr Lys Asp Ser Ala Ile Ala Gly Lys Asp Lys Thr Gly
    130                 135                 140

Ser Val Leu Gln Gln Ala Ser Glu Gln Val Lys Ser Thr Val Val Gly
145                 150                 155                 160

Ala Lys Asp Ala Val Met Ser Thr Leu Gly Met Thr Glu Asp Glu Ala
                165                 170                 175

Gly Thr Asp Asp Gly Ala Asn Lys Asp Thr Ser Ala Thr Ala Ala Ala
            180                 185                 190

Ala Glu Thr Thr Ala Arg Asp His
        195                 200

<210> SEQ ID NO 9
<211> LENGTH: 966
<212> TYPE: DNA
<213> ORGANISM: Oryza sativa

<400> SEQUENCE: 9
gatcaagata atcgagcaaa atccatcaga gttctaacat tcgcgcgtga atttcgaggt    60 taattttga agcttaggat caatggcttc ccaccaggac caggctagct accgcgccgg    120
cgagaccaag gcccacaccg aggagaaggc ggtgcaggtg atgggggcga gcaaggacaa    180
ggcgagcgag gcgaaggaca gagcgtcgga ggcggcggtg cacgccgccg gcaaggggca    240
ggataccaag gaggcgacga aggagaaggc gcaggcggcg aaggagaggg cgtcggagac    300
ggcgcaggcg gcgaaggaca agacctccgg cacggcgcag gcggcgaggg acaaagccgc    360
cgagagcaag gaccagaccg gcggcttcct cggcgagaag accgagcagg ccaagcagaa    420
ggccgccgag accgctggcg ccgccaagca gaagaccgcc gagacggcgc agtacaccaa    480
ggactctgcc atcgccggca aggacaagac cggcagcgtc ctccaacagg cgagtgagca    540
ggtgaagagc acggtggtcg gcgccaagga cgcggtgatg agcacgctgg ggatgaccga    600
agacaaggcc ggcaccgacg acggcgccaa caaggacacc tctgccaccg ccgccgccac    660
ggagacgacg gcgagggatc actagacgcc gtgaatgatt tcccttttggg tctatttatg    720 tatgttttca cttcaaattc ggtgcaagtt tgaatttgtt tttgtgtcgt tttgagtctg    780
tatcgatgct gtatgaagtg gtggtcgtcg caggggagga tttctgacgg gtgtgggtga    840
tgtgtactga tgatgttcag ttgtttttcgt cagagtttct cgtctgtgtt ctgtttatta    900
tggcgtaaca ataataaaag tttgggccta agcccgcat ttgtggttta aaaaaaaaa    960 aaaaaa                                                               966

<210> SEQ ID NO 10
<211> LENGTH: 200
<212> TYPE: PRT
<213> ORGANISM: Oryza sativa

<400> SEQUENCE: 10

Met Ala Ser His Gln Asp Gln Ala Ser Tyr Arg Ala Gly Glu Thr Lys
  1               5                  10                  15
```

```
Ala His Thr Glu Glu Lys Ala Val Gln Val Met Gly Ala Ser Lys Asp
         20                  25                  30

Lys Ala Ser Glu Ala Lys Asp Arg Ala Ser Glu Ala Ala Val His Ala
     35                  40                  45

Ala Gly Lys Gly Gln Asp Thr Lys Glu Ala Thr Lys Glu Lys Ala Gln
 50                  55                  60

Ala Ala Lys Glu Arg Ala Ser Glu Thr Ala Gln Ala Ala Lys Asp Lys
 65                  70                  75                  80

Thr Ser Gly Thr Ala Gln Ala Ala Arg Asp Lys Ala Ala Glu Ser Lys
             85                  90                  95

Asp Gln Thr Gly Gly Phe Leu Gly Glu Lys Thr Glu Gln Ala Lys Gln
            100                 105                 110

Lys Ala Ala Glu Thr Ala Gly Ala Ala Lys Gln Lys Thr Ala Glu Thr
            115                 120                 125

Ala Gln Tyr Thr Lys Asp Ser Ala Ile Ala Gly Lys Asp Lys Thr Gly
        130                 135                 140

Ser Val Leu Gln Gln Ala Ser Glu Gln Val Lys Ser Thr Val Val Gly
145                 150                 155                 160

Ala Lys Asp Ala Val Met Ser Thr Leu Gly Met Thr Glu Asp Lys Ala
                165                 170                 175

Gly Thr Asp Asp Gly Ala Asn Lys Asp Thr Ser Ala Thr Ala Ala Ala
            180                 185                 190

Thr Glu Thr Thr Ala Arg Asp His
            195                 200

<210> SEQ ID NO 11
<211> LENGTH: 603
<212> TYPE: DNA
<213> ORGANISM: Oryza sativa

<400> SEQUENCE: 11
atggcttccc accaggacca ggctagctac cgcgccggcg agaccaaggc ccacaccgag      60
gagaaggcgg ggcaggtgat gggggcgagc aaggacaagg cgagcgaggc gaaggacagg     120
gcgtcggagg cggcggggca cgccgccggc aaggggcaga taccaaggaa ggcgacgaag     180
gacaaggcgc aggcggcgaa ggatagggcg tcggagacgg cgcaggcggc gaaggacaag     240
acctccagca cgtcgcaggc ggcgagggac aaagccgccg agagcaagga ccagaccggc     300
ggcttcctcg gcgagaagac cgagcaggcc aagcagaagg ccgccgagac cgctggcgcc     360
gccaagcaga aaaccccgga cggcgcag tacaccaagg actctgccat cgccggcaag     420
gacaagaccg gcagcgtcct ccaacaggcg agtgagcagg tgaagagcac ggtggtcggc     480
gccaaggacg cggtgatgag cacgctgggg atgaccgaag acgaggccgg caccgacgac     540
ggcgccaaca aggacaccct tgccaccgcc gccgccacgg agacgacggc gagggatcac     600
tag                                                                  603

<210> SEQ ID NO 12
<211> LENGTH: 200
<212> TYPE: PRT
<213> ORGANISM: Oryza sativa

<400> SEQUENCE: 12

Met Ala Ser His Gln Asp Gln Ala Ser Tyr Arg Ala Gly Glu Thr Lys
 1               5                  10                  15

Ala His Thr Glu Glu Lys Ala Gly Gln Val Met Gly Ala Ser Lys Asp
         20                  25                  30
```

```
Lys Ala Ser Glu Ala Lys Asp Arg Ala Ser Glu Ala Ala Gly His Ala
        35                  40                  45
Ala Gly Lys Gly Gln Asp Thr Lys Glu Ala Thr Lys Asp Lys Ala Gln
 50                  55                  60
Ala Ala Lys Asp Arg Ala Ser Glu Thr Ala Gln Ala Lys Asp Lys
 65                  70                  75                  80
Thr Ser Ser Thr Ser Gln Ala Ala Arg Asp Lys Ala Ala Glu Ser Lys
                 85                  90                  95
Asp Gln Thr Gly Gly Phe Leu Gly Glu Lys Thr Glu Gln Ala Lys Gln
            100                 105                 110
Lys Ala Ala Glu Thr Ala Gly Ala Ala Lys Gln Lys Thr Pro Glu Thr
        115                 120                 125
Ala Gln Tyr Thr Lys Asp Ser Ala Ile Ala Gly Lys Asp Lys Thr Gly
130                 135                 140
Ser Val Leu Gln Gln Ala Ser Glu Gln Val Lys Ser Thr Val Val Gly
145                 150                 155                 160
Ala Lys Asp Ala Val Met Ser Thr Leu Gly Met Thr Glu Asp Glu Ala
                165                 170                 175
Gly Thr Asp Asp Gly Ala Asn Lys Asp Thr Ser Ala Thr Ala Ala Ala
            180                 185                 190
Thr Glu Thr Thr Ala Arg Asp His
        195                 200

<210> SEQ ID NO 13
<211> LENGTH: 996
<212> TYPE: DNA
<213> ORGANISM: Oryza sativa

<400> SEQUENCE: 13
gacaaggcaa gaggcaagag caagagcat ccgtattaac cagccttttg agacttgaga      60
gtgtgtgtga ctcgatccag cgtagtttca gttcgtgtgt tggtgagtga ttccagccaa    120
gtttgcgatg gcttctcagc aggaacgggc tagctaccac gccggcgaga ccaaggccca    180
cgccgaggag aagacggggc gcatgatggg cacggcgcag agaaggcgc gggaggccaa     240
ggacacggcg tccgacgccg cggggcgcgc gatgggcagg ggacacggcg ccaaggaggc    300
gaccaaggag aaggcgtacg agaccaagga cgcgaccaag gagaaggcgt acgaggcaaa    360
ggacgcggcc tccgacgcca ccggccgcgc catggacaag ggccgcggcg ccgcgggcgc    420
cacgagggac aaggcgtacg atgccaagga cagggcggct gacacggcgc agtccgccgc    480
cgaccgcgcc cgcgacggcg ccgggcagac cgggagctac attggacaga ccgccgaggc    540
cgccaagcag aaagcggccg cgccgcgca gtacgccaag gagaccgcga tcgccggcaa    600
ggacaagacc ggcgccgtgc tccagcaggc aggggagcag gtgaagagcg tggcggtggg    660
ggcgaaggac gcggtgatgt acacgctcgg gatgtcaggc gataacaaga acaacgccgc    720
tgccggcaag gacaccagca cctacaagcc tggaactggg agtgactacc agtaatacgg    780
tataagaagc atgtgtcgtc tttggcactg atgccaaagt gtacgtgttg tatcctcttt    840
tttaagttc agctcgactt cgacgtgttc ggtgtcacac tttggttttt cagttgtgct    900
caactgttca tgtttctggt tccatggagg gccagtgtgg aggtcaatgt ttaagctttc    960
gttttaaaat ctgataataa agttggttaa gacctg                              996

<210> SEQ ID NO 14
<211> LENGTH: 215
<212> TYPE: PRT
<213> ORGANISM: Oryza sativa
```

<400> SEQUENCE: 14

```
Met Ala Ser Gln Gln Glu Arg Ala Ser Tyr His Ala Gly Glu Thr Lys
1               5                   10                  15
Ala His Ala Glu Glu Lys Thr Gly Arg Met Met Gly Thr Ala Gln Glu
            20                  25                  30
Lys Ala Arg Glu Ala Lys Asp Thr Ala Ser Asp Ala Ala Gly Arg Ala
        35                  40                  45
Met Gly Arg Gly His Gly Ala Lys Glu Ala Thr Lys Glu Lys Ala Tyr
    50                  55                  60
Glu Thr Lys Asp Ala Thr Lys Glu Lys Ala Tyr Glu Ala Lys Asp Ala
65                  70                  75                  80
Ala Ser Asp Ala Thr Gly Arg Ala Met Asp Lys Gly Arg Gly Ala Ala
                85                  90                  95
Gly Ala Thr Arg Asp Lys Ala Tyr Asp Ala Lys Asp Arg Ala Ala Asp
            100                 105                 110
Thr Ala Gln Ser Ala Ala Asp Arg Ala Arg Asp Gly Ala Gly Gln Thr
        115                 120                 125
Gly Ser Tyr Ile Gly Gln Thr Ala Glu Ala Ala Lys Gln Lys Ala Ala
    130                 135                 140
Gly Ala Ala Gln Tyr Ala Lys Glu Thr Ala Ile Ala Gly Lys Asp Lys
145                 150                 155                 160
Thr Gly Ala Val Leu Gln Gln Ala Gly Glu Gln Val Lys Ser Val Ala
                165                 170                 175
Val Gly Ala Lys Asp Ala Val Met Tyr Thr Leu Gly Met Ser Gly Asp
            180                 185                 190
Asn Lys Asn Asn Ala Ala Ala Gly Lys Asp Thr Ser Thr Tyr Lys Pro
        195                 200                 205
Gly Thr Gly Ser Asp Tyr Gln
    210                 215
```

<210> SEQ ID NO 15
<211> LENGTH: 1006
<212> TYPE: DNA
<213> ORGANISM: Oryza sativa

<400> SEQUENCE: 15

| | | | | | |
|---|---|---|---|---|---|
| gtcacaaggc | aagaggcaag | aggcaagagc | atccgtatta | accagccttt | tgagacttga | 60 |
| gagtgtgtgt | gactcgatcc | agcgtagttt | cagttcgtgt | gttggtgagt | gattccagcc | 120 |
| aagtttgcga | tggcttctca | gcaggaacgg | gctagctacc | acgccggcga | gaccaaggcc | 180 |
| cgcgccgagg | agaagacggg | cgcatgatg | ggcacggcgc | aggagaaggc | gcggaggcc | 240 |
| aaggacacgg | cgtccgacgc | cgcggggcgc | gcgatgggca | ggggacacgg | cgccaaggag | 300 |
| gcgaccaagg | agaaggcgta | cgagaccaag | gacgcgacca | aggagaaggc | gtacgaggca | 360 |
| aaggacgcgg | cctccgacgc | caccggccgc | gccatggaca | agggccgcgg | cgccgcgggc | 420 |
| gccacgaggg | acaaggcgta | cgatgccaag | gacagggcgg | ctgacacggc | gcagtccgcc | 480 |
| gccgaccgcg | cccgcgacgg | cgccgggcag | accgggagct | acattggaca | gaccgccgag | 540 |
| gccgccaagc | agaaagcggc | cggcgccgcg | cagtacgcca | aggagaccgc | gatcgccggc | 600 |
| aaggacaaga | ccggcgccgt | gctccagcag | gcagggagc | aggtgaagag | cgtggcggtg | 660 |
| ggggcgaagg | acgcggtgat | gtacacgctc | gggatgtcag | gcgataacaa | gaacaacgcc | 720 |
| gctgccggca | aggacaccag | cacctacaag | cctggaactg | ggagtgacta | ccagtaatac | 780 |
| ggtataagaa | gcatgtgtcg | tctttggcac | tgatgccaaa | gtgtacgtgt | tgtatcctct | 840 |

```
tttttaagtt tcagctcgac ttcgacgtgt tcggtgtcac actttggttt ttcagttgtg    900
ctcaactgtt catgtttctg gttccatgga gggccagtgt ggaggtcaat gtttaagctt    960
tcgttttaaa atctgataat aaagttggtt aagacctgaa agcgtt                   1006
```

```
<210> SEQ ID NO 16
<211> LENGTH: 215
<212> TYPE: PRT
<213> ORGANISM: Oryza sativa

<400> SEQUENCE: 16

Met Ala Ser Gln Gln Glu Arg Ala Ser Tyr His Ala Gly Glu Thr Lys
1               5                   10                  15

Ala Arg Ala Glu Glu Lys Thr Gly Arg Met Met Gly Thr Ala Gln Glu
            20                  25                  30

Lys Ala Arg Glu Ala Lys Asp Thr Ala Ser Asp Ala Ala Gly Arg Ala
        35                  40                  45

Met Gly Arg Gly His Gly Ala Lys Glu Ala Thr Lys Glu Lys Ala Tyr
    50                  55                  60

Glu Thr Lys Asp Ala Thr Lys Glu Lys Ala Tyr Glu Ala Lys Asp Ala
65                  70                  75                  80

Ala Ser Asp Ala Thr Gly Arg Ala Met Asp Lys Gly Arg Gly Ala Ala
                85                  90                  95

Gly Ala Thr Arg Asp Lys Ala Tyr Asp Ala Lys Asp Arg Ala Ala Asp
            100                 105                 110

Thr Ala Gln Ser Ala Ala Asp Arg Ala Arg Asp Gly Ala Gly Gln Thr
        115                 120                 125

Gly Ser Tyr Ile Gly Gln Thr Ala Glu Ala Ala Lys Gln Lys Ala Ala
    130                 135                 140

Gly Ala Ala Gln Tyr Ala Lys Glu Thr Ala Ile Ala Gly Lys Asp Lys
145                 150                 155                 160

Thr Gly Ala Val Leu Gln Gln Ala Gly Glu Gln Val Lys Ser Val Ala
                165                 170                 175

Val Gly Ala Lys Asp Ala Val Met Tyr Thr Leu Gly Met Ser Gly Asp
            180                 185                 190

Asn Lys Asn Asn Ala Ala Ala Gly Lys Asp Thr Ser Thr Tyr Lys Pro
        195                 200                 205

Gly Thr Gly Ser Asp Tyr Gln
    210                 215
```

```
<210> SEQ ID NO 17
<211> LENGTH: 648
<212> TYPE: DNA
<213> ORGANISM: Oryza sativa

<400> SEQUENCE: 17
atggcttctc agcaggaacg ggctagctac cacgccggcg agaccaaggc ccgcgccgag     60
gagaagacgg ggcgcatgat gggcacggcg caggagaagg cgcgggaggc caaggacacg    120
gcgtccgacg ccgcggggcg cgcgatgggc agggacacgc gccaaggag gcgaccaag     180 gagaaggcgt acgagaccaa ggacgcgacc aaggagaagg cgtacgaggc aaaggacgcg    240
gcctccgacg ccaccggccg cgccatggac aagggccgcg gcgccgcggg cgccacgagg    300
gacaaggcgt acgatgccaa ggacagggcg gctgacacgg cgcagtccgc cgccgaccgc    360
gcccgcgacg gcgccgggca gaccggcagc tacattggac agaccgccga ggccgccaag    420
cagaaagcgg ccggcgccgc gcagtacgcc aaggagaccg cgatcgccgg caaggacaag    480
```

```
accggcgccg tgctccagca ggcaggggag caggtgaaga gcgtggcggt ggggggcgaag      540 gacgcggtga tgtacacgct cgggatgtca ggcgataaca agaacaacgc cgctgccggc      600
aaggacacca gcacctacaa gcctggaact gggagtgact accagtaa                   648
```

```
<210> SEQ ID NO 18
<211> LENGTH: 215
<212> TYPE: PRT
<213> ORGANISM: Oryza sativa

<400> SEQUENCE: 18

Met Ala Ser Gln Gln Glu Arg Ala Ser Tyr His Ala Gly Glu Thr Lys
1               5                   10                  15
Ala Arg Ala Glu Glu Lys Thr Gly Arg Met Met Gly Thr Ala Gln Glu
            20                  25                  30
Lys Ala Arg Glu Ala Lys Asp Thr Ala Ser Asp Ala Ala Gly Arg Ala
        35                  40                  45
Met Gly Arg Gly His Gly Ala Lys Glu Ala Thr Lys Glu Lys Ala Tyr
    50                  55                  60
Glu Thr Lys Asp Ala Thr Lys Glu Lys Ala Tyr Glu Ala Lys Asp Ala
65                  70                  75                  80
Ala Ser Asp Ala Thr Gly Arg Ala Met Asp Lys Gly Arg Gly Ala Ala
                85                  90                  95
Gly Ala Thr Arg Asp Lys Ala Tyr Asp Ala Lys Asp Arg Ala Ala Asp
            100                 105                 110
Thr Ala Gln Ser Ala Ala Asp Arg Ala Arg Asp Gly Ala Gly Gln Thr
        115                 120                 125
Gly Ser Tyr Ile Gly Gln Thr Ala Glu Ala Ala Lys Gln Lys Ala Ala
    130                 135                 140
Gly Ala Ala Gln Tyr Ala Lys Glu Thr Ala Ile Ala Gly Lys Asp Lys
145                 150                 155                 160
Thr Gly Ala Val Leu Gln Gln Ala Gly Glu Gln Val Lys Ser Val Ala
                165                 170                 175
Val Gly Ala Lys Asp Ala Val Met Tyr Thr Leu Gly Met Ser Gly Asp
            180                 185                 190
Asn Lys Asn Asn Ala Ala Ala Gly Lys Asp Thr Ser Thr Tyr Lys Pro
        195                 200                 205
Gly Thr Gly Ser Asp Tyr Gln
    210                 215
```

```
<210> SEQ ID NO 19
<211> LENGTH: 978
<212> TYPE: DNA
<213> ORGANISM: Oryza sativa

<400> SEQUENCE: 19
aagaggcaag agcatccgta ttaaccagcc ttttgagact tgagagtgtg tgtgactcga      60
tccagcgtag tttcagttcg tgtgttggtg agtgattcca gccaagtttg cgatggcttc      120
tcagcaggaa cgggctagct accacgccgg cgagaccaag gcccgcgccg aggagaagac      180
ggggcgcatg atgggcacgg cgcaggagaa ggcgcgggag gccaaggaca cggcgtccga      240
cgccgcgggg cgcgcgatgg gcaggggaca cggcgccaag gaggcgacca aggagaaggc      300
gtacgagacc aaggacgcga ccaaggagaa ggcgtacgag gcaaaggacg cggcctccga      360
cgccaccggc cgcgccatgg acaagggccg cgccgcgggc gccacgaggg acaaggcgta      420
cgatgccaag gacagggcgg ctgacacggc gcagtccgcc gccgaccgcg cccgcgacgg      480
```

```
cgccgggcag accgggagct acattggaca gaccgccgag gccgccaagc agaaagcggc    540
cggcgccgcg cagtacgcca aggagaccgc gatcgccggc aaggacaaga ccggcgccgt    600
gctccagcag gcaggggagc aggtgaagag cgtggcggtg ggggcgaagg acgcggtgat    660
gtacacgctc gggatgtcag cgataacaa gaacaacgcc gctgccggca aggacaccag    720
cacctacaag cctggaactg ggagtgacta ccagtaatac ggtagaagaa gcatgtgtcg    780
tctttggcac tgatgccaaa gtgtacgtgt tgtatcctct ttttaagtt tcagctcgac    840 ttcgacgtgt tcggtgtcac actttggttt ttcagttgtg ctcaactgtt catgtttctg    900
gttccatgga gggccagtgt ggaggtcaat gtttaagctt tcgttttaaa atctgataat    960
aaagttggtt aagacctg                                                 978
```

<210> SEQ ID NO 20
<211> LENGTH: 214
<212> TYPE: PRT
<213> ORGANISM: Oryza sativa

<400> SEQUENCE: 20

```
Met Ala Ser Gln Gln Glu Arg Ala Ser Tyr His Ala Gly Glu Thr Lys
1               5                   10                  15

Ala Arg Ala Glu Glu Lys Thr Gly Arg Met Met Gly Thr Ala Gln Glu
            20                  25                  30

Lys Ala Arg Glu Ala Lys Asp Thr Ala Ser Asp Ala Ala Gly Arg Ala
        35                  40                  45

Met Gly Arg Gly His Gly Ala Lys Glu Ala Thr Lys Glu Lys Ala Tyr
    50                  55                  60

Glu Thr Lys Asp Ala Thr Lys Glu Lys Ala Tyr Glu Ala Lys Asp Ala
65                  70                  75                  80

Ala Ser Asp Ala Thr Gly Arg Ala Met Asp Lys Gly Arg Ala Ala Gly
                85                  90                  95

Ala Thr Arg Asp Lys Ala Tyr Asp Ala Lys Asp Arg Ala Ala Asp Thr
            100                 105                 110

Ala Gln Ser Ala Ala Asp Arg Ala Arg Asp Gly Ala Gly Gln Thr Gly
        115                 120                 125

Ser Tyr Ile Gly Gln Thr Ala Glu Ala Ala Lys Gln Lys Ala Ala Gly
    130                 135                 140

Ala Ala Gln Tyr Ala Lys Glu Thr Ala Ile Ala Gly Lys Asp Lys Thr
145                 150                 155                 160

Gly Ala Val Leu Gln Gln Ala Gly Glu Gln Val Lys Ser Val Ala Val
                165                 170                 175

Gly Ala Lys Asp Ala Val Met Tyr Thr Leu Gly Met Ser Gly Asp Asn
            180                 185                 190

Lys Asn Asn Ala Ala Ala Gly Lys Asp Thr Ser Thr Tyr Lys Pro Gly
        195                 200                 205

Thr Gly Ser Asp Tyr Gln
    210
```

<210> SEQ ID NO 21
<211> LENGTH: 642
<212> TYPE: DNA
<213> ORGANISM: Hordeum vulgare

<400> SEQUENCE: 21

```
atggcctcca accagaacca ggggagctac cacgccggcg agaccaaggc ccgcaccgag    60
gagaagaccg ggcagatgat gggcgccacc aagcagaagg cggggcagac caccgaggcc    120
```

```
accaagcaga aggccggcga gacggccgag gccaccaagc agaagaccgg cgagacggcc      180
gaggccgcca agcagaaggc cgccgaggcc aaggacaaga cggcgcagac ggcgcaggcg      240
gccaaggaca gacgtacga gacggcgcag gcggccaagg agcgcgccgc ccagggcaag      300
gaccagaccg gcagcgccct cggcgagaag acggaggcgg ccaagcagaa ggccgccgag      360
acgacggagg cggccaagca gaaggccgcc gaggcaaccg aggcggccaa gcagaaggcg      420
tccgacacgg cgcagtacac caaggagtcc gcggtggccg gcaaggacaa gaccggcagc      480
gtcctccagc aggccggcga gacggtggtg aacgccgtgg tgggcgccaa ggacgccgtg      540
gcaaacacgc tgggcatggg aggggacaac accagcgcca ccaaggacgc caccaccggc      600
gccaccgtca aggacaccac caccaccacc aggaatcact ag                        642

<210> SEQ ID NO 22
<211> LENGTH: 213
<212> TYPE: PRT
<213> ORGANISM: Hordeum vulgare

<400> SEQUENCE: 22

Met Ala Ser Asn Gln Asn Gln Gly Ser Tyr His Ala Gly Glu Thr Lys
1               5                   10                  15

Ala Arg Thr Glu Glu Lys Thr Gly Gln Met Met Gly Ala Thr Lys Gln
            20                  25                  30

Lys Ala Gly Gln Thr Thr Glu Ala Thr Lys Gln Lys Ala Gly Glu Thr
        35                  40                  45

Ala Glu Ala Thr Lys Gln Lys Thr Gly Glu Thr Ala Glu Ala Ala Lys
    50                  55                  60

Gln Lys Ala Ala Glu Ala Lys Asp Lys Thr Ala Gln Thr Ala Gln Ala
65                  70                  75                  80

Ala Lys Asp Lys Thr Tyr Glu Thr Ala Gln Ala Ala Lys Glu Arg Ala
                85                  90                  95

Ala Gln Gly Lys Asp Gln Thr Gly Ser Ala Leu Gly Glu Lys Thr Glu
            100                 105                 110

Ala Ala Lys Gln Lys Ala Ala Glu Thr Thr Glu Ala Ala Lys Gln Lys
        115                 120                 125

Ala Ala Glu Ala Thr Glu Ala Ala Lys Gln Lys Ala Ser Asp Thr Ala
    130                 135                 140

Gln Tyr Thr Lys Glu Ser Ala Val Ala Gly Lys Asp Lys Thr Gly Ser
145                 150                 155                 160

Val Leu Gln Gln Ala Gly Glu Thr Val Val Asn Ala Val Val Gly Ala
                165                 170                 175

Lys Asp Ala Val Ala Asn Thr Leu Gly Met Gly Gly Asp Asn Thr Ser
            180                 185                 190

Ala Thr Lys Asp Ala Thr Thr Gly Ala Thr Val Lys Asp Thr Thr Thr
        195                 200                 205

Thr Thr Arg Asn His
    210

<210> SEQ ID NO 23
<211> LENGTH: 552
<212> TYPE: DNA
<213> ORGANISM: Bromus inermis

<400> SEQUENCE: 23
atggcatcca accaggacaa ggcaagctac cacgccggcg aggccaaggc ccgcaccgag       60
gagaaggccg acaggtgac cggcgcggcc aaggacaagg cgtgcgaggc caaggaccgg      120
```

```
gcgtcggacg cggcggggca cgcgaccggg aagggcagg gcgccgtcga ggccacgaag      180
cagaaggccg gcgaggcggg gcagaagacg tccgagacgg cgcaggccgc caaggaccgg      240
gccgccgagg gcaaggacca ggccggcagc tacctcggcc agacggccga ggccgccaag      300
gagaaggcct cccaggcgac ggggtacacg caggacaggg ccgccgacgc ggcgcagtac      360
acgaaggact ccgccgtcgc cggcaaggac aagaccggca gcgtcctcgc tcaggccggc      420
gagcaggtga agaacgtggt ggttggcgcc aaagacgcgg tggccaacac gctggggatg      480
ggggagacaa acaacactag ctcaaccaag gacagtagca ccaccgagac gatcaccaag      540
aatcatcact ag                                                         552

<210> SEQ ID NO 24
<211> LENGTH: 183
<212> TYPE: PRT
<213> ORGANISM: Bromus inermis

<400> SEQUENCE: 24

Met Ala Ser Asn Gln Asp Lys Ala Ser Tyr His Ala Gly Glu Ala Lys
1               5                   10                  15

Ala Arg Thr Glu Glu Lys Ala Gly Gln Val Thr Gly Ala Ala Lys Asp
            20                  25                  30

Lys Ala Cys Glu Ala Lys Asp Arg Ala Ser Asp Ala Ala Gly His Ala
        35                  40                  45

Thr Gly Lys Gly Gln Gly Ala Val Glu Ala Thr Lys Gln Lys Ala Gly
    50                  55                  60

Glu Ala Gly Gln Lys Thr Ser Glu Thr Ala Gln Ala Ala Lys Asp Arg
65                  70                  75                  80

Ala Ala Glu Gly Lys Asp Gln Ala Gly Ser Tyr Leu Gly Gln Thr Ala
                85                  90                  95

Glu Ala Ala Lys Glu Lys Ala Ser Gln Ala Thr Gly Tyr Thr Gln Asp
            100                 105                 110

Arg Ala Ala Asp Ala Ala Gln Tyr Thr Lys Asp Ser Ala Val Ala Gly
        115                 120                 125

Lys Asp Lys Thr Gly Ser Val Leu Ala Gln Ala Gly Glu Gln Val Lys
    130                 135                 140

Asn Val Val Gly Ala Lys Asp Ala Val Ala Asn Thr Leu Gly Met
145                 150                 155                 160

Gly Gly Asp Asn Asn Thr Ser Ser Thr Lys Asp Ser Ser Thr Thr Glu
                165                 170                 175

Thr Ile Thr Lys Asn His His
            180

<210> SEQ ID NO 25
<211> LENGTH: 666
<212> TYPE: DNA
<213> ORGANISM: Zea mays

<400> SEQUENCE: 25
atggcttccc accaggacaa ggctagctac caggccggcg agaccaaggc ccgcaccgag      60
gagaagaccg gcaggcggt gggggcgacc aaggacacgg cgcagcacgc caaggaccgg      120
gcggcggacg cggcggggca cgcggcgggc aagggccagg acgccaagga ggccaccaag      180
cagaaggcgt ccgacaccgg cagctacctg gcaagaaga ccgacgaggc caagcacaag      240
gccggcgaga cgacggaggc caccaagcac aaggccggcg agacgacgga ggccgccaag      300
cagaaggccg gcgagacgac ggaggccgcc aagcagaagg ccggcgagac gacggagacg      360
```

```
accaagcaga aggccggcga gacgacggag gccgccaggc agaaggcagc cgacgccatg    420
gaggccgcca agcagaaggc cgccgaggcc gggcagtacg ccaaggacac cgccgtctcc    480
ggcaaggaca agtccggcgg cgtcatccag caggccactg agcaggtgaa gagcgcggcg    540
gcggggcgca aggacgcggt gatgagcacg ctggggatgg gcggggacaa caagcagggc    600
gacgccaaca ccaacaccaa caccaacacc accaaggact cctctaccat caccagggat    660
cactag                                                               666
```

```
<210> SEQ ID NO 26
<211> LENGTH: 221
<212> TYPE: PRT
<213> ORGANISM: Zea mays

<400> SEQUENCE: 26
```

Met Ala Ser His Gln Asp Lys Ala Ser Tyr Gln Ala Gly Glu Thr Lys
1               5                  10                  15

Ala Arg Thr Glu Glu Lys Thr Gly Gln Ala Val Gly Ala Thr Lys Asp
            20                  25                  30

Thr Ala Gln His Ala Lys Asp Arg Ala Ala Asp Ala Ala Gly His Ala
        35                  40                  45

Ala Gly Lys Gly Gln Asp Ala Lys Glu Ala Thr Lys Gln Lys Ala Ser
    50                  55                  60

Asp Thr Gly Ser Tyr Leu Gly Lys Lys Thr Asp Glu Ala Lys His Lys
65                  70                  75                  80

Ala Gly Glu Thr Thr Glu Ala Thr Lys His Lys Ala Gly Glu Thr Thr
                85                  90                  95

Glu Ala Ala Lys Gln Lys Ala Gly Glu Thr Thr Glu Ala Ala Lys Gln
            100                 105                 110

Lys Ala Gly Glu Thr Thr Glu Thr Thr Lys Gln Lys Ala Gly Glu Thr
        115                 120                 125

Thr Glu Ala Ala Arg Gln Lys Ala Ala Asp Ala Met Glu Ala Ala Lys
    130                 135                 140

Gln Lys Ala Ala Glu Ala Gly Gln Tyr Ala Lys Asp Thr Ala Val Ser
145                 150                 155                 160

Gly Lys Asp Lys Ser Gly Gly Val Ile Gln Gln Ala Thr Glu Gln Val
                165                 170                 175

Lys Ser Ala Ala Ala Gly Arg Lys Asp Ala Val Met Ser Thr Leu Gly
            180                 185                 190

Met Gly Gly Asp Asn Lys Gln Gly Asp Ala Asn Thr Asn Thr Asn Thr
        195                 200                 205

Asn Thr Thr Lys Asp Ser Ser Thr Ile Thr Arg Asp His
    210                 215                 220

```
<210> SEQ ID NO 27
<211> LENGTH: 690
<212> TYPE: DNA
<213> ORGANISM: Brassica napus

<400> SEQUENCE: 27
atggcgtcta accaacaaag ctacaaagct ggtgaaacca gaggcaagac tcaggagaag    60
acaggacaag caatgggagc aatgagggac aaggctgagg aaggcaagga caagacttcc   120
cagacggctc aaaaggccca acaaaggcca agagactg cccaggcagc taagacaag     180 acatctcaag ctgcccaaac gacccaacaa aggctcaag agacggcaca ggcagcgaaa    240
gacaagacat ctcaagctgc ccaaacgacc cagcaaaagg ctcatgagac gacccaatca    300
```

```
gcaaaagaca agacatctca agctgcccag acggcccaag aaaaagcccg ggagacgaag    360
gacaagaccg gaagttacat gtccgagaca ggagaagcca taaagcagaa ggctcaaaac    420
gctgctcagt acacaaagga gacggctcaa gaagcggctc agtacacgaa agagacggct    480
gaagccggta gagacaagac cggtgggttc ttgagccaga caggcgagca agtgaagcag    540
atggcaatgg gtgcagctga tgcggtgaag cacactgttg gaatggctac ggaggaagaa    600
gaccgggagc attatccagg caccactacg accactactg gtactactcg gaccactgat    660
ccgactcatc atacttatca gaggaagtga                                     690
```

<210> SEQ ID NO 28
<211> LENGTH: 229
<212> TYPE: PRT
<213> ORGANISM: Brassica napus

<400> SEQUENCE: 28

Met Ala Ser Asn Gln Gln Ser Tyr Lys Ala Gly Glu Thr Arg Gly Lys
1               5                   10                  15

Thr Gln Glu Lys Thr Gly Gln Ala Met Gly Ala Met Arg Asp Lys Ala
            20                  25                  30

Glu Glu Gly Lys Asp Lys Thr Ser Gln Thr Ala Gln Lys Ala Gln Gln
        35                  40                  45

Lys Ala Gln Glu Thr Ala Ala Ala Lys Asp Lys Thr Ser Gln Ala
    50                  55                  60

Ala Gln Thr Thr Gln Gln Lys Ala Gln Glu Thr Ala Gln Ala Ala Lys
65                  70                  75                  80

Asp Lys Thr Ser Gln Ala Ala Gln Thr Thr Gln Gln Lys Ala His Glu
                85                  90                  95

Thr Thr Gln Ser Ala Lys Asp Lys Thr Ser Gln Ala Ala Gln Thr Ala
            100                 105                 110

Gln Glu Lys Ala Arg Glu Thr Lys Asp Lys Thr Gly Ser Tyr Met Ser
        115                 120                 125

Glu Thr Gly Glu Ala Ile Lys Gln Lys Ala Gln Asn Ala Ala Gln Tyr
    130                 135                 140

Thr Lys Glu Thr Ala Gln Glu Ala Ala Gln Tyr Thr Lys Glu Thr Ala
145                 150                 155                 160

Glu Ala Gly Arg Asp Lys Thr Gly Gly Phe Leu Ser Gln Thr Gly Glu
                165                 170                 175

Gln Val Lys Gln Met Ala Met Gly Ala Ala Asp Ala Val Lys His Thr
            180                 185                 190

Val Gly Met Ala Thr Glu Glu Glu Asp Arg Glu His Tyr Pro Gly Thr
        195                 200                 205

Thr Thr Thr Thr Thr Gly Thr Thr Arg Thr Thr Asp Pro Thr His His
    210                 215                 220

Thr Tyr Gln Arg Lys
225

<210> SEQ ID NO 29
<211> LENGTH: 696
<212> TYPE: DNA
<213> ORGANISM: Zea mays

<400> SEQUENCE: 29

```
atggcttctc gtcagcagca tcctactagc taccacgccg cgagaccaa ggcccgtgcc     60 gaggagaaga cgggtcaagt gatggggggcg acgcaggaga agggaggga ggccaagcac    120
```

```
aaggcgtccg acgcctccga ccgcgccatg ggaatgggcc acgacgccat ggaggcgacc    180
agggagaagg cgcgcgccgc cgcggaccga accatgggga tgggccacga cgccggggag    240
gcggccaagg acagggcgta ccgggccaag gacgcggcct ccggtgccgc tggccgcgcc    300
agggacactg cgtccgacgc ggccggcgct gccggggacc gcgcccgcga cggcgcgcag    360
cagaccggga gctacgtcgc gcagacggcc gaggccgcca ggcagaaggc ggccggcgcc    420
gcgctgtacg ccaaggacac cgtggtggcc ggcaaggaca agaccggcgc cctcctgcag    480
caggcagggg agaaggtgat gagcacggcc gtggggccca aggacacggt tgtcagcacg    540
gccgtggggg ccaaggacac ggttgtcagc accgccgtgg gagccaagga cgcgatgatg    600
aactcgctcg gcatggccgg cgaggacaag gacggcacca ccaccaccga cgccggcaag    660
gacaccagca cccgcaagcc tggcagggac tattag                              696
```

<210> SEQ ID NO 30
<211> LENGTH: 231
<212> TYPE: PRT
<213> ORGANISM: Zea mays

<400> SEQUENCE: 30

```
Met Ala Ser Arg Gln Gln His Pro Thr Ser Tyr His Ala Gly Glu Thr
1               5                   10                  15

Lys Ala Arg Ala Glu Glu Lys Thr Gly Gln Val Met Gly Ala Thr Gln
            20                  25                  30

Glu Lys Gly Arg Glu Ala Lys His Lys Ala Ser Asp Ala Ser Asp Arg
        35                  40                  45

Ala Met Gly Met Gly His Asp Ala Met Glu Ala Thr Arg Glu Lys Ala
    50                  55                  60

Arg Ala Ala Ala Asp Arg Thr Met Gly Met Gly His Asp Ala Gly Glu
65                  70                  75                  80

Ala Ala Lys Asp Arg Ala Tyr Arg Ala Lys Asp Ala Ala Ser Gly Ala
                85                  90                  95

Ala Gly Arg Ala Arg Asp Thr Ala Ser Asp Ala Ala Gly Ala Ala Gly
            100                 105                 110

Asp Arg Ala Arg Asp Gly Ala Gln Gln Thr Gly Ser Tyr Val Ala Gln
        115                 120                 125

Thr Ala Glu Ala Ala Arg Gln Lys Ala Ala Gly Ala Ala Leu Tyr Ala
    130                 135                 140

Lys Asp Thr Val Val Ala Gly Lys Asp Lys Thr Gly Ala Leu Leu Gln
145                 150                 155                 160

Gln Ala Gly Glu Lys Val Met Ser Thr Ala Val Gly Ala Lys Asp Thr
                165                 170                 175

Val Val Ser Thr Ala Val Gly Ala Lys Asp Thr Val Val Ser Thr Ala
            180                 185                 190

Val Gly Ala Lys Asp Ala Met Met Asn Ser Leu Gly Met Ala Gly Glu
        195                 200                 205

Asp Lys Asp Gly Thr Thr Thr Thr Asp Ala Gly Lys Asp Thr Ser Thr
    210                 215                 220

Arg Lys Pro Gly Arg Asp Tyr
225                 230
```

<210> SEQ ID NO 31
<211> LENGTH: 588
<212> TYPE: DNA
<213> ORGANISM: Zea mays

<400> SEQUENCE: 31

```
atggcttccc accaggacaa ggctagctac caggccggcg aaaccaaggc ccgcaccgag      60
gagaagaccg ggcaggcggt gggggcgacc aaggacacgg cgcagcacgc caaggaccgg     120
gcggcggacg cggcggggca cgcggcgggc aagggccagg acgccaagga ggccaccaag     180
cagaaggcgt ccgacaccgg cagctacctg ggcaagaaga ccgacgaggc caagcacaag     240
gccggcgaga cgacggaggc caccaagcag aaggccggcg agacgacgga ggcgaccaag     300
cagaaggccg gcgagacgac ggaggccgcc aggcagaagg cagccgacgc catggaggca     360
gccaagcaga aggccgccga ggccgggcag tacgccaagg acaccgccgt ctccggcaag     420
gacaagtccg gcggcgtcat ccagcaggcc actgagcagg tgaagagcgc ggcggcgggc     480
gccaaggacg cggtgatgag cacgctgggg atgggcgggg acgacaagca gggcgacgcc     540
aacaccaaca ccaacaagga ctcctctacc atcaccaggg atcactag                  588
```

```
<210> SEQ ID NO 32
<211> LENGTH: 195
<212> TYPE: PRT
<213> ORGANISM: Zea mays

<400> SEQUENCE: 32

Met Ala Ser His Gln Asp Lys Ala Ser Tyr Gln Ala Gly Glu Thr Lys
1               5                   10                  15

Ala Arg Thr Glu Glu Lys Thr Gly Gln Ala Val Gly Ala Thr Lys Asp
            20                  25                  30

Thr Ala Gln His Ala Lys Asp Arg Ala Ala Asp Ala Ala Gly His Ala
        35                  40                  45

Ala Gly Lys Gly Gln Asp Ala Lys Glu Ala Thr Lys Gln Lys Ala Ser
    50                  55                  60

Asp Thr Gly Ser Tyr Leu Gly Lys Lys Thr Asp Glu Ala Lys His Lys
65                  70                  75                  80

Ala Gly Glu Thr Thr Glu Ala Thr Lys Gln Lys Ala Gly Glu Thr Thr
                85                  90                  95

Glu Ala Thr Lys Gln Lys Ala Gly Glu Thr Thr Glu Ala Ala Arg Gln
            100                 105                 110

Lys Ala Ala Asp Ala Met Glu Ala Ala Lys Gln Lys Ala Ala Glu Ala
        115                 120                 125

Gly Gln Tyr Ala Lys Asp Thr Ala Val Ser Gly Lys Asp Lys Ser Gly
    130                 135                 140

Gly Val Ile Gln Gln Ala Thr Glu Gln Val Lys Ser Ala Ala Ala Gly
145                 150                 155                 160

Ala Lys Asp Ala Val Met Ser Thr Leu Gly Met Gly Gly Asp Asp Lys
                165                 170                 175

Gln Gly Asp Ala Asn Thr Asn Thr Asn Lys Asp Ser Ser Thr Ile Thr
            180                 185                 190

Arg Asp His
        195
```

```
<210> SEQ ID NO 33
<211> LENGTH: 636
<212> TYPE: DNA
<213> ORGANISM: Triticum aestivum

<400> SEQUENCE: 33
atggcctcca accagaacca ggccagctac cacgccggcg agaccaaggc ccgcaccgag      60
gagaagaccg ggcaggtgat gggcgcgacc aaggacaagg cggggcagac cacggaggcc     120
```

```
accaagcaga aggccggaca gaccaccgag gccaccaagc agaaggccgg cgagacggcc      180
gaggcaacga agcagaaggc cggtcaggcc acggaggcca cgaagcagaa ggccggcgag      240
acggccgagg ccaccaagca gaaggccgcc gaggccaagg acaagactgc gcagacggcg      300
caggcggcca aggagcgcgc cgccgagacc aaggaccaga ccggcagcta cctcggcgag      360
aagacagaga tggccaagca gaaggccgcc gagacgaccg aggctgccaa gcagaaggcc      420
tcggagacgg cgcagtacac caaggagtcc gtcgccggca aggacaagac cggcagcgtc      480
ctccagcagg ccggcgagac ggtggtgaac gccgtggatg gcgccaagga cgccgtggcc      540
aacacgctgg gcaatgggcc ggacaacgcc accaaggaca cctccaccgg cgccaccacg      600
aaggacacca ccaccaccac caccaggaat cactag                                636
```

<210> SEQ ID NO 34
<211> LENGTH: 211
<212> TYPE: PRT
<213> ORGANISM: Triticum aestivum

<400> SEQUENCE: 34

```
Met Ala Ser Asn Gln Asn Gln Ala Ser Tyr His Ala Gly Glu Thr Lys
1               5                   10                  15

Ala Arg Thr Glu Glu Lys Thr Gly Gln Val Met Gly Ala Thr Lys Asp
            20                  25                  30

Lys Ala Gly Gln Thr Thr Glu Ala Thr Lys Gln Lys Ala Gly Gln Thr
        35                  40                  45

Thr Glu Ala Thr Lys Gln Lys Ala Gly Glu Thr Ala Glu Ala Thr Lys
    50                  55                  60

Gln Lys Ala Gly Gln Ala Thr Glu Ala Thr Lys Gln Lys Ala Gly Glu
65                  70                  75                  80

Thr Ala Glu Ala Thr Lys Gln Lys Ala Glu Ala Lys Asp Lys Thr
            85                  90                  95

Ala Gln Thr Ala Gln Ala Ala Lys Glu Arg Ala Ala Glu Thr Lys Asp
            100                 105                 110

Gln Thr Gly Ser Tyr Leu Gly Glu Lys Thr Glu Met Ala Lys Gln Lys
        115                 120                 125

Ala Ala Glu Thr Thr Glu Ala Ala Lys Gln Lys Ala Ser Glu Thr Ala
    130                 135                 140

Gln Tyr Thr Lys Glu Ser Val Ala Gly Lys Asp Lys Thr Gly Ser Val
145                 150                 155                 160

Leu Gln Gln Ala Gly Glu Thr Val Val Asn Ala Val Asp Gly Ala Lys
                165                 170                 175

Asp Ala Val Ala Asn Thr Leu Gly Asn Gly Pro Asp Asn Ala Thr Lys
            180                 185                 190

Asp Thr Ser Thr Gly Ala Thr Thr Lys Asp Thr Thr Thr Thr Thr Thr
        195                 200                 205

Arg Asn His
    210
```

<210> SEQ ID NO 35
<211> LENGTH: 214
<212> TYPE: PRT
<213> ORGANISM: Oryza sativa

<400> SEQUENCE: 35

```
Met Ala Ser Gln Gln Glu Arg Ala Ser Tyr His Ala Gly Glu Thr Lys
1               5                   10                  15

Ala Arg Ala Glu Glu Lys Thr Gly Arg Met Met Gly Thr Ala Gln Glu
```

-continued

```
                20                  25                  30
Lys Ala Arg Glu Ala Lys Asp Thr Ala Ser Asp Ala Ala Gly Arg Ala
                35                  40                  45
Met Gly Arg Gly His Gly Ala Lys Glu Ala Thr Lys Glu Lys Ala Tyr
    50                  55                  60
Glu Thr Lys Asp Ala Thr Lys Glu Lys Ala Tyr Glu Ala Lys Asp Ala
65                  70                  75                  80
Ala Ser Asp Ala Thr Gly Arg Ala Met Asp Lys Gly Arg Ala Ala Gly
                85                  90                  95
Ala Thr Arg Asp Lys Ala Tyr Asp Ala Lys Asp Arg Ala Ala Asp Thr
                100                 105                 110
Ala Gln Ser Ala Ala Asp Arg Ala Arg Asp Gly Ala Gly Gln Thr Gly
                115                 120                 125
Ser Tyr Ile Gly Gln Thr Ala Glu Ala Ala Lys Gln Lys Ala Ala Gly
            130                 135                 140
Ala Ala Gln Tyr Ala Lys Glu Thr Ala Ile Ala Gly Lys Asp Lys Thr
145                 150                 155                 160
Gly Ala Val Leu Gln Gln Ala Gly Glu Gln Val Lys Ser Val Ala Val
                165                 170                 175
Gly Ala Lys Asp Ala Val Met Tyr Thr Leu Gly Met Ser Gly Asp Asn
                180                 185                 190
Lys Asn Asn Ala Ala Ala Gly Lys Asp Thr Ser Thr Tyr Lys Pro Gly
                195                 200                 205
Thr Gly Ser Asp Tyr Gln
                210

<210> SEQ ID NO 36
<211> LENGTH: 169
<212> TYPE: PRT
<213> ORGANISM: Triticum aestivum

<400> SEQUENCE: 36

Met Ala Ser Asn Gln Asn Gln Ala Ser Tyr Ala Ala Gly Glu Thr Lys
1               5                   10                  15
Ala Arg Thr Glu Glu Lys Thr Gly Gln Met Met Asp Lys Ala Gly Gln
                20                  25                  30
Ala Thr Glu Ala Thr Lys Gln Lys Ala Gly Glu Ala Lys Asp Lys Thr
            35                  40                  45
Ala Gln Thr Ala Gln Ala Lys Asp Arg Ala Ala Glu Ser Lys Asp
    50                  55                  60
Gln Thr Gly Ser Phe Leu Gly Glu Lys Thr Glu Ala Ala Lys Gln Lys
65                  70                  75                  80
Thr Ala Glu Ala Thr Asp Ala Ala Lys Gln Lys Ala Ser Glu Thr Ala
                85                  90                  95
Gln Tyr Ala Gln Glu Arg Ser Ser Asp Ala Ala Gln Tyr Thr Lys Glu
                100                 105                 110
Ser Ala Val Ala Gly Lys Asp Lys Thr Gly Ser Val Leu Gln Gln Ala
            115                 120                 125
Gly Glu Thr Val Val Ser Ala Val Gly Ala Lys Asp Ala Val Ala
            130                 135                 140
Asn Thr Leu Gly Met Gly Gly Asp Asn Thr Asn Thr Ala Lys Asp Ser
145                 150                 155                 160
Thr Thr Glu Lys Ile Thr Arg Asp His
                165
```

PLANTS HAVING INCREASE YIELD AND METHOD FOR MAKING THE SAME

RELATED APPLICATIONS

This application is a national stage application (under 35 U.S.C. 371) of PCT/EP2006/066425 filed Sep. 15, 2006, which claims benefit of European application 05108483.8 filed Sep. 15, 2005 and U.S. Provisional application 60/717,738 filed Sep. 19, 2005.

The present invention relates generally to the field of molecular biology and concerns a method for increasing plant yield relative to control plants. More specifically, the present invention concerns a method for increasing plant yield comprising modulating expression in a plant of a nucleic acid encoding the OsLEA3a polypeptide or a homologue thereof. The invention furthermore relates to a compositional change in metabolites linked to the yield increase. The present invention also concerns plants having modulated expression of a nucleic acid encoding the OsLEA3a polypeptide or a homologue thereof, which plants have increased yield relative to control plants. The invention also provides constructs useful in the methods of the invention.

The ever-increasing world population and the dwindling supply of arable land available for agriculture fuels research towards improving the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits. A trait of particular economic interest is yield, necessarily related to a specified crop, area and/or period of time. Yield is normally defined as the measurable produce of economic value from a crop. This may be defined in terms of quantity and/or quality. Yield is directly dependent on several factors, for example, the number and size of the organs, plant architecture (for example, the number of branches), seed production and more. Root development, nutrient uptake and stress tolerance may also be important factors in determining yield. Optimizing one of the above-mentioned factors may therefore contribute to increasing crop yield.

Plant biomass is yield for forage crops like alfalfa, silage corn and hay. Many proxies for yield have been used in grain crops. Chief amongst these are estimates of plant size. Plant size can be measured in many ways depending on species and developmental stage, but include total plant dry weight, above-ground dry weight, above-ground fresh weight, leaf area, stem volume, plant height, rosette diameter, leaf length, root length, root mass, tiller number and leaf number. Many species maintain a conservative ratio between the size of different parts of the plant at a given developmental stage. These allometric relationships are used to extrapolate from one of these measures of size to another (e.g. Tittonell et al 2005 Agric Ecosys & Environ 105: 213). Plant size at an early developmental stage will typically correlate with plant size later in development. A larger plant with a greater leaf area can typically absorb more light and carbon dioxide than a smaller plant and therefore will likely gain a greater weight during the same period (Fasoula & Tollenaar 2005 Maydica 50:39). This is in addition to the potential continuation of the micro-environmental or genetic advantage that the plant had to achieve the larger size initially. There is a strong genetic component to plant size and growth rate (e.g. ter Steege et al 2005 Plant Physiology 139:1078), and so for a range of diverse genotypes plant size under one environmental condition is likely to correlate with size under another (Hittalmani et al 2003 Theoretical Applied Genetics 107:679). In this way a standard environment is used as a proxy for the diverse and dynamic environments encountered at different locations and times by crops in the field.

Harvest index, the ratio of seed yield to above-ground dry weight, is relatively stable under many environmental conditions and so a robust correlation between plant size and grain yield can often be obtained (e.g. Rebetzke et al 2002 Crop Science 42:739). These processes are intrinsically linked because the majority of grain biomass is dependent on current or stored photosynthetic productivity by the leaves and stem of the plant (Gardener et al 1985 Physiology of Crop Plants. Iowa State University Press, pp 68-73). Therefore, selecting for plant size, even at early stages of development, has been used as an indicator for future potential yield (e.g. Tittonell et al 2005 Agric Ecosys & Environ 105: 213). When testing for the impact of genetic differences on stress tolerance, the ability to standardize soil properties, temperature, water and nutrient availability and light intensity is an intrinsic advantage of greenhouse or plant growth chamber environments compared to the field. However, artificial limitations on yield due to poor pollination due to the absence of wind or insects, or insufficient space for mature root or canopy growth, can restrict the use of these controlled environments for testing yield differences. Therefore, measurements of plant size in early development, under standardized conditions in a growth chamber or greenhouse, are standard practices to provide indication of potential genetic yield advantages.

Seed yield is a particularly important trait since the seeds of many plants are important for human and animal nutrition. Crops such as, corm, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain. The ability to increase plant yield would have many applications in areas such as agriculture, including in the production of ornamental plants, arboriculture, horticulture and forestry. Increasing yield may also find use in the production of algae for use in bioreactors (for the biotechnological production of substances such as pharmaceuticals, antibodies or vaccines, or for the bioconversion of organic waste) and other such areas.

OsLEA3a is a rice protein that may be classified as a Group 3a LEA protein (Wise & Tunnacliffe, Trends Plant Sci. 9, 13-17, 2004). LEA proteins (Late Embryogenesis Abundant proteins) are expressed at different stages of late embryogenesis in higher plant seed embryos and under conditions of dehydration stress. They may also be induced by abscisic acid. Often, the function of these proteins is unknown. A recent classification discriminates 7 groups within the LEA proteins; several of these groups are characterised by a typical sequence motif and computational analysis allowed a prediction of function (Wise & Tunnacliffe, 2004). Group 3 Lea proteins comprise the LEA superfamilies 2 and 5 and are characterised by the presence of 11-mer amino acid motifs that broadly may be defined as follows: on positions 1, 2, 5 and 9 a hydrophobic residue, on positions 3, 7 and 11 a negative or amide residue, on positions 6 and 8 a positive residue and on positions 4 and 10 any amino acid may be present (Wise & Tunnacliffe, 2004, Dure III, L., Protein and Peptide Letters 8, 115-122, 2001). Group 3 LEA proteins are postulated to function as a molecular chaperone and may play a role in desiccation tolerance (Goyal et al., Biochem. J. 388, 151-157, 2005). Because LEA proteins are induced in plants under water stress conditions, it was hypothesised that LEA proteins could be useful for making plants more salt and drought resistant. Xu et al. (Plant Physiol. 110, 249-257, 1996) demonstrated that rice transformed with barley LEA3a was more tolerant to water deficit and salt stress, Rohila et al. (Plant Sci. 163, 525-532, 2002) describe transgenic Basmati rice with constitutive or stress-induced expression of barley LEA3a that show increased tolerance against drought and high salinity. Similarly, wheat transformed with barley LEA3a under control of a constitutive promoter were more drought resistant than the control plants (Bahieldin et al., Physiol. Plant. 123, 421-427, 2005). However, these studies also showed that there was no yield increase compared to control plants when the plants were grown under conditions without stress. WO 97/13843 describes the use of barley HVA1 for increasing resistance to drought and salt stress, however it was not demonstrated that plants expressing barley HVA1 had improved growth properties under non-stress conditions.

Surprisingly, it has now been found that modulating expression in a plant of a nucleic acid encoding the LEA3a polypeptide from rice (OsLEA3a) or a homologue thereof gives plants having increased yield relative to control plants. This yield increase was surprisingly observed when the plants were cultivated under conditions without stress (non-stress conditions). Preferably, the homologue of OsLEA3a is of plant origin, more preferably, the OsLEA3a homologue originates from a monocot plant, provided that the OsLEA3a homologue is not SEQ ID NO: 22 (*Hordeum vulgare*). Most preferably, the homologue originates from *Oryza sativa*.

BRIEF DESCRIPTION OF THE FIGURES

FIGS. 3A-I details examples of sequences useful in performing the methods according to the present invention. SEQ ID NO: 1 and 2 represent the OsLEA3a coding sequence and the deduced protein sequence. SEQ ID NO: 7 to 20 represent sequences of other rice LEA3a proteins and coding sequences, SEQ ID NO: 21 and 22 are sequences of barley HVA1. SEQ ID NO: 4 and 5 are the primer sequences used for cloning OsLEA3a. SEQ ID NO: 23 to 34 represent coding sequences and protein sequences of LEA3 homologues from non-rice species. SEQ ID NO: 35 and SEQ ID NO: 36 are variants of SEQ ID NO: 14 and SEQ ID NO: 34 respectively. SEQ ID NO: 3 represents the consensus signature sequence.

FIG. 4 represents a sequence identity/similarity table produced with MATGAT (BLOSUM62 matrix, gap opening penalty 11, gap extension penalty 1). Sequence identities are given in bold above the diagonal, sequence similarities are given below the diagonal. Full length protein sequences were used.

Figures 1, 2:
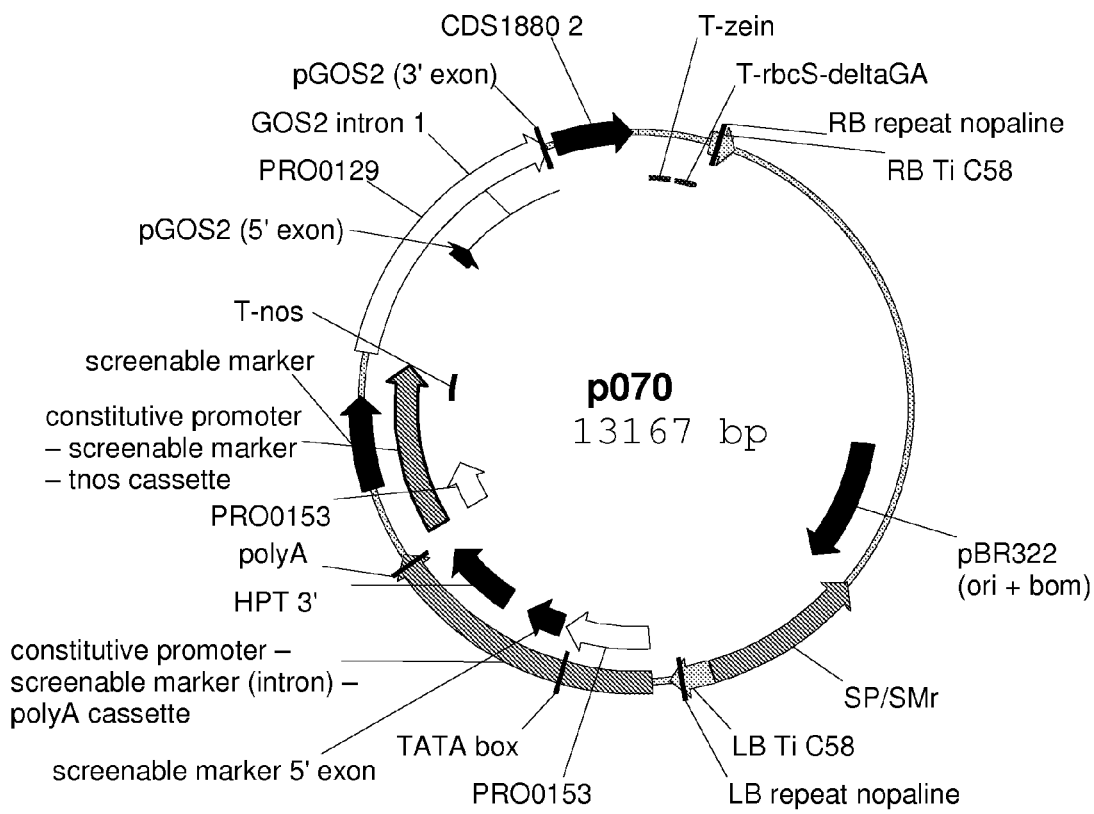
FIG. 1 shows the typical domain structure of OsLEA3a polypeptides. The protein encoded by SEQ ID NO: 2 comprises two LEA_4 domains (in bold); the 11-mer amino acid motifs are underlined. The most C-terminal domain (in italics) is a low complexity region.
FIG. 2 shows a binary vector p070, for expression in *Oryza sativa* of an *Arabidopsis thaliana* OsLEA3a coding sequence under the control of a GOS2 promoter (internal reference PRO0129).

According to one embodiment of the present invention, there is provided a method for increasing plant yield, comprising modulating expression in a plant of a nucleic acid encoding the OsLEA3a polypeptide or a homologue thereof.

Advantageously, performance of the methods according to the present invention results in plants having increased yield, particularly seed yield, relative to control plants.

The choice of control plants is a routine part of an experimental setup and may include corresponding wild type plants or corresponding plants without the gene of interest. The control plant is typically of the same plant species or even of the same variety as the plant to be compared. The control plant may also be a nullizygote of the plant to be compared. Nullizygotes are individuals missing the transgene by segregation. A "control plant" as used herein refers not only to whole plants, but also to plant parts, including seeds and seed parts.

A "reference", "reference plant", "control", "control plant", "wild type" or "wild type plant" is in particular a cell, a tissue, an organ, a plant, or a part thereof, which was not produced according to the method of the invention. Accordingly, the terms "wild type", "control" or "reference" are exchangeable and can be a cell or a part of the plant such as an organelle or tissue, or a plant, which was not modified or treated according to the herein described method according to the invention. Accordingly, the cell or a part of the plant such as an organelle or a plant used as wild type, control or reference corresponds to the cell, plant or part thereof as much as possible and is in any other property but in the result of the process of the invention as identical to the subject matter of the invention as possible. Thus, the wild type, control or reference is treated identically or as identical as possible, saying that only conditions or properties might be different which do not influence the quality of the tested property. That means in other words that the wild type denotes (1) a plant, which carries the unaltered or not modulated form of a gene or allele or (2) the starting material/plant from which the plants produced by the process or method of the invention are derived.

Preferably, any comparison between the wild type plants and the plants produced by the method of the invention is carried out under analogous conditions. The term "analogous conditions" means that all conditions such as, for example, culture or growing conditions, assay conditions (such as buffer composition, temperature, substrates, pathogen strain, concentrations and the like) are kept identical between the experiments to be compared.

The "reference", "control", or "wild type" is preferably a subject, e.g. an organelle, a cell, a tissue, a plant, which was not modulated, modified or treated according to the herein described process of the invention and is in any other property as similar to the subject matter of the invention as possible. The reference, control or wild type is in its genome, transcriptome, proteome or metabolome as similar as possible to the subject of the present invention. Preferably, the term "reference-" "control-" or "wild type-" -organelle, -cell, -tissue or plant, relates to an organelle, cell, tissue or plant, which is nearly genetically identical to the organelle, cell, tissue or plant, of the present invention or a part thereof preferably 95%, more preferred are 98%, even more preferred are 99.00%, in particular 99.10%, 99.30%, 99.50%, 99.70%, 99.90%, 99.99%, 99.999% or more. Most preferably the "reference", "control", or "wild type" is a subject, e.g. an organelle, a cell, a tissue, a plant, which is genetically identical to the plant, cell organelle used according to the method of the invention except that nucleic acid molecules or the gene product encoded by them are changed, modulated or modified according to the inventive method.

The term "expression" or "gene expression" means the appearance of a phenotypic trait as a consequence of the transcription of a specific gene or specific genes. The term "expression" or "gene expression" in particular means the transcription of a gene or genes into structural RNA (rRNA, tRNA) or mRNA with subsequent translation of the latter into a protein. The process includes transcription of DNA, processing of the resulting mRNA product and its translation into an active protein.

The term "modulation" means in relation to expression or gene expression, a process in which the expression level is changed by said gene expression in comparison to the control plant, preferably the expression level is increased. The original, unmodulated expression may be of any kind of expression of a structural RNA (rRNA, tRNA) or mRNA with subsequent translation. The term "modulating the activity" shall mean any change of the expression of the inventive nucleic acid sequences or encoded proteins, which leads to increased yield and/or increased growth of the plants.

The term "yield" in general means a measurable produce of economic value, necessarily related to a specified crop, to an area, and to a period of time. Individual plant parts directly contribute to yield based on their number, size and/or weight, whereas the actual yield is the yield per acre for a crop and year, which is determined by dividing total production (includes both harvested and appraised production) by planted acres.

The terms "increase", "improving" or "improve" are interchangeable and shall mean in the sense of the application at least a 5%, 6%, 7%, 8%, 9% or 10%, preferably at least 15% or 20%, more preferably 25%, 30%, 35% or 40% more yield and/or growth in comparison to the wild type plant as defined herein.

The increase referring to the activity of the polypeptide amounts in a cell, a tissue, a organelle, an organ or an organism or a part thereof preferably to at least 5%, preferably to at least 10% or at to least 15%, especially preferably to at least 20%, 25%, 30% or more, very especially preferably are to at least 40%, 50% or 60%, most preferably are to at least 70% or more in comparison to the control, reference or wild type.

The term "increased yield" as defined herein is taken to mean an increase in biomass (weight) of one or more parts of a plant, which may include aboveground (harvestable) parts and/or (harvestable) parts below ground.

In particular, such harvestable parts are seeds, and performance of the methods of the invention results in plants having increased seed yield relative to the seed yield of control plants.

Increased seed yield may manifest itself as one or more of the following: a) an increase in seed biomass (total seed weight) which may be on an individual seed basis and/or per plant and/or per hectare or acre; b) increased number of flowers per plant; c) increased number of (filled) seeds; d) increased seed filling rate (which is expressed as the ratio between the number of filled seeds divided by the total number of seeds; e) increased harvest index, which is expressed as a ratio of the yield of harvestable parts, such as seeds, divided by the total biomass; and f) increased thousand kernel weight (TKW), which is extrapolated from the number of filled seeds counted and their total weight. An increased TKW may result from an increased seed size and/or seed weight, and may also result from an increase in embryo and/or endosperm size.

An increase in seed yield may also be manifested as an increase in seed size and/or seed volume, which may also influence the composition of seeds (including oil, protein and carbohydrate total content and composition). Furthermore, an increase in seed yield may also manifest itself as an increase in seed area and/or seed length and/or seed width and/or seed perimeter. Increased yield may also result in modified architecture, or may occur because of modified architecture.

Taking corn as an example, a yield increase may be manifested as one or more of the following: increase in the number of plants per hectare or acre, an increase in the number of ears per plant, an increase in the number of rows, number of kernels per row, kernel weight, thousand kernel weight, ear length/diameter, increase in seed filling rate (which is the number of filled seeds divided by the total number of seeds and multiplied by 100), among others.

Taking rice as an example, a yield increase may be manifested by an increase in one or more of the following: number of plants per hectare or acre, number of panicles per plant, number of spikelets per panicle, number of flowers (florets) per panicle, (which is expressed as a ratio of the number of filled seeds over the number of primary panicles), increase in the seed filling rate, (which is the number of filled seeds divided by the total number of seeds and multiplied by 100), increase in thousand kernel weight, among others. An increase in yield may also result in modified architecture, or may occur as a result of modified architecture.

According to a preferred feature, performance of the methods of the invention result in plants having increased yield, particularly seed yield. Therefore, according to the present invention, there is provided a method for increasing plant yield, which method comprises modulating expression in a plant of a nucleic acid encoding the OsLEA3a polypeptide or a homologue thereof.

Since the transgenic plants according to the present invention have increased yield, it is likely that these plants exhibit an increased growth rate (during at least part of their life cycle), relative to the growth rate of control plants at a corresponding stage in their life cycle. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigour, growth rate, flowering time and speed of seed maturation. The increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible (a similar effect may be obtained with earlier flowering time). If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of rice plants followed by, for example, the sowing and optional harvesting of soy bean, potato or any other suitable plant). Harvesting additional times from the same rootstock in the case of some crop plants may also be possible. Altering the harvest cycle, of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

Plants with an increased growth rate exhibit in one or more parts of that plant, an altered metabolism, reflected as altered levels of metabolites. The altered metabolite levels are linked to the presence of the transgene. Therefore, the metabolic profile may be used as a diagnostic tool to characterise or identify plants having increased yield, to predict new proteins that are involved in the yield increase, or to identify the pathways that are involved in the yield increase.

The term "metabolites" refers to intermediate substances, preferably such of low molecular weight, which occur during anabolism and catabolism in a plant or a plant cell, in other words, a substance produced or consumed during metabolism, such as amino acids. The term "improved composition" of metabolites refers to desired changes in concentration of these metabolites. Depending on the type of metabolite, the change may be an increase or decrease in concentration. Preferably, the change in metabolite concentration/level is measured relative to suitable control plants. Preferred metabolites in the present invention comprise metabolites from, for example, amino acid metabolism, carotenoid metabolism, cofactor metabolism, fatty acid metabolism, organic acid metabolism, phenolics metabolism, phytohormone metabolism, phytosterol metabolism, sugar metabolism, tocopherol and related compound metabolism, wax compound metabolism, lipid metabolism. The levels of various metabolite typically vary within certain limits (see for example the data in Example 6) and the changes in levels of one or more metabolites may be used to define a metabolic profile. Such a metabolic profile may comprise data for altered levels of specific metabolites and/or classes of metabolites (such as amino acid metabolism, carotenoid metabolism, cofactor metabolism, fatty acid metabolism, organic acid metabolism, phenolics metabolism, phytohormone metabolism, phytosterol metabolism, sugar metabolism, tocopherol and related compound metabolism, wax compound metabolism, lipid metabolism). Metabolite levels may be altered substantially throughout the whole plant or in certain plant parts, organs, tissues or cells, due to the modulated expression of the gene of interest, in casu LEA3a. In a preferred embodiment, the metabolite levels are altered in seeds.

According to a preferred feature of the present invention, performance of the methods of the invention gives plants having an increased growth rate or increased yield in comparison to control plants. Therefore, according to the present invention, there is provided a method for increasing yield and/or growth rate in plants, which method comprises modulating expression in a plant of a nucleic acid encoding the OsLEA3a polypeptide or a homologue thereof.

An increase in yield and/or growth rate occurs whether the plant is under non-stress conditions or whether the plant is exposed to various stresses compared to control plants. The increase in yield and/or growth rate is particularly observed when the plant is under non-stress conditions. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the typical stresses to which a plant may be exposed. These stresses may be the everyday biotic and/or abiotic (environmental) stresses to which a plant is exposed. Typical abiotic or environmental stresses include temperature stresses caused by atypical hot or cold/freezing temperatures; salt stress; water stress (drought or excess water). Chemicals may also cause abiotic stresses. Biotic stresses are typically those stresses caused by pathogens, such as bacteria, viruses, fungi and insects.

In particular, the methods of the present invention may be performed under non-stress conditions to give plants having increased yield relative to control plants. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol (2003) 133: 1755-1767) describes a particularly high degree of "cross talk" between drought stress and high-salinity stress. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signaling pathways and cellular responses, such as the production of stress proteins, up-regulation of anti-oxidants, accumulation of compatible solutes and growth arrest. The term "non-stress" conditions as used herein are those environmental conditions that do not impose stress, such as the stresses described above, on plants. Persons skilled in the art are aware of normal soil conditions and climatic conditions for a given location.

The abovementioned growth characteristics may advantageously be modified in any plant.

The term "plant" as used herein encompasses whole plants, ancestors and progeny of the plants, plant cells and plant parts, including seeds, shoots, stems, leaves, roots (including tubers), flowers, and tissues and organs, wherein each of the aforementioned comprise the gene/nucleic acid of interest. The term "plant" also encompasses suspension cultures, callus tissue, embryos, meristematic regions, gametophytes, sporophytes, pollen and microspores, again wherein each of the aforementioned comprise the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agropyron* spp., *Allium* spp., *Amaranthus* spp., *Ananas comosus, Annona* spp., *Apium graveolens, Arabidopsis thaliana, Arachis* spp, *Artocarpus* spp., *Asparagus officinalis, Avena sativa, Averrhoa carambola, Benincasa hispida, Bertholletia excelsea, Beta vulgaris, Brassica* spp., *Cadaba farinosa, Camellia sinensis, Canna indica, Capsicum* spp., *Carex elata, Carica papaya, Carissa macrocarpa, Carya* spp., *Carthamus tinctorius, Castanea* spp., *Cichorium endivia, Cinnamomum* spp., *Citrullus lanatus, Citrus* spp., *Cocos* spp., *Coffea* spp., *Colocasia esculenta, Cola* spp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Eleusine coracana, Eriobotrya japonica, Eugenia uniflora, Fagopyrum* spp., *Fagus* spp., *Ficus carica, Fortunella* spp., *Fragaria* spp., *Ginkgo biloba, Glycine* spp., *Gossypium hirsutum, Helianthus* spp., *Hemerocallis fulva, Hibiscus* spp., *Hordeum* spp., *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Momordica* spp., *Morus nigra, Musa* spp., *Nicotiana* spp., *Olea* spp., *Opuntia* spp., *Ornithopus* spp., *Oryza* spp., *Panicum miliaceum, Passiflora edulis, Pastinaca sativa, Persea* spp., *Petroselinum crispum, Phaseolus* spp., *Phoenix* spp., *Physalis* spp., *Pinus* spp., *Pistacia vera, Pisum* spp., *Poa* spp., *Populus* spp., *Prosopis* spp., *Pnunus* spp., *Psidium* spp., *Punica granatum, Pyrus communis, Quercus* spp., *Raphanus sativus, Rheum rhabarbarum, Ribes* spp., *Rubus* spp., *Sacchanum* spp., *Sambucus* spp., *Secale cereale, Sesamum* spp., *Sinapis* sp., *Solanum* spp., *Sorghum bicolor, Spinacia* spp., *Syzygium* spp., *Tamarindus indica, Theobroma cacao, Trifolium* spp., *Triticosecale rimpaui, Triticum* spp., *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amongst others.

Other advantageous plants are selected from the group consisting of Asteraceae such as the genera *Helianthus, Tagetes* e.g. the species *Helianthus annuus* [sunflower], *Tagetes lucida, Tagetes erecta* or *Tagetes tenuifolia* [Marigold]; Brassicaceae such as the genera *Brassica, Arabidopsis* e.g. the species *Brassica napus, Brassica rapa* ssp. [canola, oilseed rape, turnip rape] or *Arabidopsis thaliana*; Fabaceae such as the genera *Glycine* e.g. the species *Glycine max, Soja hispida* or *Soja max* [soybean]; Linaceae such as the genera *Linum* e.g. the species *Linum usitatissimum*, [flax, linseed]; Poaceae such as the genera *Hordeum, Secale, Avena, Sorghum, Oryza, Zea, Triticum* e.g. the species *Hordeum vulgare* [barley], *Secale cereale* [rye], *Avena sativa, Avena fatua, Avena byzantina, Avena fatua* var. sativa, *Avena hybrida* [oat], *Sorghum bicolor* [sorghum, millet], *Oryza sativa, Oryza latifolia* [rice], *Zea mays* [corn, maize] *Triticum aestivum, Triticum durum, Triticum turgidum, Triticum hybernum, Triticum macha, Triticum sativum* or *Triticum vulgare* [wheat, bread wheat, common wheat]; Solanaceae such as the genera *Solanum, Lycopersicon* e.g. the species *Solanum tuberosum* [potato], *Lycopersicon esculentum, Lycopersicon lycopersicum, Lycopersicon pyriforme, Solanum integrifolium* or *Solanum lycopersicum* [tomato].

According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, sorghum and oats.

The term "OsLEA3a polypeptide or a homologue thereof" as defined herein refers to a rice LEA3a polypeptide such as the one represented in SEQ ID NO: 2 and to proteins that belong to Group 3 of LEA proteins, that have 2 LEA_4 protein domains corresponding to the Pfam accession PF02987 or the InterPro accession IPR004238 and that comprise the 11-mer amino acid sequence motif generally defined as follows: on positions 1, 2, 5 and 9 a hydrophobic residue, on positions 3, 7 and 11 a negative or amide residue, on positions 6 and 8 a positive residue and on positions 4 and 10 any amino acid may be present; within this motif one mismatch may occur (Dure III, L., Protein and Peptide Letters 8, 115-122, 2001). The group of hydrophobic amino acid residues consists of A, C, F, G, I, L, M, T, V, W, S and Y. Negative amino acids are D or E and amide residues are Q and N. Positive amino acids are H, K and R. The sequence conservation in this motif is not absolute and one or two mismatches may occur (FIGS. 3A-I).

Preferably, the 11-mer amino acid sequence motif (hereafter named consensus signature) corresponds to the sequence

```
                                             (SEQ ID NO: 3)
T(S/T/A/K)  (Q/E/D)A(A/T)  (R/K)  (D/Q/E)

(K/R)A(A/G/Y)  (E/G),
``` further preferably the consensus signature sequence corresponds to the sequence

```
T  (S/T/A/K)  (Q/E/D)A(A/T)  (R/K)  (D/Q/E)

(K/R)A(A/G/Y)  E
``` more preferably, the consensus signature corresponds to the sequence T(S/A/K) (Q/D)A(A/T) (R/K) (D/E)KA(A/Y)E, most preferably the consensus signature is T(S/A) QAARDKAAE.

The term "domain" refers to a set of amino acids conserved at specific positions along an alignment of sequences of evolutionarily related proteins. While amino acids at other positions can vary between homologues, amino acids that are highly conserved at specific positions indicate amino acids that are essential in the structure, the stability, or the activity of a protein. Identified by their high degree of conservation in aligned sequences of a family of protein homologues, they can be used as identifiers to determine if any polypeptide in question belongs to a previously identified polypeptide family (in this case, the family of LEA3 proteins). The term "motif" or "consensus sequence" or "signature" refers to a short conserved region in a protein sequence. Motifs are frequently highly conserved parts of domains, but may also include only part of the domain, or be located outside of conserved domain (if all of the amino acids of the motif fall outside of a defined domain).

Specialist databases exist for the identification of domains. The LEA_4 domain in a LEA3 protein may be identified using, for example, SMART (Schultz et al. (1998) Proc. Natl.

Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAIPress, Menlo Park; Hulo et al., Nucl. Acids. Res. 32:D134-D137, (2004)) or Pfam (Bateman et al., Nucleic Acids Research 30(1): 276-280 (2002)). A set of tools for in silico analysis of protein sequences is available on the ExPASY proteomics server (hosted by the Swiss Institute of Bioinformatics (Gasteiger et al., ExPASy: the proteomics server for in-depth protein knowledge and analysis, Nucleic Acids Res. 31:3784-3788 (2003)). The OsLEA3a protein sequence was analysed with the SMART tool (version 4.1; Schultz et al. (1998) Proc. Natl. Acad. Sci. USA 95, 5857-5864; Letunic et al. (2002) Nucleic Acids Res 30, 242-244) and was used to screen the Pfam (Version 17.0, March 2005; Bateman et al. (2004) Nucl. Acids. Res. 32, D138-141) and InterPro database (Release 11.0, 26 Jul. 2005; Mulder et al. (2005) Nucl. Acids. Res. 33, D201-205). The first LEA_4 domain in the sequence of SEQ ID NO: 2 starts at G28 and ends at D97, the second one starts at G101 to D163.

By aligning other protein sequences with SEQ ID NO: 2, the corresponding consensus signature sequence, the LEA_4 domain or other sequence motifs may easily be identified. In this way, LEA3 polypeptides or homologues thereof (encompassing orthologues and paralogues) may readily be identified, using routine techniques well known in the art, such as by sequence alignment. Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the alignment of two complete sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information. Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences.). Minor manual editing may be performed to optimise alignment between conserved motifs, as would be apparent to a person skilled in the art. Furthermore, instead of using full length sequences for the identification of homologues, specific domains (such as the LEA_4 domain) may be used as well. The sequence identity values, which are indicated below as a percentage were determined over the entire conserved domain or nucleic acid or amino acid sequence using the programs mentioned above using the default parameters.

Examples of OsLEA3a proteins or homologues thereof include the sequences represented by SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 24, SEQ ID NO: 26, SEQ ID NO: 28, SEQ ID NO:30, SEQ ID NO:32, SEQ ID NO: 34, SEQ ID NO: 35 and SEQ ID NO: 36.

It is to be understood that sequences falling under the definition of "OsLEA3a polypeptide or homologue thereof" are not to be limited to the sequences represented by SEQ ID NO: 2, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 24, SEQ ID NO: 26, SEQ ID NO: 28, SEQ ID NO:30, SEQ ID NO:32, SEQ ID NO: 34, SEQ ID NO: 35 and SEQ ID NO: 36, but that any polypeptide comprising the consensus signature sequence of SEQ ID NO: 3 and preferably also having at least 42% sequence identity (using the Needleman-Wunsch algorithm with a Gap opening penalty of 11 and a Gap extension penalty of 1) to SEQ ID NO: 2, may be suitable for use in the methods of the invention. However the term "OsLEA3a polypeptide or homologue thereof" as used herein does not encompass SEQ ID NO: 22 (LEA3a from *Hordeum vulgare*). Preferably, the polypeptide is a polypeptide from nice.

Encompassed by the term "homologues" are orthologous sequences and paralogous sequences, two special forms of homology which encompass evolutionary concepts used to describe ancestral relationships of genes. Paralogues are genes within the same species that have originated through duplication of an ancestral gene and orthologues are genes from different organisms that have originated through speciation.

Orthologues and paralogues may be found by performing a so-called reciprocal blast search. This may be done by a first BLAST involving BLASTing a query sequence (for example, SEQ ID NO: 1 or SEQ ID NO: 2) against any sequence database, such as the publicly available NCBI database. BLASTN or TBLASTX (using standard default values) may be used when starting from a nucleotide sequence and BLASTP or TBLASTN (using standard default values) may be used when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 1 or SEQ ID NO: 2, the second BLAST would therefore be against rice sequences). The results of the first and second BLASTs are then compared. A paralogue is identified if a high-ranking hit from the second BLAST is from the same species as from which the query sequence is derived; an orthologue is identified if a high-ranking hit is not from the same species as from which the query sequence is derived. Preferred orthologues are orthologues of SEQ ID NO: 1 or SEQ ID NO: 2. High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. Preferably the score is greater than 50, more preferably greater than 100; and preferably the E-value is less than e-5, more preferably less than e-6. In the case of large families, ClustalW may be used, followed by the generation of a neighbour joining tree, to help visualize clustering of related genes and to identify orthologues and paralogues. Examples of sequences orthologous to SEQ ID NO: 2 include SEQ ID NO: 24, SEQ ID NO: 36, SEQ ID NO: 32 and SEQ ID NO: 22. Examples of paralogues of SEQ ID NO: 2 include SEQ ID NO: 8 and SEQ ID NO: 12.

Preferably, the LEA_4 domains of LEA3 proteins useful in the methods of the present invention have, in increasing order of preference, at least 40%, 42%, 45%, 49%, 50%, 55%, 60%, 65%, 70%, 75%, 80%, 85%, 90%, 95%, 96%, 97%, 98% or 99% sequence identity to the OsLEA3 protein of SEQ ID NO: 2. The matrix shown in FIG. 4 shows similarities and identities (in bold) over the full-length of the protein. In case only specific domains are compared, the identity or similarity may be higher among the different proteins.

An assay may be carried out to determine OsLEA3a activity. To determine LEA3 protein activity, assays are available and known in the art, for example, a heat stress and a water stress assay are described by Goyal et al. (Biochem. J. 388, 151-157, 2005).

Furthermore, expression of the OsLEA3a protein or of a homologue thereof in plants, and in particular in rice, has the effect of increasing yield of the transgenic plant when compared to control plants, wherein increased yield comprises at least one of: total weight of seeds, total number of seeds and number of filled seeds.

An OsLEA3a polypeptide or homologue thereof is encoded by an OsLEA3a nucleic acid/gene. Therefore the term "OsLEA3a nucleic acid/gene" as defined herein is any nucleic acid/gene encoding an OsLEA3a polypeptide or a homologue thereof as defined above.

Examples of OsLEA3a nucleic acids include but are not limited to those represented by any one of SEQ ID NO: 1, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 23, SEQ ID NO: 25, SEQ ID NO: 27, SEQ ID NO: 29, SEQ ID NO: 31 and SEQ ID NO: 33.

OsLEA3a nucleic acids/genes and variants thereof may be suitable in practising the methods of the invention. The term "OsLEA3a nucleic acid/gene or variants thereof" as defined herein does not encompass nucleic acids encoding SEQ ID NO: 22 (LEA3a from *Hordeum vulgare*). Preferably, the variants of an OsLEA3a gene originate from rice. Variant OsLEA3a nucleic acid/genes include portions of an OsLEA3a nucleic acid/gene, splice variants, allelic variants and/or nucleic acids capable of hybridising with an OsLEA3a nucleic acid/gene.

Reference herein to a "nucleic acid sequence" is taken to mean a polymeric form of a deoxyribonucleotide or a ribonucleotide polymer of any length, either double- or single-stranded, or analogues thereof, that has the essential characteristic of a natural ribonucleotide in that it can hybridise to nucleic acid sequences in a manner similar to naturally occurring polynucleotides.

The term portion as defined herein refers to a piece of DNA encoding a polypeptide comprising two LEA4 domains corresponding to the Pfam accession PF02987 or the InterPro accession IPR004238 and the consensus signature sequence of (SEQ ID NO: 3). A portion may be prepared, for example, by making one or more deletions to an OsLEA3a nucleic acid. The portions may be used in isolated form or they may be fused to other coding (or non coding) sequences in order to, for example, produce a protein that combines several activities. When fused to other coding sequences, the resulting polypeptide produced upon translation may be bigger than that predicted for the OsLEA3a fragment. The portion is typically at least 100, 150 or 200 nucleotides in length, preferably at least 250, 300 or 350 nucleotides in length, more preferably at least 400, 450 or 500 nucleotides in length and most preferably at least 550 or 600 nucleotides in length. Preferably, the portion is a portion of a nucleic acid as represented by any one of SEQ ID NO: 1, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 23, SEQ ID NO: 25, SEQ ID NO: 27, SEQ ID NO: 29, SEQ ID NO: 31 and SEQ ID NO: 33. Most preferably the portion of an OsLEA3a nucleic acid is as represented by SEQ ID NO: 1.

The terms "fragment", "fragment of a sequence" or "part of a sequence" "portion" or "portion thereof" mean a truncated sequence of the original sequence referred to. The truncated sequence (nucleic acid or protein sequence) can vary widely in length; the minimum size being a sequence of sufficient size to provide a sequence with at least a comparable function and/or activity of the original sequence referred to or hybridising with the nucleic acid molecule of the invention or used in the process of the invention under stringent conditions, while the maximum size is not critical. In some applications, the maximum size usually is not substantially greater than that required to provide the desired activity and/or function(s) of the original sequence. A comparable function means at least 40%, 45% or 50%, preferably at least 60%, 70%, 80% or 90% or more of the function of the original sequence.

Another variant of an OsLEA3a nucleic acid/gene is a nucleic acid capable of hybridising under reduced stringency conditions, preferably under stringent conditions, with an OsLEA3a nucleic acid/gene as hereinbefore defined or with a portion as hereinbefore defined, which hybridising sequence preferably encodes a polypeptide comprising two LEA4 domains corresponding to the Pfam accession PF02987 or the InterPro accession IPR004238 and the OsLEA3a consensus signature sequence of (SEQ ID NO: 3). The hybridizing sequence is typically at least 300 nucleotides in length, preferably at least 400 nucleotides in length, more preferably at least 500 nucleotides in length and most preferably at least 600 nucleotides in length.

Preferably, the hybridising sequence is one that is capable of hybridising to a nucleic acid as represented by SEQ ID NO: 1, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 23, SEQ ID NO: 25, SEQ ID NO: 27, SEQ ID NO: 29, SEQ ID NO: 31, SEQ ID NO: 33, or to a portion of any of the aforementioned sequences, a portion being defined as above. Most preferably the hybridising sequence is capable of hybridising to SEQ ID NO: 1, or to portions (or probes) thereof. Methods for designing probes are well known in the art. Probes are generally less than 1000 bp, 900 bp, 800 bp, 700 bp, 600 bp in length, preferably less than 500 bp, 400 bp, 300 bp 200 bp or 100 bp in length. Commonly, probe lengths for DNA-DNA hybridizations such as Southern blotting, vary between 100 and 500 bp, whereas the hybridizing region in probes for DNA-DNA hybridizations such as in PCR amplification generally are shorter than 50 but longer than 10 nucleotides, preferably they are 15, 20, 25, 30, 35, 40, 45 or 50 bp in length.

The term "hybridisation" as defined herein is a process wherein substantially homologous complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids.

The term "stringency" refers to the conditions under which a hybridisation takes place. The stringency of hybridisation is influenced by conditions such as temperature, salt concentration, ionic strength and hybridisation buffer composition. Generally, low stringency conditions are selected to be about 30° C. lower than the thermal melting point ($T_m$) for the specific sequence at a defined ionic strength and pH. Medium stringency conditions are when the temperature is 20° C. below $T_m$, and high stringency conditions are when the temperature is 10° C. below $T_m$. High stringency hybridisation conditions are typically used for isolating hybridising sequences that have high sequence similarity to the target nucleic acid sequence. However, nucleic acids may deviate in sequence and still encode a substantially identical polypeptide, due to the degeneracy of the genetic code. Therefore medium stringency hybridisation conditions may sometimes be needed to identify such nucleic acid molecules.

The $T_m$ is the temperature under defined ionic strength and pH, at which 50% of the target sequence hybridises to a perfectly matched probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the $T_m$ decreases about 1° C. per % base mismatch. The $T_m$ may be calculated using the following equations, depending on the types of hybrids:

non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. A positive hybridisation gives a signal that is at least twice of that of the background. Generally, suitable stringent conditions for nucleic acid hybridisation assays or gene amplification detection procedures are as set forth above. More or less stringent conditions may also be selected. The skilled artisan is aware of various parameters which may be altered during washing and which will either maintain or change the stringency conditions.

For example, typical high stringency hybridisation conditions for DNA hybrids longer than 50 nucleotides encompass hybridisation at 65° C. in 1× SSC or at 42° C. in 1× SSC and 50% formamide, followed by washing at 65° C. in 0.3× SSC. Examples of medium stringency hybridisation conditions for DNA hybrids longer than 50 nucleotides encompass hybridisation at 50° C. in 4× SSC or at 40° C. in 6× SSC and 50% formamide, followed by washing at 50° C. in 2× SSC. The length of the hybrid is the anticipated length for the hybridising nucleic acid. When nucleic acids of known sequence are hybridised, the hybrid length may be determined by aligning the sequences and identifying the conserved regions described herein. 1× SSC is 0.15M NaCl and 15 mM sodium citrate; the hybridisations and washes may additionally include 5×Denhardt's reagent, 0.5-1.0% SDS, 100 µg/ml denatured, fragmented salmon sperm DNA, 0.5% sodium pyrophosphate.

For the purposes of defining the level of stringency, reference can be made to Sambrook et al. (2001) Molecular Cloning: a laboratory manual, 3rd Edition Cold Spring Harbor Laboratory Press, CSH, New York or to Current Protocols in Molecular Biology, John Wiley & Sons, N.Y. (1989 and yearly updates).

---

1) DNA-DNA hybrids (Meinkoth and Wahl, Anal. Biochem., 138: 267-284, 1984):
   $T_m = 81.5° C. + 16.6 \times \log_{10}[Na+]^a + 0.41 \times \%[G/C^b] - 500 \times [L^c]^{-1} - 0.61 \times \%\text{ formamide}$
2) DNA-RNA or RNA-RNA hybrids:
   $Tm = 79.8 + 18.5 (\log_{10}[Na+]^a) + 0.58 (\% G/C^b) + 11.8 (\% G/C^b)^2 - 820/L^c$
3) oligo-DNA or oligo-RNA$^d$ hybrids:
   For <20 nucleotides:      Tm = 2 ($l_n$)
   For 20-35 nucleotides:    Tm = 22 + 1.46 ($l_n$)

$^a$or for other monovalent cation, but only accurate in the 0.01-0.4 M range.
$^b$only accurate for % GC in the 30% to 75% range.
$^c$L = length of duplex in base pairs.
$^d$Oligo, oligonucleotide; $l_n$, effective length of primer = 2 × (no. of G/C) + (no. of A/T).

---

Non-specific binding may be controlled using any one of a number of known techniques such as, for example, blocking the membrane with protein containing solutions, additions of heterologous RNA, DNA, and SDS to the hybridisation buffer, and treatment with Rnase. For non-homologous probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridisation and which will either maintain or change the stringency conditions.

Besides the hybridisation conditions, specificity of hybridisation typically also depends on the function of post-hybridisation washes. To remove background resulting from Also useful in the methods of the invention are nucleic acids encoding homologues to the amino acid sequence represented by SEQ ID NO: 2.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A homologue may be in the form of a "substitutional variant" of a protein, i.e. where at least one residue in an amino acid sequence has been removed and a different residue inserted in its place. Amino acid substitutions are typically of single residues, but may be clustered depending upon functional constraints placed upon the polypeptide; insertions will usually be of the order of about 1 to 10 amino acid residues. Preferably, amino acid substitutions comprise conservative amino acid substitutions. To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company and Table 1 below).

TABLE 1

Examples of conserved amino acid substitutions

| Residue | Conservative Substitutions |
|---------|---------------------------|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

A homologue may also be in the form of an "insertional variant" of a protein, i.e. where one or more amino acid residues are introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag 100 epitope, c-myc epitope, FLAG®-epitope, lacZ, CMP (calmodulin-binding peptide), HA epitope, protein C epitope and VSV epitope.

Homologues in the form of "deletion variants" of a protein are characterised by the removal of one or more amino acids from a protein.

Amino acid variants of a protein (substitution-, deletion- and/or insertion-variants) may readily be made using peptide synthetic techniques well known in the art, such as solid phase peptide synthesis and the like, or by recombinant DNA manipulations. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Also useful in the methods of the invention are nucleic acids encoding derivatives of the polypeptide represented by SEQ ID NO 2 or orthologues or paralogues thereof. "Derivatives" include peptides, oligopeptides, polypeptides which may, compared to the amino acid sequence of the naturally-occurring form of the protein, such as the one presented in SEQ ID NO: 2, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein.

Another nucleic acid variant useful in the methods of the present invention is a splice variant encoding an OsLEA3a polypeptide as defined above. The term "splice variant" as used herein encompasses variants of a nucleic acid sequence in which selected introns and/or exons have been excised, replaced, displaced or added, or in which introns have been shortened or lengthened. Such variants will be ones in which the biological activity of the protein is substantially retained, this may be achieved by selectively retaining functional segments of the protein. Such splice variants may be found in nature or may be manmade. Methods for making such splice variants are known in the art. Preferred splice variants are splice variants of the nucleic acid encoding a polypeptide comprising the OsLEA3a consensus signature sequence (SEQ ID NO: 3). Preferably, the OsLEA3a polypeptide or the homologue thereof has at least 42%, 45%, 50%, 55%, 60%, 65%, 70%, 75%, 80%, 85%, 90%, 95%, 96%, 97%, 98% or 99% sequence identity to SEQ ID NO: 2. Further preferred are splice variants represented by SEQ ID NO: 1, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 23, SEQ ID NO: 25, SEQ ID NO: 27, SEQ ID NO: 29, SEQ ID NO: 31 and SEQ ID NO: 33. Most preferred is the splice variant represented by SEQ ID NO: 1.

Another nucleic acid variant useful in the methods of the present invention is an allelic variant of a nucleic acid encoding an OsLEA3a polypeptide as defined above. Preferably the allelic variant is a nucleic acid encoding a polypeptide comprising the OsLEA3a consensus signature sequence (SEQ ID NO: 3) and having at least 42%, 45%, 50%, 55%, 60%, 65%, 70%, 75%, 80%, 85%, 90%, 95%, 96%, 97%, 98% or 99% sequence identity to SEQ ID NO: 2. Preferably, the polypeptide encoded by the allelic variant is represented by SEQ ID NO: 1, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 23, SEQ ID NO: 25, SEQ ID NO: 27, SEQ ID NO: 29, SEQ ID NO: 31 and SEQ ID NO: 33. Most preferably, the allelic variant encoding the OsLEA3a polypeptide is represented by SEQ ID NO: 1. Allelic variants exist in nature, and encompassed within the methods of the present invention is the use of these natural alleles. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

A further nucleic acid variant useful in the methods of the invention is a nucleic acid variant obtained by gene shuffling. Gene shuffling or directed evolution may also be used to generate variants of OsLEA3 nucleic acids. This consists of iterations of DNA shuffling followed by appropriate screening and/or selection to generate variants of OsLEA3 nucleic acids or portions thereof having a modified biological activity (Castle et al., (2004) Science 304(5674): 1151-4; U.S. Pat. Nos. 5,811,238 and 6,395,547).

Furthermore, site-directed mutagenesis may be used to generate variants of OsLEA3 nucleic acids. Several methods are available to achieve site-directed mutagenesis; the most common being PCR based methods (Current Protocols in Molecular Biology. Wiley Eds.).

The OsLEA3a nucleic acid or variant thereof may be derived from any natural or artificial source. The nucleic acid/gene or variant thereof may be isolated from a microbial source, such as yeast or fungi, or from a plant, algae or animal (including human) source. This nucleic acid may be modified from its native form in composition and/or genomic environment through deliberate human manipulation. The nucleic acid is preferably of plant origin, whether from the same plant species (for example to the one in which it is to be introduced) or whether from a different plant species. The nucleic acid may be isolated from a monocotyledonous species, preferably from the family Poaceae, more preferably from *Oryza sativa*. Most preferably, the OsLEA3a nucleic acid is represented by SEQ ID NO: 1, and the OsLEA3a amino acid sequence is as represented by SEQ ID NO: 2.

Any reference herein to an OsLEA3a polypeptide is therefore taken to mean an OsLEA3a protein as defined above. Any nucleic acid encoding such an OsLEA3a protein is suitable for use in the methods of the invention.

According to a preferred aspect of the present invention, modulated, preferably increased expression of the OsLEA3a nucleic acid or variant thereof is envisaged. Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of an OsLEA3a nucleic acid or variant thereof. For example, endogenous promoters may be altered in vivo by mutation, deletion, and/or substitution (see, Kmiec, U.S. Pat. No. 5,565,350; Zarling et al., PCT/US93/03868), or isolated promoters may be introduced into a plant cell in the proper orientation and distance from a gene of the present invention so as to control the expression of the gene. Methods for reducing the expression of genes or gene products are well documented in the art.

The expression of a nucleic acid encoding an OsLEA3a polypeptide or a homologue thereof may be modulated by introducing a genetic modification (preferably in the locus of an OsLEA3a gene). The locus of a gene as defined herein is taken to mean a genomic region, which includes the gene of interest and 10 kb up- or down stream of the coding region.

The genetic modification may be introduced, for example, by any one (or more) of the following methods: T-DNA activation, TILLING, site-directed mutagenesis, directed evolution and homologous recombination or by introducing and expressing in a plant a nucleic acid encoding an OsLEA3a polypeptide or a homologue thereof. Following introduction of the genetic modification, there follows a step of selecting for modified expression of a nucleic acid encoding an OsLEA3a polypeptide or a homologue thereof, which modification in expression gives plants having increased yield.

T-DNA activation tagging (Hayashi et al. Science (1992) 1350-1353) involves insertion of T-DNA, usually containing a promoter (may also be a translation enhancer or an intron), in the genomic region of the gene of interest or 10 kb up- or down stream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to overexpression of genes near the inserted T-DNA. The resulting transgenic plants show dominant phenotypes due to overexpression of genes close to the introduced promoter. The promoter to be introduced may be any promoter capable of directing expression of a gene in the desired organism, in this case a plant. For example, constitutive, tissue-preferred, cell type-preferred and inducible promoters are all suitable for use in T-DNA activation.

A genetic modification may also be introduced in the locus of an OsLEA3a gene using the technique of TILLING (Targeted Induced Local Lesions In Genomes). This is a mutagenesis technology useful to generate and/or identify, and to eventually isolate mutagenised variants of an OsLEA3a nucleic acid with modulated expression and/or activity. TILLING also allows selection of plants carrying such mutant variants. These mutant variants may exhibit modified expression, either in strength or in location or in timing (if the mutations affect the promoter for example). These mutant variants may even exhibit higher OsLEA3a activity than that exhibited by the gene in its natural form. TILLING combines high-density mutagenesis with high-throughput screening methods. The steps typically followed in TILLING are: (a) EMS mutagenesis (Redei G P and Koncz C (1992) In Methods in *Arabidopsis* Research, Koncz C, Chua N H, Schell J, eds. Singapore, World Scientific Publishing Co, pp. 16-82; Feldmann et al., (1994) In Meyerowitz E M, Somerville C R, eds, *Arabidopsis*. Cold Spring Harbor Laboratory Press, Cold Spring Harbor, N.Y., pp 137-172; Lightner J and Caspar T (1998) In J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum et al., (2000) Nat Biotechnol 18: 455-457; reviewed by Stemple (2004) Nat Rev Genet 5(2): 145-50).

Site-directed mutagenesis may be used to generate variants of OsLEA3a nucleic acids. Several methods are available to achieve site-directed mutagenesis; the most common being PCR based methods (Current Protocols in Molecular Biology. Wiley Eds. www.4ulr.com/products/currentprotocols/index.html).

Directed evolution may also be used to generate variants of OsLEA3a nucleic acids. This consists of iterations of DNA shuffling followed by appropriate screening and/or selection to generate variants of OsLEA3a nucleic acids or portions thereof encoding OsLEA3a polypeptides or homologues or portions thereof having a modified biological activity (Castle et al., (2004) Science 304(5674): 1151-4; U.S. Pat. Nos. 5,811,238 and 6,395,547).

T-DNA activation, TILLING, site-directed mutagenesis and directed evolution are examples of technologies that enable the generation of novel alleles and OsLEA3a variants.

The effects of the invention may also be produced using homologous recombination, which allows introduction in a genome of a selected nucleic acid at a defined selected position. Homologous recombination is a standard technology used routinely in biological sciences for lower organisms such as yeast or the moss *Physcomitrella*. Methods for performing homologous recombination in plants have been described not only for model plants (Offring a et al. (1990) EMBO J 9(10): 3077-84) but also for crop plants, for example rice (Terada et al. (2002) Nat Biotech 20(10): 1030-4; Iida and Terada (2004) Curr Opin Biotech 15(2):132-8).

A preferred method for introducing a genetic modification (which in this case need not be in the locus of an OsLEA3a gene) is to introduce and express in a plant a nucleic acid encoding an OsLEA3a polypeptide or a homologue thereof, as defined above. The nucleic acid to be introduced into a plant may be a full-length nucleic acid or may be a portion or a hybridising sequence as hereinbefore defined.

The invention also provides genetic constructs and vectors to facilitate introduction and/or expression of the nucleotide sequences useful in the methods according to the invention.

Therefore, there is provided a gene construct comprising:
(i) an OsLEA3a nucleic acid or variant thereof, as defined hereinabove;
(ii) one or more control sequences capable of driving expression of the nucleic acid sequence of (i),
provided that said OsLEA3a nucleic acid or a variant does not encode SEQ ID NO: 22 (LEA3a protein of *Hordeum vulgare*).

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells. The invention therefore provides use of a gene construct as defined hereinabove in the methods of the invention.

Plants are transformed with a vector comprising the sequence of interest (i.e., a nucleic acid encoding an OsLEA3a polypeptide or homologue thereof). The skilled artisan is well aware of the genetic elements that must be present on the vector in order to successfully transform, select and propagate host cells containing the sequence of interest. The sequence of interest is operably linked to one or more control sequences (at least to a promoter). The terms "regulatory element", "control sequence" and "promoter" are all used interchangeably herein and are to be taken in a broad context to refer to regulatory nucleic acid sequences capable of effecting expression of the sequences to which they are ligated. The term "promoter" typically refers to a nucleic acid control sequence located upstream from the transcriptional start of a gene and which is involved in recognising and binding of RNA polymerase and other proteins, thereby directing transcription of an operably linked nucleic acid. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a -35 box sequence and/or -10 box transcriptional regulatory sequences. The term "regulatory element" also encompasses a synthetic fusion molecule or derivative that confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest.

Advantageously, any type of promoter may be used to drive expression of the nucleic acid sequence. The promoter may be an inducible promoter, i.e. having induced or increased transcription initiation in response to a chemical, environmental or physical stimulus. An example of an inducible promoter is a stress-inducible promoter, i.e. a promoter activated when a plant is exposed to various stress conditions, or a pathogen-induced promoter. Additionally or alternatively, the promoter may be a tissue-preferred promoter, i.e. one that is capable of preferentially initiating transcription in certain tissues, such as the leaves, roots, seed tissue etc; or may be a ubiquitous promoter, which is active in substantially all tissues or cells of an organism, or the promoter may be developmentally regulated, thereby being active during certain developmental stages or in parts of the plant that undergo developmental changes. Promoters able to initiate transcription in certain tissues only are referred to herein as "tissue-specific", similarly, promoters able to initiate transcription in certain cells only are referred to herein as "cell-specific".

Suitable promoters, which are functional in plants, are generally known. They may take the form of constitutive or inducible promoters. Suitable promoters can enable the developmental- and/or tissue-specific expression in multicellular eukaryotes; thus, leaf-, root-, flower-, seed-, stomata-, tuber- or fruit-specific promoters may advantageously be used in plants.

Different plant promoters usable in plants are promoters such as, for example, the USP, the LegB4-, the DC3 promoter or the ubiquitin promoter from parsley.

A "plant" promoter comprises regulatory elements, which mediate the expression of a coding sequence segment in plant cells. Accordingly, a plant promoter need not be of plant origin, but may originate from viruses or micro-organisms, in particular for example from viruses which attack plant cells.

The "plant" promoter can also originate from a plant cell, e.g. from the plant which is transformed with the nucleic acid sequence to be expressed in the inventive process and described herein. This also applies to other "plant" regulatory signals, for example in "plant" terminators.

For expression in plants, the nucleic acid molecule must, as described above, be linked operably to or comprise a suitable promoter which expresses the gene at the right point in time and in a cell- or tissue-specific manner. Usable promoters are constitutive promoters (Benfey et al., EMBO J. 8 (1989) 2195-2202), such as those which originate from plant viruses, such as 35S CAMV (Franck et al., Cell 21 (1980) 285-294), 19S CaMV (see also U.S. Pat. No. 5,352,605 and WO 84/02913), 34S FMV (Sanger et al., Plant. Mol. Biol., 14, 1990: 433-443), the parsley ubiquitin promoter, or plant promoters such as the Rubisco small subunit promoter described in U.S. Pat. No. 4,962,028 or the plant promoters PRP1 [Ward et al., Plant. Mol. Biol. 22 (1993)], SSU, PGEL1, OCS [Leisner (1988) Proc Natl Acad Sci USA 85(5): 2553-2557], lib4, usp, mas [Comai (1990) Plant Mol Biol 15 (3):373-381], STLS1, ScBV (Schenk (1999) Plant Mol Biol 39(6):1221-1230), B33, SAD1 or SAD2 (flax promoters, Jain et al., Crop Science, 39 (6), 1999: 1696-1701) or nos [Shaw et al. (1984)

Nucleic Acids Res. 12(20):7831-7846]. Further examples of constitutive plant promoters are the sugar beet V-ATPase promoters (WO 01/14572). Examples of synthetic constitutive promoters are the Super promoter (WO 95/14098) and promoters derived from G-boxes (WO 94/12015). If appropriate, chemically inducible promoters may furthermore also be used, compare EP-A 388186, EP-A 335528, WO 97/06268. Stable, constitutive expression of the proteins according to the invention a plant can be advantageous. However, inducible expression of the polypeptide of the invention is advantageous, if, for example, a late expression before the harvest is of advantage, as metabolic manipulation may lead to plant growth retardation.

The expression of plant genes can also be facilitated via a chemically inducible promoter (for a review, see Gatz 1997, Annu. Rev. Plant Physiol. Plant Mol. Biol., 48:89-108). Chemically inducible promoters are particularly suitable when it is desired to express the gene in a time-specific manner. Examples of such promoters are a salicylic acid inducible promoter (WO 95/19443), and abscisic acid-inducible promoter (EP 335 528), a tetracyclin-inducible promoter (Gatz et al. (1992) Plant J. 2, 397-404), a cyclohexanol- or ethanol-inducible promoter (WO 93/21334) or others as described herein.

Other suitable promoters are those which react to biotic or abiotic stress conditions, for example the pathogen-induced PRP1 gene promoter (Ward et al., Plant. Mol. Biol. 22 (1993) 361-366), the tomato heat-inducible hsp80 promoter (U.S. Pat. No. 5,187,267), the potato chill-inducible alpha-amylase promoter (WO 96/12814) or the wound-inducible pinII promoter (EP-A-0 375 091) or others as described herein.

Preferred promoters are in particular those which bring gene expression in tissues and organs, in seed cells, such as endosperm cells and cells of the developing embryo. Suitable promoters are the oilseed rape napin gene promoter (U.S. Pat. No. 5,608,152), the *Vicia faba* USP promoter (Baeumlein et al., Mol Gen Genet, 1991, 225 (3): 459-67), the *Arabidopsis oleosin* promoter (WO 98/45461), the *Phaseolus vulgatis* phaseolin promoter (U.S. Pat. No. 5,504,200), the *Brassica* Bce4 promoter (WO 91/13980), the bean arc5 promoter, the carrot DcG3 promoter, or the Legumin B4 promoter (LeB4; Baeumlein et al., 1992, Plant Journal, 2 (2): 233-9), and promoters which bring about the seed-specific expression in monocotyledonous plants such as maize, barley, wheat, rye, rice and the like. Advantageous seed-specific promoters are the sucrose binding protein promoter (WO 00/26388), the phaseolin promoter and the napin promoter. Suitable promoters which must be considered are the barley Ipt2 or Ipt1 gene promoter (WO 95/15389 and WO 95/23230), and the promoters described in WO 99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene and the rye secalin gene). Further suitable promoters are Amy32b, Amy 6-6 and Aleurain [U.S. Pat. No. 5,677,474], Bce4 (oilseed rape) [U.S. Pat. No. 5,530,149], glycinin (soya) [EP 571 741], phosphoenolpyruvate carboxylase (soya) [JP 06/62870], ADR12-2 (soya) [WO 98/08962], isocitrate lyase (oilseed rape) [U.S. Pat. No. 5,689,040] or α-amylase (barley) [EP 781 849]. Other promoters which are available for the expression of genes in plants are leaf-specific promoters such as those described in DE-A 19644478 or light-regulated promoters such as, for example, the pea petE promoter.

Further suitable plant promoters are the cytosolic FBPase promoter or the potato ST-LSI promoter (Stockhaus et al., EMBO J. 8, 1989, 2445), the *Glycine max* phosphoribosylpyrophosphate amidotransferase promoter (GenBank Accession No. U87999) or the node-specific promoter described in EP-A-0 249 676.

Preferably, the OsLEA3a nucleic acid or variant thereof is operably linked to a constitutive promoter. A constitutive promoter is transcriptionally active during most, but not necessarily all, phases of its growth and development and under most environmental conditions in at least one cell, tissue or organ. A preferred constitutive promoter is a constitutive promoter that is also substantially ubiquitously expressed. Further preferably, the constitutive promoter is derived from a plant, more preferably from a monocotyledonous plant. Most preferred is use of a GOS2 promoter (from rice, as represented by SEQ ID NO: 6). It should be clear that the applicability of the present invention is not restricted to the OsLEA3a nucleic acid represented by SEQ ID NO: 1, nor is the applicability of the invention restricted to expression of an OsLEA3a nucleic acid when driven by a GOS2 promoter. Examples of other constitutive promoters which may also be used to drive expression of an OsLEA3a nucleic acid are shown in Table 2 below.

TABLE 2

Examples of constitutive promoters

| Gene Source | Expression Pattern | Reference |
|---|---|---|
| Actin | Constitutive | McElroy et al, Plant Cell, 2: 163-171, 1990 |
| CAMV 35S | Constitutive | Odell et al, Nature, 313: 810-812, 1985 |
| CaMV 19S | Constitutive | Nilsson et al., Physiol. Plant. 100: 456-462, 1997 |
| GOS2 | Constitutive | de Pater et al, Plant J Nov; 2(6): 837-44, 1992 |
| Ubiquitin | Constitutive | Christensen et al, Plant Mol. Biol. 18: 675-689,1992 |
| Rice cyclophilin | Constitutive | Buchholz et al, Plant Mol Biol 25(5): 837-43, 1994 |
| Maize H3 histone | Constitutive | Lepetit et al, Mol. Gen. Genet. 231: 276-285, 1992 |
| Actin 2 | Constitutive | An et al, Plant J. 10(1); 107-121, 1996 |

Optionally, one or more terminator sequences (also a control sequence) may be used in the construct introduced into a plant. The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene. Additional regulatory elements may include transcriptional as well as translational enhancers. Those skilled in the art will be aware of terminator and enhancer sequences that may be suitable for use in performing the invention. Such sequences would be known or may readily be obtained by a person skilled in the art.

An intron sequence may also be added to the 5' untranslated region (UTR) or in the coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold, Buchman and Berg, Mol. Cell biol. 8:4395-4405 (1988); Callis et al., Genes Dev. 1:1183-1200 (1987). Such intron enhancement of gene expression is typically greatest when placed near the 5' end of the transcription unit. Use of the maize introns Adh1-S intron 1, 2, and 6, the Bronze-1 intron are known in the art. See generally, The Maize Handbook, Chapter 116, Freeling and Walbot, Eds., Springer, N.Y. (1994).

Other control sequences (besides promoter, enhancer, silencer, intron sequences, 3'UTR and/or 5'UTR regions) may be protein and/or RNA stabilizing elements. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

For the detection and/or selection of the successful transfer of the nucleic acid sequences as depicted in the sequence protocol and used in the process of the invention, it is advantageous to use marker genes (=reporter genes). These marker genes enable the identification of a successful transfer of the nucleic acid molecules via a series of different principles, for example via visual identification with the aid of fluorescence, luminescence or in the wavelength range of light which is discernible for the human eye, by a resistance to herbicides or antibiotics, via what is known as nutritive markers (auxotrophism markers) or antinutritive markers, via enzyme assays or via phytohormones. Examples of such markers which may be mentioned are GFP (=green fluorescent protein); the luciferin/luceferase system, the β-galactosidase with its coloured substrates, for example X-Gal, the herbicide resistances to, for example, imidazolinone, glyphosate, phosphinothricin or sulfonylurea, the antibiotic resistance to, for example, bleomycin, hygromycin, streptomycin, kanamycin, tetracyclin, chloramphenicol, ampicillin, gentamycin, geneticin (G418), spectinomycin or blasticidin, to mention only a few, nutritive markers such as the utilization of mannose or xylose, or antinutritive markers such as the resistance to 2-deoxyglucose. This list represents only a small number of possible markers. The skilled worker is very familiar with such markers. Different markers are preferred, depending on the organism and the selection method.

Therefore, the genetic construct may optionally comprise a selectable marker gene. As used herein, the term "selectable marker" or "selectable marker gene" includes any gene that confers a phenotype on a cell in which it is expressed to facilitate the identification and/or selection of cells that are transfected or transformed with a nucleic acid construct of the invention. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin), to herbicides (for example bar which provides resistance to Basta; aroA or gox providing resistance against glyphosate), or genes that provide a metabolic trait (such as manA that allows plants to use mannose as sole carbon source). Expression of visual marker genes result in the formation of colour (for example β-glucuronidase, GUS), luminescence (such as luciferase) or fluorescence (Green Fluorescent Protein, GFP, and derivatives thereof).

It is known that upon stable or transient integration of nucleic acids into plant cells, that only a minority of the cells takes up the foreign DNA and, if desired, integrates it into its genome, depending on the expression vector used and the transfection technique used. To identify and select these integrants, a gene coding for a selectable marker (as described above, for example resistance to antibiotics) is usually introduced into the host cells together with the gene of interest. Preferred selectable markers in plants comprise those conferring resistance to an herbicide such as glyphosate or glyphosinate. Other suitable markers are, for example, markers encoding genes involved in biosynthetic pathways of, for example, sugars or amino acids, such as β-galactosidase, ura3 or ilv2. Markers that encode genes such as luciferase, gfp or other fluorescence genes are likewise suitable. These and the aforementioned markers can be used in mutants in which these genes are not functional since, for example, they have been deleted by conventional methods. Furthermore, nucleic acid molecules encoding a selectable marker can be introduced into a host cell on the same vector that comprises the sequence encoding the polypeptides of the invention or used in the process, or else in a separate vector. Cells which have been stably transfected with the nucleic acid introduced can be identified for example by selection (for example, cells which have integrated the selectable marker survive whereas the other cells die).

Since the marker genes, particularly genes for resistance to antibiotics and herbicides, are no longer required or are undesired in the transgenic host cell once the nucleic acids have been introduced successfully, the process according to the invention for introducing the nucleic acids advantageously employs techniques which enable the removal or excision of these marker genes. One such a method is what is known as co-transformation. The co-transformation method employs two vectors simultaneously for the transformation, one vector bearing the nucleic acid according to the invention and a second bearing the marker gene(s). A large proportion of transformants receives or, in the case of plants, comprises (up to 40% of the transformants and above), both vectors. In case of transformation with Agrobacteria, the transformants usually receive only a part of the vector, the sequence flanked by the T-DNA, which usually represents the expression cassette. The marker genes can subsequently be removed from the transformed plant by performing crosses. In another method, marker genes integrated into a transposon are used for the transformation together with desired nucleic acid (known as the Ac/Ds technology). The transformants can be crossed with a transposase resource or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed which make possible, or facilitate, the detection of such events. A further advantageous method relies on what is known as recombination systems; whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible. Naturally, these methods can also be applied to microorganisms such as yeast, fungi or bacteria.

The present invention also encompasses plants, plant parts or plant cells obtainable by the methods according to the present invention. The present invention therefore provides plants obtainable by the method according to the present invention, which plants have introduced therein an OsLEA3a nucleic acid or variant thereof, as defined above.

The invention also provides a method for the production of transgenic plants having increased yield, comprising introduction and expression in a plant of an OsLEA3a nucleic acid or a variant thereof as defined above.

For the purposes of the invention, "transgenic", "transgene" or "recombinant" means with regard to, for example, a nucleic acid sequence, an expression cassette (=gene construct) or a vector comprising the nucleic acid sequence or an organism transformed with the nucleic acid sequences, expression cassettes or vectors according to the invention, all those constructions brought about by recombinant methods in which either a) the nucleic acid sequences according to the invention, or
    b) genetic control sequences which is operably linked with the nucleic acid sequence according to the invention, for example a promoter, or
    c) a) and b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide having LEA_4 domains or a homologue of such polypeptide—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is therefore understood as meaning, as above, that the nucleic acids used in the method of the invention are not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein.

Host plants for the nucleic acids or the vector used in the method according to the invention, the expression cassette or construct or vector are, in principle, advantageously all plants, which are capable of synthesizing the polypeptides used in the inventive method.

More specifically, the present invention provides a method for the production of transgenic plants having increased yield, which method comprises:

(i) introducing and expressing in a plant or plant cell an OsLEA3a nucleic acid or variant thereof; and
    (ii) cultivating the plant cell under conditions promoting plant growth and development.

The nucleic acid may be introduced directly into a plant cell or into the plant itself (including introduction into a tissue, organ or any other part of a plant). According to a preferred feature of the present invention, the nucleic acid is preferably introduced into a plant by transformation.

The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. In doing this the methods described for the transformation and regeneration of plants from plant tissues or plant cells are utilized for transient or stable transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Further advantageous transformation methods, in particular for plants, are known to the skilled worker and are described herein below.

Transformation of plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic rice plants are preferably produced via *Agrobacterium*-mediated transformation using any of the well known methods for rice transformation, such as described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, in particular of crop plants such as, by way of example, tobacco plants, for example by bathing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

Generally after transformation, plant cells or cell groupings are selected for the presence of one or more markers which are encoded by plant-expressible genes co-transferred with the gene of interest, following which the transformed material is regenerated into a whole plant.

As mentioned, Agrobacteria transformed with an expression vector according to the invention may also be used in the manner known per se for the transformation of plants such as experimental plants like *Arabidopsis* or crop plants, such as, cereals, maize, oats, rye, barley, wheat, soybean, rice, cotton, sugar beet, canola, sunflower, flax, hemp, potato, tobacco, tomato, carrot, bell peppers, oilseed rape, tapioca, cassava, arrow root, tagetes, alfalfa, lettuce and the various tree, nut, and grapevine species, in particular oil-containing crop plants such as soy, peanut, castor-oil plant, sunflower, maize, cotton, flax, oilseed rape, coconut, oil palm, safflower (*Carthamus tinctorius*) or cocoa beans, for example by bathing scarified leaves or leaf segments in an agrobacterial solution and subsequently culturing them on suitable media.

In addition to the transformation of somatic cells, which then has to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic [Feldman, K A and Marks M D (1987). Mol Gen Genet 208:274-289; Feldmann K (1992). In: C Koncz, N-H Chua and J Shell, eds, Methods in Arabidopsis Research. Word Scientific, Singapore, pp. 274-289]. Alternative methods are based on the repeated removal of the influorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, S J und Bent, A F (1998). The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3): 425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229).

The genetically modified plant cells can be regenerated via all methods with which the skilled worker is familiar. Suitable methods can be found in the abovementioned publications by S. D. Kung and R. Wu, Potrykus or Höfgen and Willmitzer.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement then being that progeny exhibit the same genotypic and/or phenotypic characteristic(s) as those produced by the parent in the methods according to the invention. The invention also includes host cells containing an isolated OsLEA3a nucleic acid or variant thereof. Preferred host cells according to the invention are plant cells. The invention also extends to harvestable parts of a plant such as, but not limited to seeds, leaves, fruits, flowers, stems, stem cultures, rhizomes, tubers and bulbs. The invention furthermore relates to products directly derived from a harvestable part of such a plant, such as dry pellets or powders, oil, fat and fatty acids, starch or proteins. These products also encompass the metabolites that are present at increased levels and that have an economic value.

The present invention also encompasses use of OsLEA3a nucleic acids or variants thereof and use of OsLEA3a polypeptides or homologues thereof.

One such use relates to improving the growth characteristics of plants, in particular in improving yield, especially seed yield. The seed yield may include one or more of the following: increased total weight of seeds, increased number of filled seeds and increased total number of seeds.

OsLEA3a nucleic acids or variants thereof, or OsLEA3a polypeptides or homologues thereof may find use in breeding programmes in which a DNA marker is identified which may be genetically linked to an OsLEA3a gene or variant thereof. The OsLEA3a nucleic acids/genes or variants thereof, or OsLEA3a polypeptides or homologues thereof may be used to define a molecular marker. This DNA or protein marker may then be used in breeding programmes to select plants having increased yield. The OsLEA3a gene or variant thereof may, for example, be a nucleic acid as represented by any one of SEQ ID NO: 1, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 23, SEQ ID NO: 25, SEQ ID NO: 27, SEQ ID NO: 29, SEQ ID NO: 31 and SEQ ID NO: 33.

Allelic variants of an OsLEA3a nucleic acid/gene may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give increased yield. Selection is typically carried out by monitoring growth performance of plants containing different allelic variants of the sequence in question, for example, different allelic variants of any one of SEQ ID NO: 1, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 23, SEQ ID NO: 25, SEQ ID NO: 27, SEQ ID NO: 29, SEQ ID NO: 31 and SEQ ID NO: 33. Growth performance may be monitored in a greenhouse or in the field. Further optional steps include crossing plants, in which the superior allelic variant was identified, with another plant. This could be used, for example, to make a combination of interesting phenotypic features.

An OsLEA3a nucleic acid or variant thereof may also be used as probes for genetically and physically mapping the genes that they are a part of, and as markers for traits linked to those genes. Such information may be useful in plant breeding in order to develop lines with desired phenotypes. Such use of OsLEA3a nucleic acids or variants thereof requires only a nucleic acid sequence of at least 15 nucleotides in length. The OsLEA3a nucleic acids or variants thereof may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the OsLEA3a nucleic acids or variants thereof. The resulting banding patterns may then be subjected to genetic analyses using computer programs such as MapMaker (Lander et al. (1987) Genomics 1: 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the OsLEA3a nucleic acid or variant thereof in the genetic map previously obtained using this population (Botstein et al. (1980) Am. J. Hum. Genet. 32: 314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridization (FISH) mapping (Trask (1991) Trends Genet. 7:149-154). Although current methods of FISH mapping favour use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acids. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having increased yield and altered metabolic profiles, as described hereinbefore. These advantageous growth characteristics may also be combined with other economically advantageous traits, such as further yield-enhancing traits, tolerance to various stresses, traits modifying various architectural features and/or biochemical and/or physiological features. The altered metabolic profile may find use as an alternative way for characterising plants having increased yield, which plants are produced by the methods of the present invention. The altered metabolic profile may also be used as a diagnostic tool or as a biomarker.

DESCRIPTION OF FIGURES

The present invention will now be described with reference to the following figures in which:

FIG. 1 shows the typical domain structure of OsLEA3a polypeptides. The protein encoded by SEQ ID NO: 2 comprises two LEA_4 domains (in bold); the 11-mer amino acid motifs are underlined. The most C-terminal domain (in italics) is a low complexity region.

FIG. 2 shows a binary vector p070, for expression in *Oryza sativa* of an *Arabidopsis thaliana* OsLEA3a coding sequence under the control of a GOS2 promoter (internal reference PRO0129).

FIG. 3 details examples of sequences useful in performing the methods according to the present invention. SEQ ID NO: 1 and 2 represent the OsLEA3a coding sequence and the deduced protein sequence. SEQ ID NO: 7 to 20 represent sequences of other rice LEA3a proteins and coding sequences, SEQ ID NO: 21 and 22 are sequences of barley HVA1. SEQ ID NO: 4 and 5 are the primer sequences used for cloning OsLEA3a. SEQ ID NO: 23 to 34 represent coding sequences and protein sequences of LEA3 homologues from non-rice species. SEQ ID NO: 35 and SEQ ID NO: 36 are variants of SEQ ID NO: 14 and SEQ ID NO: 34 respectively. SEQ ID NO: 3 represents the consensus signature sequence.

FIG. 4 represents a sequence identity/similarity table produced with MATGAT (BLOSUM62 matrix, gap opening penalty 11, gap extension penalty 1). Sequence identities are given in bold above the diagonal, sequence similarities are given below the diagonal. Full length protein sequences were used.

EXAMPLES

The present invention will now be described with reference to the following examples, which are by way of illustration alone.

DNA manipulation: unless otherwise stated, recombinant DNA techniques are performed according to standard protocols such as those described in Sambrook (Molecular Cloning: a laboratory manual, 3rd Edition Cold Spring Harbor Laboratory Press, CSH, New York, 2001) or in Volumes 1 and 2 of Ausubel et al. (1994), Current Protocols in Molecular Biology, Current Protocols (www.4ulr.com/products/currentprotocols/index.html). Standard materials and methods for plant molecular work are described in Plant Molecular Biology Labfax (1993) by R. D. D. Croy, published by BIOS Scientific Publications Ltd (UK) and Blackwell Scientific Publications (UK).

Example 1

Gene Cloning of OsLEA3a

The *Oryza sativa* OsLEA3a encoding gene was amplified by PCR using as template an *Oryza sativa japonica* cv Nipponbare seedling cDNA library (Invitrogen, Paisley, UK). After reverse transcription of RNA extracted from seedlings, the cDNAs were cloned into pCMV Sport 6.0. Average insert size of the bank was 1.5 kb, and the original number of clones was of $1.59 \times 10^7$ cfu. Original titer was determined to be $9.6 \times 10^5$ cfu/ml, after a first amplification of $6 \times 10^{11}$ cfu/ml. After plasmid extraction, 200 ng of template was used in a 50 µl PCR mix. Primers prm06120 (sense, AttB1 site in italic, start codon in bold: 5'-ggggacaagtttgtacaaaaaagcaggcttaaacaatggcttcccaccagga-3') (SEQ ID NO 4) and prm06121 (reverse, complementary, AttB2 site in italic, stop codon in bold: 5'-ggggaccactttgtacaagaaagctgggtaaatcattcacggcgtctagt-3') (SEQ ID NO 5), which include the AttB sites for Gateway recombination, were used for PCR amplification. PCR was performed using Hifi Taq DNA polymerase in standard conditions. A PCR fragment of the expected size was amplified and purified also using standard methods. The first step of the Gateway procedure, the BP reaction, was then performed, during which the PCR fragment recombines in vivo with the pDONR201 plasmid to produce, according to the Gateway terminology, an "entry clone", p06. Plasmid pDONR201 was purchased from Invitrogen, as part of the Gateway® technology.

Example 2

Vector Construction

The entry clone p06 were subsequently used in an LR reaction with p00640, a destination vector used for *Oryza sativa* transformation. This vector contains as functional elements within the T-DNA borders: a plant selectable marker; a screenable marker expression cassette; and a Gateway cassette intended for LR in vivo recombination with the sequence of interest already cloned in the entry clone. A rice GOS2 promoter (SEQ ID NO: 6) for constitutive expression (PRO0129) was located upstream of this Gateway cassette.

After the LR recombination step, the resulting expression vector, p07 (FIG. 1), was transformed into *Agrobacterium* strain LBA4044 using heat shock or electroporation protocols. Transformed colonies were grown on YEP media and selected by respective antibiotics for two days at 28° C. These *Agrobacterium* cultures were used for the plant transformation described in Example 3.

Other *Agrobacterium tumefaciens* strains can be used for plant transformation and are well known in the art. Examples of such strains are C58C1 or EHA105.

Example 3

Plant Transformation

Rice Transformation

The *Agrobacterium* containing the expression vector was used to transform *Oryza sativa* plants. Mature dry seeds of the rice japonica cultivar Nipponbare were dehusked. Sterilization was carried out by incubating for one minute in 70% ethanol, followed by 30 minutes in 0.2% $HgCl_2$, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity).

Agrobacterium strain LBA4404 containing the expression vector was used for cocultivation. Agrobacterium was inoculated on AB medium with the appropriate antibiotics and cultured for 3 days at 28° C. The bacteria were then collected and suspended in liquid co-cultivation medium to a density (OD600) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

Approximately 35 independent T0 rice transformants were generated for one construct. The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodges 1996, Chan et al. 1993, Hiei et al. 1994).

Corn Transformation

Transformation of maize (Zea mays) is performed with a modification of the method described by Ishida et al. (1996) Nature Biotech 14(6): 745-50. Transformation is genotype-dependent in corn and only specific genotypes are amenable to transformation and regeneration. The inbred line A188 (University of Minnesota) or hybrids with A188 as a parent are good sources of donor material for transformation, but other genotypes can be used successfully as well. Ears are harvested from corn plant approximately 11 days after pollination (DAP) when the length of the immature embryo is about 1 to 1.2 mm. Immature embryos are cocultivated with Agrobacterium tumefaciens containing the expression vector, and transgenic plants are recovered through organogenesis. Excised embryos are grown on callus induction medium, then maize regeneration medium, containing the selection agent (for example imidazolinone but various selection markers can be used). The Petri plates are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Wheat Transformation

Transformation of wheat is performed with the method described by Ishida et al. (1996) Nature Biotech 14(6): 745-50. The cultivar Bobwhite (available from CIMMYT, Mexico) is commonly used in transformation. Immature embryos are co-cultivated with Agrobacterium tumefaciens containing the expression vector, and transgenic plants are recovered through organogenesis. After incubation with Agrobacterium, the embryos are grown in vitro on callus induction medium, then regeneration medium, containing the selection agent (for example imidazolinone but various selection markers can be used). The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Soybean Transformation

Soybean is transformed according to a modification of the method described in the Texas A&M U.S. Pat. No. 5,164,310. Several commercial soybean varieties are amenable to transformation by this method. The cultivar Jack (available from the Illinois Seed foundation) is commonly used for transformation. Soybean seeds are sterilised for in vitro sowing. The hypocotyl, the radicle and one cotyledon are excised from seven-day old young seedlings. The epicotyl and the remaining cotyledon are further grown to develop axillary nodes. These axillary nodes are excised and incubated with Agrobacterium tumefaciens containing the expression vector. After the cocultivation treatment, the explants are washed and transferred to selection media. Regenerated shoots are excised and placed on a shoot elongation medium. Shoots no longer than 1 cm are placed on rooting medium until roots develop. The rooted shoots are transplanted to soil in the greenhouse. T1 seeds are produced from plants that exhibit tolerance to the selection agent and that contain a single copy of the T-DNA insert.

Rapeseed/Canola Transformation

Cotyledonary petioles and hypocotyls of 5-6 day old young seedling are used as explants for tissue culture and transformed according to Babic et al. (1998, Plant Cell Rep 17: 183-188). The commercial cultivar Westar (Agriculture Canada) is the standard variety used for transformation, but other varieties can also be used. Canola seeds are surface-sterilized for in vitro sowing. The cotyledon petiole explants with the cotyledon attached are excised from the in vitro seedlings, and inoculated with Agrobacterium (containing the expression vector) by dipping the cut end of the petiole explant into the bacterial suspension. The explants are then cultured for 2 days on MSBAP-3 medium containing 3 mg/l BAP, 3% sucrose, 0.7% Phytagar at 23° C., 16 hr light. After two days of co-cultivation with Agrobacterium, the petiole explants are transferred to MSBAP-3 medium containing 3 mg/l BAP, cefotaxime, carbenicillin, or timentin (300 mg/l) for 7 days, and then cultured on MSBAP-3 medium with cefotaxime, carbenicillin, or timentin and selection agent until shoot regeneration. When the shoots are 5-10 mm in length, they are cut and transferred to shoot elongation medium (MSBAP-0.5, containing 0.5 mg/l BAP). Shoots of about 2 cm in length are transferred to the rooting medium (MS0) for root induction. The rooted shoots are transplanted to soil in the greenhouse. T1 seeds are produced from plants that exhibit tolerance to the selection agent and that contain a single copy of the T-DNA insert.

Alfalfa Transformation

A regenerating clone of alfalfa (*Medicago sativa*) is transformed using the method of (McKersie et al., 1999 Plant Physiol 119: 839-847). Regeneration and transformation of alfalfa is genotype dependent and therefore a regenerating plant is required. Methods to obtain regenerating plants have been described. For example, these can be selected from the cultivar Rangelander (Agriculture Canada) or any other commercial alfalfa variety as described by Brown DCW and A Atanassov (1985. Plant Cell Tissue Organ Culture 4: 111-112). Alternatively, the RA3 variety (University of Wisconsin) has been selected for use in tissue culture (Walker et al., 1978 Am J Bot 65:654-659). Petiole explants are cocultivated with an overnight culture of *Agrobacterium tumefaciens* C58C1 pMP90 (McKersie et al., 1999 Plant Physiol 119: 839-847) or LBA4404 containing the expression vector. The explants are cocultivated for 3 d in the dark on SH induction medium containing 288 mg/L Pro, 53 mg/L thioproline, 4.35 g/L K2SO4, and 100 μm acetosyringinone. The explants are washed in half-strength Murashige-Skoog medium (Murashige and Skoog, 1962) and plated on the same SH induction medium without acetosyringinone but with a suitable selection agent and suitable antibiotic to inhibit *Agrobacterium* growth. After several weeks, somatic embryos are transferred to BOi2Y development medium containing no growth regulators, no antibiotics, and 50 g/L sucrose. Somatic embryos are subsequently germinated on half-strength Murashige-Skoog medium. Rooted seedlings were transplanted into pots and grown in a greenhouse. T1 seeds are produced from plants that exhibit tolerance to the selection agent and that contain a single copy of the T-DNA insert.

Example 4

Evaluation and Results of OsLEA3a Expression in Rice Under the Control of the Rice GOS2 Promoter Approximately 15 to 20 independent T0 rice transformants were generated. The primary transformants were transferred from a tissue culture chamber to a greenhouse for growing and harvest of T1 seed. Five events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. The selected T1 plants were transferred to a greenhouse. Each plant received a unique barcode label to link unambiguously the phenotyping data to the corresponding plant. The selected T1 plants were grown on soil in 10 cm diameter pots under the following environmental settings: photoperiod=11.5 h, daylight intensity=30,000 lux or more, daytime temperature=28° C., night time temperature=22° C., relative humidity=60-70%. Transgenic plants and the corresponding nullizygotes were grown side-by-side at random positions. Care was taken that the plants were not subjected to any stress. From the stage of sowing until the stage of maturity the plants were passed several times through a digital imaging cabinet. At each time point digital images (2048×1536 pixels, 16 million colours) were taken of each plant from at least 6 different angles.

The above ground area (corresponding to the leafy biomass) was determined by counting the total number of pixels from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground.

The mature primary panicles were harvested, bagged, barcode-labelled and then dried for three days in the oven at 37° C. The panicles were then threshed and all the seeds collected. The filled husks were separated from the empty ones using an air-blowing device. After separation, both seed lots were then counted using a commercially available counting machine. The empty husks were discarded. The filled husks were weighed on an analytical balance and the cross-sectional area of the seeds was measured using digital imaging. This procedure resulted in the set of the following seed-related parameters:

The number of filled seeds was determined by counting the number of filled husks that remained after the separation step. The total seed yield (total seed weight) was measured by weighing all filled husks harvested from a plant. Total seed number per plant was measured by counting the number of husks harvested from a plant. Thousand Kernel Weight (TKW) is extrapolated from the number of filled seeds counted and their total weight. Harvest index is defined as the ratio between the total seed weight and the above-ground area ($mm^2$), multiplied by a factor $10^6$. These parameters were derived in an automated way from the digital images using image analysis software and were analysed statistically. Individual seed parameters (including width, length, area, weight) were measured using a custom-made device consisting of two main components, a weighing and imaging device, coupled to software for image analysis.

A two factor ANOVA (analyses of variance) corrected for the unbalanced design was used as statistical model for the overall evaluation of plant phenotypic characteristics. An F-test was carried out on all the parameters measured of all the plants of all the events transformed with that gene. The F-test was carried out to check for an effect of the gene over all the transformation events and to verify for an overall effect of the gene, also named herein "global gene effect". If the value of the F test shows that the data are significant, than it is concluded that there is a "gene" effect, meaning that not only presence or the position of the gene is causing the effect. The threshold for significance for a true global gene effect is set at 5% probability level for the F test.

To check for an effect of the genes within an event, i.e., for a line-specific effect, a t-test was performed within each event using data sets from the transgenic plants and the corresponding null plants. "Null plants" or "null segregants" or "nullizygotes" are the plants treated in the same way as the transgenic plant, but from which the transgene has segregated. Null plants can also be described as the homozygous negative transformed plants. The threshold for significance for the t-test is set at 10% probability level. The results for some events can be above or below this threshold. This is based on the hypothesis that a gene might only have an effect in certain positions in the genome, and that the occurrence of this position-dependent effect is not uncommon. This kind of gene effect is also named herein a "line effect of the gene". The p-value is obtained by comparing the t-value to the t-distribution or alternatively, by comparing the F-value to the F-distribution. The p-value then gives the probability that the null hypothesis (i.e., that there is no effect of the transgene) is correct.

The data obtained for OsLEA3a in the first experiment were confirmed in a second experiment with T2 plants. Four lines that had the correct expression pattern were selected for further analysis. Seed batches from the positive plants (both hetero- and homozygotes) in T1, were screened by monitoring marker expression. For each chosen event, the heterozygote seed batches were then retained for T2 evaluation. Within each seed batch an equal number of positive and negative plants were grown in the greenhouse for evaluation.

A total number of 120 OsLEA3a transformed plants were evaluated in the T2 generation, that is 30 plants per event of which 15 positives for the transgene, and 15 negatives.

Because two experiments with overlapping events had been carried out, a combined analysis was performed. This is useful to check consistency of the effects over the two experiments, and if this is the case, to accumulate evidence from both experiments in order to increase confidence in the conclusion. The method used was a mixed-model approach that takes into account the multilevel structure of the data (i.e. experiment-event-segregants). P-values are obtained by comparing likelihood ratio test to chi square distributions.

Example 5

Evaluation of OsLEA3a Transformants: Measurement of Yield-Related Parameters

Upon analysis of the seeds as described above, the inventors found that plants transformed with the OsLEA3a gene construct had a higher seed yield, expressed as total number of seeds (11% increase), number of filled seeds (21% increase) and total weight of seeds (25% increase), compared to plants lacking the OsLEA3a transgene.

The results obtained for plants in the T1 generation are summarised in Table 3:

TABLE 3

|  | % difference | p-value |
| --- | --- | --- |
| Nr filled seeds | +21 | 0.0398 |
| Total weight seeds | +25 | 0.0296 |

These positive results were again obtained in the T2 generation. The T2 data were re-evaluated in a combined analysis with the results for the T1 generation, and the obtained p-values showed that the observed effects were highly significant.

Example 6

Metabolic Analysis of Transformed Plants

Plants transformed with OsLEA3a (as described in Example 1) were grown in the greenhouse as described in Example 4. The modified composition in accordance with the invention, with respect to various metabolites, was determined by the following procedure.

a) Homogenization of the Samples

Ten to thirty rice kernels were transferred into plastic tubes (Eppendorf, Safe-Lock, 2 mL) and homogenized with a stainless steel ball in a ball-mill (Retsch) under cooling with liquid nitrogen.

b) Lyophilization

During the experiment, care was taken that the samples either remained in a deep-frozen state (below −40° C.) or were freed from water by lyophilization of the homogenized material until the first contact with solvents. The samples were transferred in a pre-cooled (−40° C.) freeze dryer. The initial temperature during the main drying phase was −35° C. and the pressure was 0.120 mbar. During the process of drying, the parameters were altered, following a pressure and temperature program. The final temperature after 12 hours was +30° C. and the final pressure was 0.001 to 0.004 mbar. Upon switching off the vacuum pump and the refrigerating machine, the system was flushed with air (dried via a drying tube) or argon.

c) Extraction

Immediately after the lyophilization apparatus had been flushed, the tubes with the lyophilized plant material were tightly sealed to protect the material from air humidity. For the extraction, a portion of 50 mg dried homogenized plant material was weighed in glass fibre extraction thimbles and transferred into 5 ml extraction cartridges of the ASE device (Accelerated Solvent Extractor ASE 200 with Solvent Controller and AutoASE software (DIONEX)). The 24 sample positions of an ASE device (Accelerated Solvent Extractor ASE 200 with Solvent Controller and AutoASE software (DIONEX)) were filled with plant samples, including some samples for quality control testing.

Polar substances were extracted with approximately 10 ml of methanol/water (80/20, v/v) at 70° C. and a pressure of 140 bar, 5 minutes heating-up phase, 1 minute static extraction. The more lipophilic substances were extracted with approximately 10 ml of methanol/dichloromethane (40/60, v/v) at 70° C. and a pressure of 140 bar, 5 minute heating-up phase, 1 minute static extraction. The two solvent mixtures were pooled into the same glass tubes (centrifuge tubes, 50 ml, equipped with screw cap and pierceable septum for the ASE (DIONEX)). The solution was supplemented with commercially available internal standards, such as ribitol, L-glycine-2,2-$d_2$, L alanine-2,3,3,3-$d_4$, methionine-$d_3$, Arginine_($^{13}$C), Tryptophan-$d_5$, α-methylglucopyranoside methyl nonadecanoate, methyl undecanoate, methyl tridecanoate, methyl pentadecanoate and methyl nonacosanoate. The total extract was mixed with 8 ml of water. The solid residue of the plant sample and the extraction sleeve were discarded. The extract was shaken and then centrifuged for 5 to 10 minutes at minimally 1400 g in order to accelerate phase separation. 1 ml of the supernatant methanol/water phase ("polar phase", colorless) was removed for gas chromatographic (GC) analysis, and 1 ml was removed for liquid chromatographic (LC) analysis. The remainder of the methanol/water phase was discarded. Similarly, 0.75 ml of the organic phase ("lipid phase", dark green) was removed for the further GC analysis and 0.75 ml was removed for LC analysis. All these samples were evaporated to dryness using the IR Dancer infrared vacuum evaporator (Hettich). The maximum temperature during the evaporation process did not exceed 40° C. Pressure in the apparatus was 10 mbar or lower.

d) Processing the Lipid and Polar Phase for LC/MS or LC/MS/MS Analysis

The lipid extract and polar extract, which had been evaporated to dryness, were taken up in mobile phase for LC analysis.

e) LC-MS Analysis

The LC part was carried out on a commercially available LC/MS system from Agilent Technologies, USA. From the polar extracts 10 μl were injected into the system at a flow rate of 200 μl/min. The separation column (Reversed Phase C18) was maintained at 15° C. during chromatography. For lipid extracts, 5 μl were injected into the system at a flow rate of 200 μl/min. The separation column (Reversed Phase C18) was maintained at 30° C. HPLC was performed with gradient elution. The mass spectrometric analysis was performed on a Applied Biosystems API 4000 triple quadrupole instrument with turbo ion spray source. For polar extracts, the instrument measured in negative ion mode in fullscan mode from 100-

1000 amu; whereas for the lipid extracts the instrument measured in positive ion mode in fullscan mode from 100-1000 amu.

f) Derivatization of the Lipid Phase for the GC/MS Analysis

A mixture of 140 µl of chloroform, 37 µl of hydrochloric acid (37% by weight HCl in water), 320 µl of methanol and 20 µl of toluene was added to the evaporated extract for the transmethanolysis. The vessel was sealed tightly and heated for 2 hours at 100° C., while shaking. The solution was subsequently evaporated until the residue was dried completely. The methoximation of the carbonyl groups was carried out by reaction with methoxyamine hydrochloride (5 mg/ml in pyridine, 100 ml for 1.5 hours at 60° C.) in a tightly sealed vessel. 20 µl of a solution of odd-numbered, straight-chain fatty acids (solution of each 0.3 mg/mL of fatty acids from 7 to 25 carbon atoms and each 0.6 mg/mL of fatty acids with 27, 29 and 31 carbon atoms in 3/7 (v/v) pyridine/toluene) were added as time standards. Finally, the derivatization with 100 µl of N methyl-N-(trimethylsilyl)-2,2,2-trifluoroacetamide (MSTFA) was carried out for 30 minutes at 60° C., again in the tightly sealed vessel. The final volume before injection into the GC was 220 µl.

g) Derivatization of the Polar Phase for the GC/MS Analysis

The methoximation of the carbonyl groups was carried out by reaction with methoxyamine hydrochloride (5 mg/ml in pyridine, 50 ml for 1.5 hours at 60° C.) in a tightly sealed vessel. 10 µl of a solution of odd-numbered, straight-chain fatty acids (solution of each 0.3 mg/mL of fatty acids from 7 to 25 carbon atoms and each 0.6 mg/mL of fatty acids with 27, 29 and 31 carbon atoms in 3/7 (v/v) pyridine/toluene) were added as time standards. Finally, the derivatization with 50 µl of N methyl-N-(trimethylsilyl)-2,2,2-trifluoroacetamide (MSTFA) was carried out for 30 minutes at 60° C., again in the tightly sealed vessel. The final volume before injection into the GC was 110 µl.

h) GC-MS Analysis

The GC-MS system consisted of an Agilent 6890 GC coupled to an Agilent 5973 MSD. The autosamplers were CompiPal or GCPal from CTC. For the analysis commercially available capillary separation columns (30 m×0.25 mm×0.25 µm) with different poly-methyl-siloxane stationary phases containing 0% up to 35% of aromatic moieties were used, depending on the sample material and the fractions from the phase separation step to be analysed (for example: DB-1 ms, HP-5 ms, DB-XLB, DB-35 ms, Agilent Technologies). Up to 1 µL of the final volume was injected splitless and with an oven temperature gradient from 70° C. to 340° C. with different heating rates depending on the sample material and fraction from the phase separation step, in order to achieve a sufficient chromatographic separation and number of scans within each analyte peak. Usual GC-MS standard conditions, for example constant flow with nominal 1 to 1.7 ml/min. and helium as the mobile phase gas were used. Ionisation was done by electron impact with 70 eV, scanning within a m/z range from 15 to 600 with scan rates from 2.5 to 3 scans/sec and standard tune conditions.

i) Analysis of the Various Plant Samples

The samples were measured in individual series of 20 plant samples each. In the experiments each series contained at least 3 replicates per transgenic line plus at least 3 plants of the respective null-segregant line as controls. The peak areas for each analyte were adjusted for the dry weight established for the plant (normalized area). Ratio values were calculated by further normalization to the control. In the experiments ratio values were calculated by dividing the normalized area by the mean of the corresponding data of the control group in the same series. The values obtained are referred to as ratio_by_control. They are comparable among series and indicate how much the analyte concentration in the transgenic plant differs from the control group, which are the plants of the respective null-segregant lines in a given series. Appropriate controls were done at forehand to prove that the vector and transformation procedure itself had no significant influence on the metabolic composition of the plants.

The results of the different plant analyses can be seen from the following table 4:

TABLE 4

Results of the analysis of seeds from OsLEA3a transformants, the min_ratio and max_ratio are relative to the control plants

| METABOLITE CLASS | METABOLITE | MIN RATIO | MAX RATIO | METHOD |
| --- | --- | --- | --- | --- |
| Amino Acids Aromatic-Shikimate Family | Tryptophane | 2.4 | 2.6 | LC |
| Amino Acids Aromatic-Shikimate Family | Tryptophane | 1.6 | 1.8 | GC |
| Amino Acids Aromatic-Shikimate Family | Phenylalanine | 4.4 | 4.8 | LC |
| Amino Acids Aromatic-Shikimate Family | Phenylalanine | 4.2 | 4.3 | GC |
| Amino Acids Aromatic-Shikimate Family | Tyrosine | 3.6 | 4.0 | LC |
| Amino Acids Aromatic-Shikimate Family | Tyrosine | 3.9 | 3.9 | GC |
| Amino Acids Aromatic-Shikimate Family | Shikimic Acid | 5.5 | 6.3 | GC |
| Amino Acids Aromatic-Shikimate Family | 3,4-Dihydroxyphenylalanine (DOPA) | 0.7 | 0.8 | GC |
| Amino Acids Asp Family | Methionine | 2.1 | 2.4 | LC |
| Amino Acids Asp Family | Methionine | 3.1 | 3.4 | GC |
| Amino Acids Asp Family | Threonine | 5.5 | 6.5 | LC |
| Amino Acids Asp Family | Homoserine | 2.5 | 2.6 | GC |
| Amino Acids Asp Family | Aspartic acid | 3.2 | 3.3 | GC |
| Amino Acids Asp Family | Isoleucine | 5.6 | 5.6 | GC |
| Amino Acids Glu Family | Proline | 1.6 | 2.8 | LC |
| Amino Acids Glu Family | Proline | 2.4 | 2.4 | GC |
| Amino Acids Glu Family | Glutamine | 6.4 | 7.7 | LC |
| Amino Acids Glu Family | Glutamine | 5.0 | 5.9 | GC |

TABLE 4-continued

Results of the analysis of seeds from OsLEA3a transformants, the min_ratio and max_ratio are relative to the control plants

| METABOLITE CLASS | METABOLITE | MIN RATIO | MAX RATIO | METHOD |
|---|---|---|---|---|
| Amino Acids Glu Family | Glutamate | 1.9 | 2.1 | LC |
| Amino Acids Glu Family | Glutamate | 2.4 | 2.6 | GC |
| Amino Acids Glu Family | 5-Oxoproline | 3.5 | 3.6 | GC |
| Amino Acids Photorespiration and related | Cysteine | 1.9 | 2.2 | GC |
| Amino Acids Photorespiration and related | Serine | 2.4 | 2.4 | GC |
| Amino Acids Pyr Family | Alanine | 2.7 | 2.7 | GC |
| Amino Acids Pyr Family | Leucine | 4.1 | 4.5 | GC |
| Amino Acids Pyr Family | Valine | 5.9 | 6.1 | GC |
| Carotenoids | beta-Carotene | 1.8 | 3.1 | LC |
| Carotenoids | Cryptoxanthin | 6.7 | 9.5 | LC |
| Carotenoids | Lycopene | 4.2 | 19.3 | LC |
| Carotenoids | Zeaxanthin | 3.4 | 8.8 | LC |
| Carotenoids | Violaxanthin | 1.8 | 2.2 | LC |
| Carotenoids | Isopentenyl Pyrophosphate | 2.3 | 2.7 | LC |
| Cofactors | Coenzyme Q9 | 1.3 | 1.5 | LC |
| Fatty Acid metabolism and related | 2-Hydroxy-palmitic acid | 0.8 | 0.9 | GC |
| Fatty Acid metabolism and related | C16: trans[9]1 | 0.8 | 0.9 | GC |
| Fatty Acid metabolism and related | Eicosanoic acid (C20: 0) | 0.7 | 0.8 | GC |
| Fatty Acid metabolism and related | Eicosatrienoic acid (C20: [11, 14, 17]3) | 0.3 | 0.4 | GC |
| Fatty Acid metabolism and related | Stearicacid (C18: 0) | 0.8 | 0.9 | GC |
| Organic Acids | Citrate | 1.5 | 1.9 | LC |
| Organic Acids | Citrate | 3.0 | 3.5 | GC |
| Organic Acids | Fumarate | 4.0 | 4.7 | LC |
| Organic Acids | Fumarate | 9.0 | 10.0 | GC |
| Organic Acids | Malate | 6.4 | 7.6 | LC |
| Organic Acids | Malate | 17.9 | 20.0 | GC |
| Organic Acids | Pyruvate | 2.1 | 2.5 | LC |
| Organic Acids | Succinate | 3.9 | 4.5 | LC |
| Organic Acids | Succinate | 3.6 | 3.8 | GC |
| Organic Acids | Glyceric acid | 2.5 | 2.6 | GC |
| Organic Acids | Glycolic acid | 1.4 | 1.7 | LC |
| Organic Acids | Ribonic acid | 1.9 | 2.2 | GC |
| Organic Acids | Trihydroxybutanoic acid, putative | 3.0 | 3.2 | GC |
| Organic Acids | Nicotinic Acid | 1.8 | 1.9 | GC |
| Others | gamma-Aminobutyric acid (GABA) | 18.6 | 20.6 | GC |
| Phenolics | Ferulic acid | 2.5 | 2.7 | LC |
| Phenolics | Ferulic acid | 1.4 | 1.7 | GC |
| Phenolics | Quinic acid | 8.3 | 8.5 | GC |
| Phytohormones | Jasmonic acid | 6.3 | 10.9 | LC |
| Phytohormones | Salicylic acid | 1.7 | 1.8 | LC |
| Phytosterols | Cholesterol | 1.3 | 1.5 | GC |
| Phytosterols | Stigmastanol | 1.0 | 1.2 | GC |
| Sugar metabolism | Arabinose | 1.3 | 1.3 | GC |
| Sugar metabolism | Fructose | 3.3 | 3.6 | GC |
| Sugar metabolism | Glucose | 1.5 | 1.8 | GC |
| Sugar metabolism | Lyxose | 2.6 | 2.7 | GC |
| Sugar metabolism | Maltose | 2.0 | 2.5 | GC |
| Sugar metabolism | Melibiose | 1.8 | 2.3 | GC |
| Sugar metabolism | myo-Inositol | 4.5 | 4.7 | GC |
| Sugar metabolism | Raffinose | 3.3 | 3.6 | GC |
| Sugar metabolism | Stachyose | 1.6 | 2.8 | LC |
| Sugar metabolism | Sucrose | 0.8 | 0.8 | GC |
| Sugar metabolism | Erythrose | 0.7 | 0.7 | GC |
| Sugar metabolism | Galactose | 6.1 | 7.1 | GC |
| Sugar metabolism | Glyceraldehyde | 0.5 | 0.5 | GC |
| Sugar metabolism | Glycerol-3-Phosphate, polar fraction | 0.5 | 0.5 | GC |
| Sugar metabolism | Maltitol | 1.7 | 2.1 | GC |
| Sugar metabolism | Maltotriose | 2.2 | 2.5 | GC |
| Tocopherol and related | beta/gamma-Tocopherol | 1.7 | 2.9 | LC |
| Tocopherol and related | delta-Tocopherol | 2.0 | 4.2 | LC |

TABLE 4-continued

Results of the analysis of seeds from OsLEA3a transformants, the min_ratio and max_ratio are relative to the control plants

| METABOLITE CLASS | METABOLITE | MIN RATIO | MAX RATIO | METHOD |
|---|---|---|---|---|
| Tocopherole and related | alpha-Tocotrienol | 0.3 | 0.5 | LC |
| Tocopherole and related | beta/gamma-Tocotrienol | 1.4 | 2.1 | LC |
| Wax Components | Cerotic Acid (C26:0) | 0.8 | 0.8 | GC |

Column 2 shows the metabolite analyzed, column 1 gives the metabolic class to which the metabolite belongs. Columns 3 and 4 show the minimum and maximum ratio, from which the range of increase or decrease of the analyzed metabolite as found in independent experiments between the transgenic plants and their wild type respective null-segregant control lines may be derived. Column 4 indicates the analytical method (Gas Chromatography or Liquid Chromatography). The table shows that the ratio_by_control values within the group of amino acids may range between 0.7 and 7.7; within the group of carotenoids between 1.8 and 19.3; within the group of cofactors between 1.3 and 1.5; within the group of fatty acids and related metabolites between 0.3 and 0.9; within the group of organic acids between 1.4 and 20.0; within the group of phenolics between 1.4 and 8.5; within the group of phytohormones and phytosterols between 1.0 and 10.9; within the group of sugar metabolites between 0.5 and 7.1, within the group of tocopherol and related metabolites between 0.3 and 4.2.

The invention claimed is:

1. A method for increasing plant yield relative to control plants, comprising increasing expression in a plant of a nucleic acid encoding an OsLEA3a polypeptide or a homologue thereof, and optionally selecting for plants having increased yield, provided that said OsLEA3a polypeptide or homologue thereof is not SEQ ID NO: 22 (*Hordeum vulgare*).

2. The method according to claim 1, wherein said increased expression is effected by introducing a genetic modification in the locus of a gene encoding a OsLEA3a polypeptide or a homologue thereof.

3. The method according to claim 2, wherein said genetic modification is effected by one of: T-DNA activation, TILLING, site-directed mutagenesis or directed evolution.

4. The method according to claim 1, wherein said increased yield is increased seed yield.

5. The method according to claim 1, wherein said increased yield is selected from: increased total weight of seeds, increased number of filled seeds or increased harvest index.

6. A plant obtained by the method according to claim 1.

7. The transgenic plant according to claim 6, wherein said plant is a monocotyledonous plant.

8. Products directly derived from the plant according to claim 7 and/or from harvestable parts therefrom.

9. The transgenic plant of claim 7, wherein the monocotyledonous plant is sugar cane, rice, maize, wheat, barley, millet, rye, oats, or sorghum.

10. Harvestable parts of the plant according to claim 6.

11. Harvestable parts of a plant according to claim 10 wherein said harvestable parts are seeds.

12. A method for increasing plant yield relative to control plants, comprising introducing and expressing in a plant an OsLEA3a nucleic acid or a variant thereof, provided that said OsLEA3a nucleic acid or variant thereof does not encode SEQ ID NO: 22 (*Hordeum vulgare* LEA3a).

13. The method according to claim 12, wherein said nucleic acid encodes a homologue of the OsLEA3a protein of SEQ ID NO: 2.

14. The method according to claim 13, wherein said OsLEA3a nucleic acid or variant thereof is overexpressed in a plant.

15. The method according to claim 13, wherein the OsLEA3a nucleic acid or variant thereof is of plant origin.

16. The method according to claim 13, wherein the OsLEA3a nucleic acid or variant thereof is operably linked to a constitutive promoter.

17. The method according to claim 16, wherein said constitutive promoter is a GOS2 promoter.

18. The method of claim 13, wherein the OsLEA3a nucleic acid or variant thereof is from a monocotyledonous plant.

19. The method claim 13, wherein the OsLEA3a nucleic acid or variant thereof is from *Oryza sativa*.

20. The method according to claim 12, wherein said variant is a portion of an OsLEA3a nucleic acid or a sequence capable of hybridising to an OsLEA3a nucleic acid, which portion or hybridising sequence encodes a polypeptide comprising 2 LEA_4 domains and the OsLEA3a consensus signature sequence of SEQ ID NO: 3.

21. A construct comprising:
(i) an OsLEA3a nucleic acid or a variant thereof;
(ii) one or more control sequences operably linked to the nucleic acid sequence of (a), provided that said OsLEA3a nucleic acid or a variant thereof does not encode SEQ ID NO: 22 (*Hordeum vulgare* LEA3a).

22. The construct according to claim 21, wherein said control sequence is a constitutive promoter.

23. The construct according to claim 22, wherein said constitutive promoter is a GOS2 promoter.

24. The construct according to claim 23, wherein said GOS2 promoter is as represented by SEQ ID NO: 6.

25. A plant transformed with the construct of claim 21.

26. A method for the production of a transgenic plant having increased yield compared to control plants, which method comprises:
(i) introducing and expressing in a plant or plant cell an OsLEA3a nucleic acid or variant thereof;
(ii) cultivating the plant cell under conditions promoting plant growth and development, provided that said OsLEA3a nucleic acid or variant thereof does not encode SEQ ID NO: 22 (Hordeum vulgare LEA3a).

27. A transgenic plant having increased yield when grown under non-stress conditions, resulting from an OsLEA3a nucleic acid or a variant thereof introduced into said plant.

28. The transgenic plant of claim 27, wherein the plant is a monocotyledonous plant.

29. A method for improving yield in a plant comprising transforming a plant or plant cell with an OsLEA3a nucleic acid or variant thereof, or a nucleic acid encoding an OsLEA3a polypeptide or a homologue thereof, and growing the plant or plant cell under non-stress conditions relative to control plants.

30. The method according to claim 29, wherein the improved yield is improved seed yield of one or more of: increased total weight of seeds, increased number of filled seeds or increased harvest index.

31. A method of identifying a plant that has increased yield relative to wild-type plants, comprising determining if the plant has increased expression of an LEA3a polypeptide or has a variant of an LEA3a polypeptide that results in increased activity of the LEA3a polypeptide, growing the plant and comparing the yield of the plant with wild-type plants, thereby identifying a plant that has increased yield.

32. The Method of claim 31, wherein the increased yield is increased seed yield.

33. Plant seed having altered metabolite levels wherein the ratio of the metabolite levels in said plant seed compared to those of control plant seeds ranges within the group of amino acids between 0.7 and 7.7; within the group of carotenoids between 1.8 and 19.3; within the group of cofactors between 1.3 and 1.5; within the group of fatty acids and related metabolites between 0.3 and 0.9; within the group of organic acids between 1.4 and 20.0; within the group of phenolics between 1.4 and 8.5; within the group of phytohormones and phytosterols between 1.0 and 10.9; within the group of sugar metabolites between 0.5 and 7.1, within the group of tocopherol and related metabolites between 0.3 and 4.2; which plant has modulated expression of a nucleic acid encoding an OsLEA3 protein or a homologue thereof.

* * * * *